(12) United States Patent
Critcher et al.

(10) Patent No.: US 7,803,832 B2
(45) Date of Patent: Sep. 28, 2010

(54) N-(1-ARYLPYRAZOL-4L)SULFONAMIDES AND THEIR USE AS PARASITICIDES

(75) Inventors: Douglas James Critcher, Sandwich (GB); Nigel Derek Arthur Walshe, Sandwich (GB); Christelle Lauret, Fleac (FR)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 0 days.

(21) Appl. No.: 12/628,691

(22) Filed: Dec. 1, 2009

(65) Prior Publication Data

US 2010/0075956 A1  Mar. 25, 2010

Related U.S. Application Data

(62) Division of application No. 10/593,133, filed as application No. PCT/IB2005/000597 on Mar. 7, 2005, now Pat. No. 7,687,533.

(60) Provisional application No. 60/571,415, filed on May 13, 2004.

(30) Foreign Application Priority Data

Mar. 18, 2004 (GB) .................................. 0406137.0

(51) Int. Cl.
A01N 43/56 (2006.01)

(52) U.S. Cl. .................................. 514/407; 548/372.1
(58) Field of Classification Search ................. 514/407; 548/372.1
See application file for complete search history.

(56) References Cited

U.S. PATENT DOCUMENTS

| | | | |
|---|---|---|---|
| 4,806,144 | A | 2/1989 | Schallner et al. |
| 4,936,892 | A | 6/1990 | Gehring et al. |
| 5,232,940 | A | 8/1993 | Hatton et al. |
| 5,618,945 | A | 4/1997 | Casado et al. |
| 6,441,018 | B2 | 8/2002 | Faraci et al. |
| 2008/0261940 | A1 | 10/2008 | Critcher et al. |

FOREIGN PATENT DOCUMENTS

| | | |
|---|---|---|
| DE | 195 11 269 | 10/1995 |
| EP | 0 627 423 | 12/1994 |
| EP | 1 319 657 | 6/2003 |
| WO | 87/03781 | 7/1987 |
| WO | 94/21606 | 9/1994 |
| WO | 96/12706 | 5/1996 |
| WO | 98/24767 | 6/1998 |
| WO | 98/28278 | 7/1998 |
| WO | 00/71532 | 11/2000 |
| WO | 03/037274 | 5/2003 |
| WO | 03/051833 | 6/2003 |
| WO | 2004/043951 | 5/2004 |
| WO | 2004/049797 | 6/2004 |

OTHER PUBLICATIONS

Padeiskaya et al. Vestnik Moskovskogo Universiteta, Sriya 2: Khimiya (1963), 18(1), 69-73.*
Fusco et al. Farmaco, Edizione Scientifica (1968), 23(10), 919-944.*
Hainzl et al., "Mechanisms for Selective Toxicity of Fipronil Insecticide and Its Sulfone Metabolite and Desulfinyl Photoproduct", Chem. Res. Toxicol., 11(12):1529-1935, 1998.
PCT International Search Report, PCT/IB05/000597, 2005.
Section Ch, Week 199340 Derwent Publications Ltd., London, GB; AN 1993-317444.
Chemical Abstracts Service, Database accession No. 1965:431646.
Chemical Abstracts Service, Database accession No. 1969:36415.
Chemical Abstracts Service, Database accession No. 1964:3141.
Guarneri and Duda, "Contributo alla conoscenza di pirazolsulfonamidi", Annali Di Chimica, 49:958-963, 1959.
Koch et al., "QSAR and Molecular Modelling for a Series of Isomeric X-Sulfanilamido-1-phenylpyrazoles", Quantitative Structure-Activity Relationships, 12(4):373-382, 1993.
Alberti and Tironi, "Pyrazolic Sulfanilamides. VIII. Chloro-derivatives of 1-phenyl-4-sulfanilamidopyrazole", Il Farmaco, Edizione Scientifica, 21(12):883-891, 1966.
Alberti and Tironi, "Pyrazolic Sulfanilamides. VI. 1-(Tolyl)-Sulfanilamidopyrazole Derivatives of 3-aminopyrazole, 4-aminopyrazole and 3-methyl-5-aminopyrazole", Il Farmaco, Edizione Scientifica, 19(7):618-637, 1964.
Alberti and Tironi, "Pyrazolic Sulfanilamides. V. Dimethoxysulfanilamidopyrazole Derivatives of N-(M,P-dimethoxyphenyl)pyrazole", Il Farmaco, Edizione Scientifica, 19(5):459-473, 1964.
Alberti and Tironi, "Pyrazolic Sulfanilamides. IV. Methoxysulfanilamidopyrazole derivatives of 1-phenyl-4-aminopyrazole", Il Farmaco, Edizione Scientifica, 17(6):460-467, 1962.

(Continued)

*Primary Examiner*—Kamal A Saeed
*Assistant Examiner*—Valerie Rodriguez-Garcia
(74) *Attorney, Agent, or Firm*—Paul M. Misiak

(57) ABSTRACT

The invention relates to a sulfonamide compound of formula (I) or a pharmaceutically, veterinarily or agriculturally acceptable salt or solvate thereof, where the groups $R^1$-$R^5$ are described in the description, to compositions comprising such compounds, processes for their synthesis and their use as parasiticides.

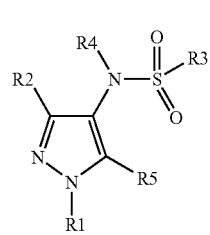

(I)

13 Claims, No Drawings

OTHER PUBLICATIONS

Alberti and Tironi, "Pyrazolic Sulfanilamides. XIII. Hydroxyderivatives of 1-phenyl-3-sulfanilamidopyrazole and 1-phenyl-4-sulfanilamidopyrazole", Il Farmaco, Edizione Scientifica, 29(12):957-966, 1974.

Alberti and Tironi, "Pyrazolic Sulfanilamides. XI. Ethoxy derivatives of phenyl-3-sulfanilamidopyrazole, phenyl-4-sulphanilamidopyrazole, 1-phenyl-5-sulfanilamidopyrazole, 1-phenyl-3-methyl-5-sulfanilamidopyrazole", Il Farmaco, Edizione Scientifica, 26(1):66-88, 1971.

Fusco et al., "Synthesis and pharmacological properties of pyrazole compounds. I. Derivatives of 1-phenyl-4-aminopyrazoles", Il Farmaco, Edizione Scientifica, 23(10):919-944, 1968.

Vippagunta et al., "Crystalline solids", Advanced Drug Delivery Reviews, 48:3-26, 2001.

Souillac and Rytting, "Characterization of Delivery Systems, Differential Scanning Calorimetry", in Encyclopedia of Controlled Drug Delivery, 1999, John Wiley & Sons, pp. 212-227.

* cited by examiner

N-(1-ARYLPYRAZOL-4L)SULFONAMIDES AND THEIR USE AS PARASITICIDES

CROSS-REFERENCE TO RELATED APPLICATIONS

This application is a divisional application of U.S. patent application Ser. No. 10/593,133, filed Nov. 30, 2006, now allowed, which is a 371 filing of PCT/IB/2005/000597, filed Mar. 7, 2005, which claims benefit of Great Britain Application No. 0406137.0, filed Mar. 18, 2004, and U.S. Provisional Application No, 60/571,415, filed May 13, 2004, hereby incorporated by reference in its entirety.

The present invention relates to pesticidal compounds and a process for their preparation. More particularly, the present invention relates to N-(1-arylpyrazol-4-yl)sulfonamides which possess antiparasitic activity. In particular, we have identified a series of N-(1-arylpyrazol-4-yl)sulfonamides which have improved activity and/or a longer duration of action and/or improved safety.

Sulphamoyl (reversed sulphonamides) arylpyrazoles for the control of arthropod, plant nematode, or helminth pests have also been disclosed in, for example, EP-234119, US-2002016333, WO-0258690 and DE-19511269.

5-sulphonamido-1-arylpyrazoles have been disclosed as having utility as herbicides in, for example, EP-0192951 and EP-302328.

U.S. Pat. No. 5,618,945 relates to a process for sulphinylation of compounds such as arylpyrazoles, by the treatment of a compound such as RS(O)X, where X is commonly Cl, and discloses compounds of formula R—S(O)NH-Het where Het can be N-arylpyrazole, although it is not clear which substitution pattern is referred to.

Some pyrazoles possessing bactericidal activity are disclosed in WO-9315060 for use in crop protection. Among the many structures disclosed are some N-heterocyclic pyrazol-4-yl sulfonamides.

WO00/71532, WO03/51833, WO01/19788, WO01/19798, WO03/37274, WO04/00318, WO98/57937 and WO96/12706 all generally describe pyrazole compounds for uses unrelated to those described for the present invention.

The prior art compounds do not always demonstrate good activity or a long duration of action against parasites. Similarly, some parasiticidal agents are useful only for a narrow spectrum of parasites. Modern pesticides must meet many demands, including long duration, broad spectrum of action, low toxicity, combination with other active substances and/or different formulation excipients. The occurrence of resistance is also possible. Consequently the search for new antiparasitic agents is ongoing and there is a constant demand for novel compounds which are advantageous over the known compounds in one or more of these aspects.

The aim of the present invention is to provide a compound which can be conveniently administered as an antiparasitic agent. In particular an agent is sought which can be used in the treatment of human or animal parasitic diseases or can be used in agricultural or horticultural applications. One aim is to provide an agent which can be used in humans, livestock (including sheep, pigs and cattle), companion animals (including cats, dogs and horses). The agent is intended to control arthropods, arachnids, nematodes and helminths including flies, fleas, mites and ticks.

Another aim is to provide compounds with good pharmacokinetics and extended duration of action and thus which prevents re-establishment of infestation over long periods of time.

It is a further aim to provide a compound suitable for oral, parenteral or topical administration which is able to kill existing parasites and prevent infestation. This has benefits in terms of compliance and labour costs as less frequent dosing is needed and the dosing timetable is easier. This in turn assists in minimising the re-incidence of infestation as a subsequent dosage is less likely to be overlooked.

It is an aim of the present invention to overcome various disadvantages of or improve on the properties of prior art compounds. Thus it is an aim of the invention to provide an arylpyrazole which has improved activity relative to prior art compounds against parasites. The compounds of the present invention have especially good ability to control a broad spectrum of arthropods as shown by the results of tests demonstrating their potency and efficacy. Surprisingly, we have found that the compounds of the present invention are significantly more active against fleas and/or have a greater duration of action than similar prior art compounds. One advantage of the compounds of the present invention is that treatment with these compounds can also lead to a reduced incidence of allergy to the parasite which is responsible for the infestation. For example, the incidence of flea allergies which can cause flea allergic dermatitis may be reduced.

It is also desirable that the compounds of the present invention should have an improved pharmacokinetic profile, improved safety, longer half-life, improved persistence and improved solubility. It is also desired that the compounds should lead to a reduced incidence of emesis.

Unfortunately, many potent pesticidal aryl pyrazoles and their derivatives also have undesirable effects such as emesis on animals regardless of whether or not the animal itself is being treated directly. This unwanted toxicity can limit the dose that can be used and thus limits the range of parasites that can be controlled. Thus it is an aim of the present invention to address the need for the development and use of new and efficacious pesticides that can control pests for longer periods of time but which are not toxic to animals susceptible to pest infestations or animals that might come into contact with areas susceptible to pest infestations.

It is a further aim to provide a convenient, synthetically efficient process for the production of the aryl pyrazoles and the intermediates of the present invention. It is also an aim to provide a route to the compounds of the invention which offers a good yield and which ideally avoids the use of unnecessary synthetic steps and/or purification steps.

The present invention satisfies some or all of the above aims.

According to the present invention, there is provided a compound of formula (I) or a pharmaceutically, veterinarily or agriculturally acceptable salt or solvate thereof,

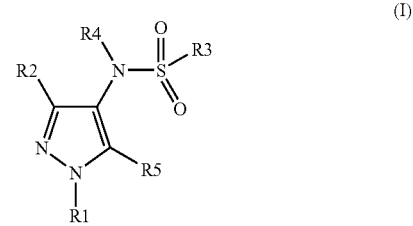

(I)

wherein:

$R^1$ represents phenyl or heteroaryl, optionally substituted by one or more groups independently selected from halo, cyano, hydroxy, $C_{1-6}$ alkyl, $C_{1-6}$ haloalkyl, $C_{1-6}$ alkoxy, $C_{1-6}$ haloalkoxy, $C_{1-6}$ alkanoyl, $C_{1-6}$ haloalkanoyl, —S(O)$_n$C$_{1-6}$ alkyl, —S(O)$_n$C$_{1-6}$haloalkyl and pentafluorothio;

$R^2$ represents hydrogen, halo, cyano, nitro, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, —S(O)$_n$C$_{1-6}$ alkyl, —S(O)$_n$C$_{1-6}$haloalkyl, —(C$_{0-3}$alkylene)-C$_{3-8}$ cycloalkyl, $C_{1-6}$ alkanoyl, optionally substituted by $C_{1-6}$ alkoxy, $C_{1-6}$ haloalkanoyl, optionally substituted by $C_{1-6}$ alkoxy, phenyl, het, —(C$_{0-3}$alkylene)-N(R$^a$)R$^b$, —(C$_{0-3}$alkylene)-C(O)NR$^a$R$^b$ or —(C$_{0-3}$alkylene)N(R$^c$)C(O)R$^8$;

$R^3$ represents $C_{1-6}$ alkyl, $C_{1-6}$ haloalkyl, $C_{2-6}$ alkenyl, $C_{2-6}$ haloalkenyl, —(C$_{0-3}$alkylene)-C$_{3-8}$ cycloalkyl, —(C$_{1-3}$alkylene)-S(O)$_n$C$_{1-6}$alkyl, —(C$_{1-3}$alkylene)-S(O)$_n$C$_{1-6}$haloalkyl, —(C$_{0-3}$alkylene)-N(R$^a$)R$^b$, —(C$_{0-3}$alkylene)-phenyl, —(C$_{0-3}$ alkylene)-het, —(C$_{2-3}$alkenylene)-phenyl, —(C$_{2-3}$ alkenylene)-het, $C_{1-6}$ alkanoyl, $C_{1-6}$ haloalkanoyl or N(R$^c$)CO$_2$R$^8$;

$R^4$ represents hydrogen, $C_{1-6}$ alkyl, $C_{1-6}$haloalkyl, —(C$_{0-3}$alkylene)-R$^7$ or —(C$_{1-3}$alkylene)-R$^8$;

or $R^3$ and $R^4$ taken together with the nitrogen and sulphur atoms to which they are attached form a 4 to 7-membered ring;

$R^5$ represents hydrogen, hydroxy, halo, $C_{1-6}$ alkyl, $C_{1-6}$ haloalkyl, $C_{2-6}$ alkenyl, $C_{2-6}$ haloalkenyl, $C_{1-6}$ alkoxy, $C_{1-6}$ haloalkoxy, —N=C(R$^{13}$)(C$_{0-5}$alkylene)-R$^{11}$ or N(R$^{12}$)R$^{13}$;

$R^6$ represents $C_{1-6}$ alkyl or $C_{1-6}$ haloalkyl;

$R^7$ represents $C_{3-8}$cycloalkyl, —S(O)$_n$R$^9$, phenyl, het, —CO$_2$R$^6$ or C(O)N(R$^a$)R$^b$;

$R^8$ represents hydroxy, $C_{1-6}$ alkoxy, $C_{1-6}$ haloalkoxy, cyano, —N(R$^a$)R$^{13}$ or —O—C(O)R$^6$;

$R^9$ represents $C_{1-6}$ alkyl, $C_{1-6}$ haloalkyl, $C_{3-8}$cycloalkyl, —N(R$^a$)R$^b$, phenyl or het;

$R^{10}$ represents hydrogen, $C_{1-6}$ alkyl or $C_{1-6}$ haloalkyl;

$R^{11}$ represents hydrogen, hydroxy, $C_{1-3}$alkoxy, —N(R$^a$)R$^b$, phenyl, het or $C_{3-8}$cycloalkyl, with the proviso that —N=C(R$^{13}$)(C$_{0-5}$alkylene)-R$^{11}$ is not N=CH$_2$;

$R^{12}$ represents hydrogen, $C_{1-6}$ alkyl, $C_{1-6}$ haloalkyl, $C_{1-6}$ alkenyl or $C_{1-6}$ haloalkenyl;

$R^{13}$ represents hydrogen, $C_{1-6}$ alkyl, $C_{1-6}$ haloalkyl, $C_{1-6}$ alkenyl, $C_{1-6}$ haloalkenyl $C_{3-8}$cycloalkyl, phenyl, het, —(C$_{1-6}$alkylene)-R$^{14}$, —C(O)$_p$R$^{15}$ or —CON(R$^{16}$)(C$_{1-6}$alkylene)-R$^{17}$;

$R^{14}$ represents hydroxy, $C_{1-3}$alkoxy, $C_{1-3}$haloalkoxy, $C_{3-6}$cycloalkyl, phenyl, het or —N(R$^a$)R$^b$;

$R^{15}$ represents $C_{1-6}$ alkyl, $C_{1-6}$ haloalkyl or —(C$_{1-6}$alkylene)-C$_{1-3}$alkoxy;

$R^{16}$ represents hydrogen, $C_{1-6}$ alkyl or $C_{1-6}$ haloalkyl;

$R^{17}$ represents hydrogen or N(R$^a$)R$^b$;

$R^a$ and $R^b$ independently represent hydrogen, $C_{1-6}$ alkyl, $C_{1-6}$ haloalkyl, $C_{2-6}$ alkenyl or $C_{2-6}$ haloalkenyl, or R$^a$ additionally represents —(C$_{0-3}$alkylene)C$_{3-5}$ cycloalkyl, —(C$_{0-3}$alkylene)phenyl or —(C$_{0-3}$alkylene)het, or together R$^a$ and R$^b$ form a 4- to 7-membered ring, optionally substituted by one or more groups independently selected from halo, hydroxy, $C_{1-6}$ alkyl, $C_{1-6}$haloalkyl, $C_{1-6}$ alkoxy and $C_{1-6}$haloalkoxy;

$R^c$ represents hydrogen, $C_{1-6}$ alkyl, $C_{1-6}$ haloalkyl, $C_{2-6}$ alkenyl, $C_{2-6}$ haloalkenyl, —(C$_{0-3}$alkylene)C$_{3-8}$ cycloalkyl, —(C$_{0-3}$alkylene)phenyl or —(C$_{0-3}$alkylene)het;

n represents an integer selected from 0, 1 and 2;

p represents an integer selected from 1 and 2;

where het represents a four- to seven-membered heterocyclic group, which is aromatic or non-aromatic and which contains one or more heteroatoms selected from nitrogen, oxygen, sulfur and mixtures thereof;

where heteroaryl represents a 5 or 6 membered aromatic ring which contains 1-3 heteroatoms selected from N, O and 5 or 4-N atoms to form a tetrazolyl;

where both phenyl and het may be optionally substituted, where the valence allows, by one or more substituents independently selected from halo, hydroxy, cyano, nitro, $C_{1-6}$ alkyl, $C_{1-6}$haloalkyl, $C_{1-6}$ alkenyl, $C_{1-6}$haloalkenyl, $C_{1-6}$alkoxy, $C_{1-6}$haloalkoxy, $C_{3-8}$ cycloalkyl, $C_{1-6}$ alkanoyl, $C_{1-6}$ haloalkanoyl, $C_{1-6}$ alkylcarbonyloxy, $C_{1-6}$ alkoxycarbonyl and NR$^a$R$^b$;

where $C_{3-8}$cycloalkyl may be optionally substituted by one or more groups independently selected from halo, $C_{1-6}$alkyl, $C_{1-6}$haloalkyl, $C_{1-6}$ alkenyl, $C_{1-6}$haloalkenyl, hydroxy, $C_{1-6}$alkoxy and $C_{1-6}$haloalkoxy; and where any alkylene or alkenylene group may be optionally substituted by one or more halo.

According to formula (I), $C_{1-6}$ haloalkyl, $C_{1-6}$ haloalkoxy or $C_{1-6}$haloalkanoyl means a $C_{1-6}$ alkyl, $C_{1-6}$ alkoxy or $C_{1-6}$alkanoyl substituted by 1 to 5 halo groups chosen independently, suitably fluoro groups. Also, 'halo' means a group selected from fluoro, bromo, chloro, bromo or iodo.

According to formula (I), a $C_{1-6}$ alkyl, $C_{1-6}$ alkoxy or $C_{1-6}$alkanoyl, including the corresponding halo substituted groups, may be straight-chained or, where possible, branched. An alkylene group refers to a straight-chained or, where possible, branched linking group and alkenylene refers to a linking group containing one double bond. For the avoidance of any doubt, a C$_0$alkylene group refers to a direct link between the connecting groups.

Suitably, $R^1$ is substituted phenyl, substituted in one or both of the 2- and 6-positions and at the 4-position with a substituent independently selected from the group comprising halogen, e.g. chloro, $C_{1-6}$ alkyl, e.g. methyl, $C_{1-6}$ haloalkyl, e.g. trifluoromethyl, $C_{1-6}$ alkoxy, e.g. methoxy, $C_{1-6}$ alkylthio, e.g. methylthio, $C_{1-6}$ haloalkoxy, e.g. trifluoromethoxy or difluoromethoxy, $C_{1-6}$ haloalkylthio, e.g. trifluoromethylthio, and pentafluorothio.

Preferably, $R^1$ is phenyl substituted at one or both of the 2- and 6-positions by halo, e.g. chloro, and at the 4-position by a group selected from $C_{1-4}$ alkyl substituted with one or more independently selected halo groups, e.g. trifluoromethyl, $C_{1-4}$ alkoxy substituted with one or more independently selected halo atoms, e.g. trifluoromethoxy or difluoromethoxy, $C_{1-6}$ alkylthio substituted with one or more independently selected halo atoms, e.g. trifluoromethylthio, and pentafluorothio.

More preferably, $R^1$ is a phenyl group which bears chloro substituents at the 2- and 6-positions, and a substituent at the 4-position selected from trifluoromethyl, difluoromethoxy, trifluoromethoxy, trifluoromethylthio and pentafluorothio.

Still more preferably, $R^1$ is a phenyl group in which the 2- and 6-substituents are chloro and the 4-substituent is selected from trifluoromethyl and pentafluorothio.

Where $R^1$ is a heteroaryl, $R^1$ is suitably a 3,5-disubstituted pyridin-2-yl, wherein the 3-substituent is selected from hydrogen and halo, and the 5-substituent is selected from halo, e.g. chloro, pentafluorothio, $S(O)_nC_{1-6}$ alkyl, $S(O)_nC_{1-6}$ haloalkyl, $C_{1-6}$ alkyl, $C_{1-6}$ haloalkyl, e.g. trifluoromethyl, $C_{1-6}$ alkoxy and $C_{1-6}$ haloalkoxy.

Suitably, het represents an optionally substituted aromatic or non-aromatic 5- or 6-membered heterocyclic group containing 1, 2 or 3 heteroatoms, which are independently selected from N, O or S atoms. More suitably, het is selected from pyrazolyl, imidazolyl, oxazolyl, isoxazolyl, thiazolyl, isothiazolyl, furanyl, thiophenyl, pyrrolyl, triazolyl, oxadiazolyl, azetidinyl, pyrrolidyl, piperidyl, pyridyl, pyrazinyl, pyrimidyl and morpholinyl, wherein the aforementioned groups may be optionally substituted by one or more groups independently selected from $C_{1-6}$ alkyl, e.g. methyl, $C_{1-6}$ haloalkyl, e.g. trifluoromethyl, halogen, e.g. fluoro, and $N(R^a)R^b$, e.g. amino.

Suitably, $R^2$ is selected from hydrogen, cyano, $C_{1-6}$ haloalkyl, e.g. trifluoromethyl, $C_{3-8}$ cycloalkyl, e.g. cyclopropyl, $C_{1-6}$ alkanoyl, e.g. acetyl, and $—C(O)N(R^a)R^b$, e.g. aminocarbonyl.

More preferably, $R^2$ is selected from hydrogen, trifluoromethyl, cyclopropyl, acetyl, aminocarbonyl and cyano. Yet more preferably, $R^2$ is selected from trifluoromethyl and cyano. Most preferably, $R^2$ is cyano.

When $R^3$ is $—(C_{0-3}alkylene)-N(R^a)R^b$, suitably the N— is directly linked and $N(R^a)R^b$ is suitably amino or di-$C_{1-6}$ alkylamino, e.g. N,N-dimethylamino.

Suitably, $R^3$ is selected from $C_{1-6}$ alkyl, e.g. methyl, ethyl, n-propyl or i-propyl, $C_{1-6}$ haloalkyl, e.g. trifluoromethyl or 2,2,2-trifluoroethyl, $C_{3-8}$cycloalkyl, e.g. cyclopropyl, $—(C_{1-3}alkylene)-S(O)_nC_{1-6}$alkyl, e.g. methylsulfonylmethyl or 1-methylsulfonylethyl, $N(R^a)R^b$, e.g. amino or N,N-dimethylamino, $—N(R^c)CO_2R^6$, e.g. tert-butoxycarbonylamino, optionally substituted phenyl, e.g. by one or more halo, e.g. fluoro, optionally substituted benzyl, e.g. by one or more halo, e.g. fluoro, $—(C_{2-3}alkenylene)$-phenyl, e.g. 2-phenylethenyl, and $C_{1-6}$alkanoyl, e.g. propan-2-oyl.

Preferably, $R^3$ is selected from $C_{1-6}$ alkyl, e.g. methyl, ethyl, n-propyl or i-propyl, $C_{1-6}$ haloalkyl, e.g. trifluoromethyl or 2,2,2-trifluoroethyl, $C_{3-8}$ cycloalkyl, e.g. cyclopropyl, $—(C_{1-3}alkylene)-S(O)_nC_{1-6}$alkyl, e.g. methylsulfonylmethyl, $—N(R^a)R^b$, e.g. amino or N,N-dimethylamino, $C_{1-6}$ alkanoyl, e.g. propan-2-oyl, $—N(R^a)CO_2R^6$, e.g. tert-butoxycarbonylamino, phenyl, optionally substituted by one or more halo, e.g. 3,4-difluorophenyl, and benzyl.

More preferably, $R^3$ is selected from methyl, ethyl, trifluoromethyl and 2,2,2-trifluoroethyl. Most preferably, $R^3$ is methyl.

Where $R^4$ is $—(C_{0-3}alkylene)-R^7$, the link is suitably a direct or a methylene link.

Where $R^4$ is $—(C_{1-3}alkylene)-R^8$, the link is suitably a methylene or ethylene link.

Where $R^4$ represents $—(C_{0-3}alkylene)-S(O)_nR^9$, n is suitably 0 or 2, preferably 2, and $R^9$ is suitably selected from $C_{1-6}$ alkyl, e.g. methyl, $C_{1-6}$ haloalkyl, e.g. trifluoromethyl or 2,2,2-trifluoroethyl, $C_{3-8}$ cycloalkyl, e.g. cyclopropyl, $N(R^a)R^b$, e.g. amino or N,N-dimethylamino, and phenyl, optionally substituted by one or more halo, e.g. fluoro.

Preferably, n is 2, $C_{0-3}$alkylene is a direct link and $R^9$ represents $C_{1-6}$ alkyl, e.g. methyl, or $C_{1-6}$ haloalkyl, e.g. trifluoromethyl or 2,2,2-trifluoroethyl.

Where $R^4$ represents $—(C_{0-3}alkylene)-C_{3-8}$ cycloalkyl, $C_{0-3}$alkylene is suitably a direct link or methylene, $C_{3-8}$ cycloalkyl suitably represents cyclopropyl, cyclobutyl or cyclopentyl, optionally substituted by one or more halo, e.g. fluoro, $C_{1-6}$ alkyl, e.g. methyl or $C_{1-6}$ haloalkyl, e.g. trifluoromethyl. Where $R^4$ represents $—(C_{0-3}alkylene)-C_{3-8}$ cycloalkyl, a preferred group is 1-(trifluoromethyl)cyclopropylmethyl.

When $R^4$ represents $—(C_{0-3}alkylene)$-het, the link is suitably a methylene or ethylene link and het is suitably selected from pyrazolyl, imidazolyl, oxazolyl, isoxazolyl, thiazolyl, isothiazolyl, furanyl, thiophenyl, pyrrolyl, triazolyl, oxadiazolyl, pyrrolidyl, pyridyl, pyrazinyl, pyrimidyl and morpholinyl, wherein the aforementioned groups may be optionally substituted by one or more groups independently selected from $C_{1-6}$ alkyl, e.g methyl, halogen, e.g. fluoro, and $N(R^a)R^b$, e.g. amino. Preferably, when $R^4$ represents $(C_{1-2}alkylene)$-het, het is selected from pyrazolyl, imidazolyl, isoxazolyl, pyrrolyl, triazolyl, oxadiazolyl, pyrrolidyl, pyridyl, pyrazinyl, pyrimidyl and morpholinyl, wherein the aforementioned groups may be optionally substituted by one or more groups independently selected from $C_{1-6}$ alkyl, halogen, e.g. fluoro, and $N(R^a)R^b$, e.g. amino. More preferably, when $R^4$ represents $—(C_{0-3}alkylene)$-het, $C_{0-3}$alkylene is a methylene link and het is selected from imidazolyl, isoxazolyl, oxadiazolyl and pyridyl, where each ring may be optionally substituted by $C_{1-6}$ alkyl, e.g. methyl.

When $R^4$ represents $—(C_{0-3}alkylene)$-phenyl, phenyl is suitably optionally substituted by one or more halo, e.g. fluoro, e.g. 4-fluoro.

When $R^4$ represents $—(C_{1-3}alkylene)-N(R^a)R^b$, this is suitably 2-N,N-dimethylaminoethyl.

When $R^4$ represents $—(C_{1-3}alkylene)-C(O)N(R^a)R^b$, this is suitably aminocarbonylmethyl.

Suitably, $R^4$ is selected from hydrogen, $C_{1-6}$ alkyl, e.g. methyl, ethyl or isopropyl, $C_{1-6}$ haloalkyl, e.g. trifluoromethyl, 2,2,2-trifluoroethyl, 2,2-difluoroethyl, 2-fluoroethyl or 2,2,3,3,3-pentafluoropropyl, $(C_{0-3}alkylene)-C_{3-8}$ cycloalkyl, e.g. cyclopropyl, cyclobutyl, cyclopentyl, cyclopropylmethyl, (1-methylcyclopropyl)methyl, 2,2-difluorocyclopropyl or 1-(trifluoromethyl)cyclopropylmethyl, cyanomethyl, 2-hydroxyethyl, $(C_{1-2}alkylene)$-het, e.g. pyrazol-3-ylmethyl, pyrimidin-4-ylmethyl, pyridin-3-ylmethyl, 2-pyrrolidin-1-ylethyl, 2-morpholin-4-ylethyl, 1-methyl-1H-imidazol-2-ylmethyl, pyridin-4-ylmethyl, triazolylethyl, 1,2,4-oxadiazol-3-ylmethyl, pyridin-2-ylmethyl or (5-methylisoxazoly-3-yl)methyl, $(C_{0-3}alkylene)$-phenyl, e.g. benzyl or 4-fluorobenzyl, $(C_{0-1}alkylene)-S(O)_nR^9$, e.g. 1,1,1-trifluoromethylsulfonyl, aminosulfonyl, N,N-dimethylaminosulfonyl, cyclopropylsulfonyl, methylsulfonyl, 4-fluorophenylsulfonyl, 2,4-difluorophenylsulfonyl, (methylsulfonyl)methyl or 2,2,2-trifluoroethylsulfonyl, $(C_{1-3}alkylene)-O—C(O)R^6$, e.g. tert-butylcarbonyloxymethyl, $(C_{1-3}alkylene)-C(O)N(R^a)R^b$, e.g. aminocarbonylmethyl, and $—CO_2R^6$, e.g. methoxycarbonyl.

More preferably, $R^4$ is selected from hydrogen, methyl, ethyl, trifluoromethyl, 2,2-difluoroethyl, 2,2,2-trifluoroethyl, methylsulfonyl, trifluoromethylsulfonyl, 2,2,2-trifluoroethylsulfonyl, aminosulfonyl, N,N-dimethylaminosulfonyl, methylsulfonylmethyl, cyclopropyl, cyclobutyl, cyclopropylmethyl, 1-(trifluoromethyl)cyclopropylmethyl, cyanomethyl, methoxycarbonyl, triazolylethyl, pyrimidin-4-ylmethyl, 1,2,4-oxadiazol-3-ylmethyl, pyrazol-3-ylmethyl, 5-methyl-isoxazol-3-ylmethyl, 2-pyridin-4-ylethyl, aminocarbonylmethyl, benzyl and 4-fluorobenzyl.

Where $R^3$ and $R^4$ form a 4 to 7 membered ring, this is suitably a dioxidoisothiazolidinyl group, e.g. 1,1-dioxidoisothiazolidin-2-yl, or a dioxido-thiazinanyl group, e.g. 1,1-dioxido-1,2-thiazinan-2-yl group.

Where $R^5$ is $—N=C(R^{10})(C_{0-5}alkylene)-R^{11}$, $R^{10}$ is suitably hydrogen and the $C_{0-5}$alkylene is suitably a direct link.

$R^{11}$ is suitably $C_{1-3}$alkoxy, e.g. ethoxy, —N($R^a$)$R^b$, e.g. N,N-dimethyl, or phenyl, optionally substituted by one or more hydroxy.

$R^{12}$ is suitably hydrogen or methyl, preferably hydrogen.

Where $R^{13}$ represents —($C_{1-6}$alkylene)-$R^{14}$, the $C_{1-6}$alkylene is suitably a methylene, ethylene or propylene link and $R^{14}$ is suitably $C_{1-4}$alkoxy, e.g. ethoxy, phenyl, —N($R^a$)$R^b$, e.g. N,N-dimethylamino, het, e.g. pyrrolidinyl, morpholinyl, azetidinyl, piperidinyl or pyridyl, or $C_{3-8}$cycloalkyl, e.g. cyclopropyl.

Where $R^{13}$ represents C(O)$_p R^{15}$ and p represents 1, $R^{15}$ is suitably $C_{1-6}$alkyl, e.g. methyl. When p represents 2, $R^{15}$ is suitably $C_{1-6}$alkyl, e.g. methyl, or $C_{1-6}$haloalkyl, e.g. 2,2,2-trifluoroethyl.

Where $R^{13}$ represents —C(O)N($R^{16}$)($C_{1-6}$alkylene)-$R^{17}$, $R^{16}$ is suitably hydrogen and $C_{1-6}$alkylene is suitably ethylene. $R^{17}$ is suitably amino.

$R^{13}$ is suitably selected from hydrogen, methyl, benzyl, cyclopropylmethyl, 2-N,N-dimethylaminoethyl, acetyl, methoxymethylcarbonyl, methoxycarbonyl, 2,2,2-trifluoroethoxycarbonyl, N-pyrrolidinylethyl, N-morpholinylethyl, N-piperidinylethyl, pyridin-4-ylmethyl, N-azetidinylethyl and aminoethylaminocarbonyl. $R^{13}$ is preferably hydrogen and $R^{12}$ and $R^{13}$ are preferably both hydrogen.

Suitably, $R^5$ is selected from hydrogen, halo, e.g. chloro, $C_{1-6}$ alkoxy, e.g. methoxy, —N═C(H)$R^{11}$, where $R^{11}$ is ethoxy, N,N-dimethyl or phenyl, optionally substituted by one or more hydroxy, e.g. 2,4-di-hydroxy, and —N$R^{12}R^{13}$, e.g. amino, benzylamino, pyridin-4-ylmethylamino, 2-ethoxyethylamino, methylamino, methoxymethylcarbonylamino, cyclopropylmethylamino, methylcarbonylamino, 2-N,N-dimethylaminoethyl(methyl)amino, 2-N-azetidinylethylamino, 2-N-pyrrolidinylethylamino, 2-N-morpholinoethylamino, 2-N-piperidinylethylamino, cyclopropylmethylamino, methoxycarbonylamino, 2,2,2-trifluoroethoxycarbonylamino and 2-aminoethylaminocarbonylamino.

Preferably, $R^5$ is selected from hydrogen, amino, methoxymethylcarbonylamino, cyclopropylmethylamino, 3-N,N-dimethylaminopropylamino, 2-N-azetidinylethylamino, 2-N-piperidinylethylamino, 2-N-pyrrolidinylethylamino, 2-N-morpholinoethylamino, methoxycarbonylamino, ethoxyimino, phenylimino and 2,4-dihydroxyphenylimino. Most preferably, $R^5$ is amino.

A suitable sub-group of the present invention is represented by compounds of formula (Ia),

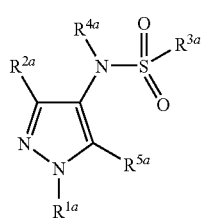

(Ia)

wherein $R^{1a}$ is aryl or heteroaryl optionally substituted by one or more groups independently selected from: hydrogen; halo; $C_{1-6}$ alkyl; $C_{1-6}$ alkoxy which may be optionally substituted with one or more independently selected halo atoms; —S(O)$_{na}C_{1-6}$ alkyl; and pentafluorothio; cyano; $C_{1-6}$ alkanoyl which may be optionally substituted with one or more independently selected halo atoms;

$R^{2a}$ is selected from: hydrogen; halo; $C_{1-6}$ alkyl; —S(O)$_{na}C_{1-6}$ alkyl; —(CH$_2$)$_{ma}C_{3-8}$ cycloalkyl which may be optionally substituted with one or more substituents independently selected from: halo and $C_{1-6}$ alkyl; cyano; nitro; —(CH$_2$)$_{ma}$NR$^{aa}$R$^{ba}$; alkanoyl which may be optionally substituted by one or more groups independently selected from halo and $C_{1-4}$ alkoxy; phenyl; oxadiazole; —C(O)NR$^{aa}$R$^{ba}$; —NR$^{aa}$C(O)R$^{ba}$; $C_{2-6}$ alkenyl; and $C_{2-6}$ alkynyl;

$R^{3a}$ is selected from: $C_{1-6}$ alkyl; —(CH$_2$)$_m$NR$^{aa}$R$^{ba}$; —(CH$_2$)$_{ma}C_{3-8}$ cycloalkyl which may be optionally substituted with one or more substituents independently selected from: halo and $C_{1-6}$ alkyl; —(CH$_2$)$_{ma}$ phenyl; —CH═CH-phenyl; and —(CH$_2$)$_{ma}$ het;

$R^{4a}$ is selected from: hydrogen; $C_{1-6}$ alkyl; —(CH$_2$)$_{ma}C_{3-8}$ cycloalkyl which may be optionally substituted with one or more substituents independently selected from: halo and $C_{1-6}$ alkyl; —(CH$_2$)$_{ma}$S(O)$_p R^{6a}$; —CO$_2$(C$_{1-6}$ alkyl); —(CH$_2$)$_{ma}$ het; and —C(O)NR$^{aa}$R$^{ba}$;

or $R^{3a}$ and $R^{4a}$ taken together with the nitrogen and sulphur atoms to which they are attached form a 4 to 7-membered ring;

$R^{5a}$ is selected from: hydrogen; hydroxy; $C_{1-6}$ alkyl; NR$^{aa}$R$^{ba}$; halo and $C_{1-6}$ alkoxy;

$R^{6a}$ is selected from: $C_{1-6}$ alkyl; NR$^{aa}$R$^{ba}$; $C_{3-8}$ cycloalkyl which may be optionally substituted with one or more substituents independently selected from: halo and $C_{1-6}$ alkyl; het; and phenyl;

each na is independently 0, 1 or 2;

each ma is independently 0, 1, 2 or 3;

pa is 1 or 2;

and wherein het represents a four- to seven-membered heterocyclic group, which is aromatic or non-aromatic and which contains one or more heteroatoms selected from nitrogen, oxygen, sulfur and mixtures thereof, and wherein said heterocyclic ring is optionally substituted and/or terminated where the valence allows with one or more substituents selected from: halo, cyano, nitro, $C_{1-6}$ alkyl, $C_{1-6}$ haloalkyl, $C_{1-6}$ alkoxy, OC(O)$C_{1-6}$ alkyl, C(O)$C_{1-6}$ alkyl, C(O)OC$_{1-6}$ alkyl, and NR$^{aa}$R$^{ba}$;

each $C_{1-6}$ alkyl group can independently be branched or unbranched and optionally substituted by one or more groups selected independently from: cyano; halo; hydroxy; nitro; $C_{1-6}$ alkoxy; NR$^{aa}$R$^{ba}$; S(O)$_{na}$ $C_{1-6}$ alkyl; S(O)$_{na}$ $C_{3-6}$ cycloalkyl; S(O)$_{na}C_{1-6}$ alkylhet; $C_{3-8}$ cycloalkyl; and phenyl;

each phenyl may be optionally substituted by one or more substituents independently selected from: cyano; halo; hydroxy; nitro; $C_{1-6}$ alkyl; $C_{1-6}$ haloalkyl; and $C_{1-6}$ alkoxy; and each $R^{aa}$ and $R^{ba}$ are independently selected from hydrogen; $C_{1-6}$ alkyl; and $C_{3-8}$ cycloalkyl which may be optionally substituted with one or more substituents independently selected from: halo and $C_{1-6}$ alkyl; or $R^{aa}$ and $R^{ba}$ may be taken together with the nitrogen atom to which they are attached to form a 4 to 7-membered ring.

A suitable group of compounds of formula (I) of the present invention are those wherein:

N-{5-amino-3-cyano-1-[2,6-dichloro-4-pentafluorothiophenyl]-1H-pyrazol-4-yl}-N-(2,2-difluoroethyl)methanesulfonamide;

N-{5-amino-3-cyano-1-[2,6-dichloro-4-pentafluorothiophenyl]-1H-pyrazol-4-yl}-1,1,1-trifluoro-N-methylmethanesulfonamide;

N-{5-amino-3-cyano-1-[2,6-dichloro-4-(trifluoromethyl)phenyl]-1H-pyrazol-4-yl}-3,4-difluorobenzenesulfonamide;

N-{5-amino-3-cyano-1-[2,6-dichloro-4-(trifluoromethyl)phenyl]-1H-pyrazol-4-yl}cyclopropanesulfonamide;

N-{5-amino-3-cyano-1-[2,6-dichloro-4-(trifluoromethyl)phenyl]-1H-pyrazol-4-yl}-N-(cyclopropylmethyl)methanesulfonamide;

N-{5-amino-3-cyano-1-[2,6-dichloro-4-(trifluoromethyl)phenyl]-1H-pyrazol-4-yl}-N-(cyanomethyl)methanesulfonamide;

N-{5-amino-3-cyano-1-[2,6-dichloro-4-(trifluoromethyl)phenyl]-1H-pyrazol-4-yl}-N-(pyridin-2-ylmethyl)methanesulfonamide;

N-{5-amino-3-cyano-1-[2,6-dichloro-4-(trifluoromethyl)phenyl]-1H-pyrazol-4-yl}-N-benzylmethanesulfonamide;

N-{5-amino-3-cyano-1-[2,6-dichloro-4-(trifluoromethyl)phenyl]-1H-pyrazol-4-yl}-N-[2-(dimethylamino)ethyl]methanesulfonamide;

N-{5-amino-3-cyano-1-[2,6-dichloro-4-(trifluoromethyl)phenyl]-1H-pyrazol-4-yl}-1-(methylsulfonyl)methanesulfonamide;

N-{5-amino-3-cyano-1-[2,6-dichloro-4-(trifluoromethyl)phenyl]-1H-pyrazol-4-yl}-N-(2-hydroxyethyl)methanesulfonamide;

N-{5-amino-3-cyano-1-[2,6-dichloro-4-(trifluoromethyl)phenyl]-1H-pyrazol-4-yl}-N-isopropylmethanesulfonamide;

N-{5-amino-3-cyano-1-[2,6-dichloro-4-(trifluoromethyl)phenyl]-1H-pyrazol-4-yl}-N,N',N'-trimethylsulfamide;

N-{5-amino-3-cyano-1-[2,6-dichloro-4-(trifluoromethyl)phenyl]-1H-pyrazol-4-yl}-N-[(methylthio)methyl]methanesulfonamide;

N-{5-amino-3-cyano-1-[2,6-dichloro-4-(trifluoromethyl)phenyl]-1H-pyrazol-4-yl}-N-[(5-methylisoxazol-3-yl)methyl]methanesulfonamide;

N-{5-amino-3-cyano-1-[2,6-dichloro-4-(trifluoromethyl)phenyl]-1H-pyrazol-4-yl}-N-(cyclopropylmethyl)-N',N'-dimethylsulfamide;

N-{5-amino-3-cyano-1-[2,6-dichloro-4-(trifluoromethyl)phenyl]-1H-pyrazol-4-yl}-N-{[1-(trifluoromethyl)cyclopropyl]methyl}methanesulfonamide;

N-{5-amino-3-cyano-1-[2,6-dichloro-4-(trifluoromethyl)phenyl]-1H-pyrazol-4-yl}-N-(cyclobutylmethyl)methanesulfonamide;

N-{5-amino-3-cyano-1-[2,6-dichloro-4-(trifluoromethyl)phenyl]-1H-pyrazol-4-yl}-N-(methylsulfonyl)cyclopropanesulfonamide;

N-{5-amino-3-cyano-1-[2,6-dichloro-4-(trifluoromethyl)phenyl]-1H-pyrazol-4-yl}-N-[(dimethylamino)sulfonyl]methanesulfonamide;

N-{5-amino-3-cyano-1-[2,6-dichloro-4-(trifluoromethyl)phenyl]-1H-pyrazol-4-yl}-2,2,2-trifluoro-N-(methylsulfonyl)ethanesulfonamide;

N-{5-amino-3-cyano-1-[2,6-dichloro-4-(trifluoromethyl)phenyl]-1H-pyrazol-4-yl}-1,1,1-trifluoro-N-{[1-(trifluoromethyl)cyclopropyl]methyl}methanesulfonamide;

N-{5-amino-3-cyano-1-[2,6-dichloro-4-(trifluoromethyl)phenyl]-1H-pyrazol-4-yl}-N-(methylsulfonyl)methanesulfonamide;

N-{5-amino-3-cyano-1-[2,6-dichloro-4-(trifluoromethyl)phenyl]-1H-pyrazol-4-yl}-N-(methylsulfonyl)methanesulfonamide;

N-{5-amino-3-cyano-1-[2,6-dichloro-4-(trifluoromethyl)phenyl]-1H-pyrazol-4-yl}methanesulfonamide;

N-{5-amino-3-cyano-1-[2,6-dichloro-4-(trifluoromethyl)phenyl]-1H-pyrazol-4-yl}-N-methylmethanesulfonamide;

N-{5-amino-3-cyano-1-[2,6-dichloro-4-(trifluoromethyl)phenyl]-1H-pyrazol-4-yl}ethanesulfonamide;

N-{5-amino-3-cyano-1-[2,6-dichloro-4-(trifluoromethyl)phenyl]-1H-pyrazol-4-yl}-N,N-dimethylsulfamide;

N-{5-amino-3-cyano-1-[2,6-dichloro-4-(trifluoromethyl)phenyl]-1H-pyrazol-4-yl}-1-phenylmethanesulfonamide;

N-{5-amino-3-cyano-1-[2,6-dichloro-4-(trifluoromethyl)phenyl]-1H-pyrazol-4-yl}-2,2,2-trifluoroethanesulfonamide;

(E)-N-{5-amino-3-cyano-1-[2,6-dichloro-4-(trifluoromethyl)phenyl]-1H-pyrazol-4-yl}-2-phenylethylenesulfonamide;

N-{5-amino-3-cyano-1-[2,6-dichloro-4-(trifluoromethyl)phenyl]-1H-pyrazol-4-yl}propane-1-sulfonamide;

N-[5-amino-1-[2,6-dichloro-4-pentafluorothiophenyl]-3-(trifluoromethyl)-1H-pyrazol-4-yl]-N-(methylsulfonyl)methanesulfonamide;

N-[5-amino-1-[2,6-dichloro-4-pentafluorothiophenyl]-3-(trifluoromethyl)-1H-pyrazol-4-yl]methanesulfonamide;

5-amino-1-[2,6-dichloro-4-(trifluoromethyl)phenyl]-4-(1,1-dioxidoisothiazolidin-2-yl)-1H-pyrazole-3-carbonitrile;

N-{5-amino-3-cyano-1-[2,6-dichloro-4-(trifluoromethyl)phenyl]-1H-pyrazol-4-yl}-1,1,1-trifluoro-N-methylmethanesulfonamide;

N-{5-amino-3-cyano-1-[2,6-dichloro-4-(trifluoromethyl)phenyl]-1H-pyrazol-4-yl}-N-(cyclopropylmethyl)-1,1,1-trifluoromethanesulfonamide;

N-{5-amino-3-cyano-1-[2,6-dichloro-4-(trifluoromethyl)phenyl]-1H-pyrazol-4-yl}-N-ethylmethanesulfonamide;

N-{5-amino-3-cyano-1-[2,6-dichloro-4-(trifluoromethyl)phenyl]-1H-pyrazol-4-yl}-N-cyclobutylmethanesulfonamide;

N-{5-amino-3-cyano-1-[2,6-dichloro-4-(trifluoromethyl)phenyl]-1H-pyrazol-4-yl}-N-cyclopentylmethanesulfonamide;

N-{5-amino-3-cyano-1-[2,6-dichloro-4-(trifluoromethyl)phenyl]-1H-pyrazol-4-yl}-N-(2,2,2-trifluoroethyl)methanesulfonamide;

N-{5-amino-3-cyano-1-[2,6-dichloro-4-(trifluoromethyl)phenyl]-1H-pyrazol-4-yl}-1,1,1-trifluoro-N-(methylsulfonyl)methanesulfonamide;

N-{5-amino-3-cyano-1-[2,6-dichloro-4-(trifluoromethyl)phenyl]-1H-pyrazol-4-yl}-N-[(methylsulfonyl)methyl]methanesulfonamide;

N-{5-amino-3-cyano-1-[2,6-dichloro-4-(trifluoromethyl)phenyl]-1H-pyrazol-4-yl}-N-cyclobutyl-1,1,1-trifluoromethanesulfonamide;

N-{5-amino-3-cyano-1-[2,6-dichloro-4-(trifluoromethyl)phenyl]-1H-pyrazol-4-yl}-1,1,1-trifluoro-N-isopropyl methanesulfonamide;

N-{5-amino-3-cyano-1-[2,6-dichloro-4-(trifluoromethyl)phenyl]-1H-pyrazol-4-yl}-N-cyclopentyl-1,1,1-trifluoromethanesulfonamide;

N-{5-amino-3-cyano-1-[2,6-dichloro-4-(trifluoromethyl)phenyl]-1H-pyrazol-4-yl}propane-2-sulfonamide;

N-{5-amino-3-cyano-1-[2,6-dichloro-4-pentafluorothiophenyl]-1H-pyrazol-4-yl}-N-(methylsulfonyl)methanesulfonamide;

N-{3-cyano-1-[2,6-dichloro-4-(trifluoromethyl)phenyl]-1H-pyrazol-4-yl}-1,1,1-trifluoro-N-methylmethanesulfonamide;

N-{3-cyano-1-[2,6-dichloro-4-(trifluoromethyl)phenyl]-1H-pyrazol-4-yl}-N-(methylsulfonyl)methanesulfonamide;

N-{3-cyano-1-[2,6-dichloro-4-(trifluoromethyl)phenyl]-1H-pyrazol-4-yl}-N-[(5-methylisoxazol-3-yl)methyl]methanesulfonamide;

N-{3-cyano-1-[2,6-dichloro-4-(trifluoromethyl)phenyl]-1H-pyrazol-4-yl}-2,2,2-trifluoroethanesulfonamide;

N-{3-cyano-1-[2,6-dichloro-4-(trifluoromethyl)phenyl]-1H-pyrazol-4-yl}-2,2,2-trifluoro-N-(methylsulfonyl)ethanesulfonamide;

N-{3-cyano-1-[2,6-dichloro-4-(trifluoromethyl)phenyl]-1H-pyrazol-4-yl}-N-{[1-(trifluoromethyl)cyclopropyl]methyl}methanesulfonamide;

N-{3-cyano-1-[2,6-dichloro-4-pentafluorothiophenyl]-1H-pyrazol-4-yl}-N-(methylsulfonyl)methanesulfonamide;

N-{3-cyano-1-[2,6-dichloro-4-(trifluoromethyl)phenyl]-1H-pyrazol-4-yl}methanesulfonamide;

N-{3-cyano-1-[2,6-dichloro-4-(trifluoromethyl)phenyl]-1H-pyrazol-4-yl}-N-(2,2,2-trifluoroethyl)methanesulfonamide;

N-{5-amino-3-cyano-1-[2,6-dichloro-4-(trifluoromethoxy)phenyl]-1H-pyrazol-4-yl}-N-(2,2,2-trifluoroethyl)methanesulfonamide;

N-{5-amino-3-cyano-1-[2,6-dichloro-4-pentafluorothiophenyl]-1H-pyrazol-4-yl}-N-(2,2,2-trifluoroethyl)methanesulfonamide;

N-{5-amino-3-cyano-1-[2,6-dichloro-4-pentafluorothiophenyl]-1H-pyrazol-4-yl}-2,2,2-trifluoro-N-(methylsulfonyl)methanesulfonamide;

N-{5-amino-3-cyano-1-[2,6-dichloro-4-(trifluoromethyl)phenyl]-1H-pyrazol-4-yl}-N-(2,2-difluorocyclopropyl)methanesulfonamide;

N-{5-amino-3-cyano-1-[2,6-dichloro-4-pentafluorothiophenyl]-1H-pyrazol-4-yl}-N-[2-(1H-1,2,4-triazol-1-yl)ethyl]methanesulfonamide;

N-{5-amino-3-cyano-1-[2,6-dichloro-4-pentafluorothiophenyl]-1H-pyrazol-4-yl}-1,1,1-trifluoromethanesulfonamide;

5-amino-1-[2,6-dichloro-4-pentafluorothiophenyl]-4-(1,1-dioxidoisothiazolidin-2-yl)-1H-pyrazole-3-carbonitrile;

N-{5-amino-3-cyano-1-[2,6-dichloro-4-(trifluoromethyl)phenyl]-1H-pyrazol-4-yl}-N-[(1-methylcyclopropyl)methyl]methanesulfonamide;

5-amino-4-[bis(methylsulfonyl)amino]-1-[2,6-dichloro-4-pentafluorothiophenyl]-1H-pyrazole-3-carboxamide;

N-{5-amino-3-cyano-1-[2,6-dichloro-4-(trifluoromethoxy)phenyl]-1H-pyrazol-4-yl}-N-(methylsulfonyl)methanesulfonamide;

N-(5-amino-3-cyano-1-{2,6-dichloro-4-[(trifluoromethyl)thio]phenyl}-1H-pyrazol-4-yl)-N-(methylsulfonyl)methanesulfonamide;

N-{3-acetyl-5-amino-1-[2,6-dichloro-4-pentafluorothiophenyl]-1H-pyrazol-4-yl}-N-(methylsulfonyl)methanesulfonamide;

N-(5-amino-3-cyano-1-{2,6-dichloro-4-[(trifluoromethyl)thio]phenyl}-1H-pyrazol-4-yl)methanesulfonamide;

N-(5-amino-3-cyano-1-{2,6-dichloro-4-[(trifluoromethyl)thio]phenyl}-1H-pyrazol-4-yl)-N-(2,2,2-trifluoroethyl)methanesulfonamide;

N-{5-amino-3-cyano-1-[2,6-dichloro-4-(difluoromethoxy)phenyl]-1H-pyrazol-4-yl}-N-(methylsulfonyl)methanesulfonamide;

N-{5-amino-3-cyano-1-[2,6-dichloro-4-pentafluorothiophenyl]-1H-pyrazol-4-yl}methanesulfonamide;

N-{5-amino-3-cyano-1-[2,6-dichloro-4-pentafluorothiophenyl]-1H-pyrazol-4-yl}-N-{[1-(trifluoromethyl)cyclopropyl]methyl}methanesulfonamide;

N-{5-amino-3-cyano-1-[2,6-dichloro-4-pentafluorothiophenyl]-1H-pyrazol-4-yl}-N-(methylsulfonyl)ethanesulfonamide;

methyl 5-amino-3-cyano-1-[2,6-dichloro-4-(trifluoromethyl)phenyl]-1H-pyrazol-4-yl(methylsulfonyl)carbamate;

N-{5-amino-3-cyano-1-[2,6-dichloro-4-pentafluorothiophenyl]-1H-pyrazol-4-yl}-N-methylmethanesulfonamide;

N-{5-amino-3-cyano-1-[2,6-dichloro-4-pentafluorothiophenyl]-1H-pyrazol-4-yl}-N-(2-fluoroethyl)methanesulfonamide;

N-{5-amino-3-cyano-1-[2,6-dichloro-4-pentafluorothiophenyl]-1H-pyrazol-4-yl}-N-[(3-methylisoxazol-5-yl)methyl]methanesulfonamide;

N-{5-amino-3-cyano-1-[2,6-dichloro-4-pentafluorothiophenyl]-1H-pyrazol-4-yl}-N-(pyridin-2-ylmethyl)methanesulfonamide;

N-{5-amino-3-cyano-1-[2,6-dichloro-4-pentafluorothiophenyl]-1H-pyrazol-4-yl}-N-(pyridin-4-ylmethyl)methanesulfonamide;

N-{5-amino-3-cyano-1-[2,6-dichloro-4-pentafluorothiophenyl]-1H-pyrazol-4-yl}-N-(1,2,4-oxadiazol-3-ylmethyl)methanesulfonamide;

$N^2$-{5-amino-3-cyano-1-[2,6-dichloro-4-pentafluorothiophenyl]-1H-pyrazol-4-yl}-$N^2$-(methylsulfonyl)glycinamide;

N-{5-amino-3-cyano-1-[2,6-dichloro-4-pentafluorothiophenyl]-1H-pyrazol-4-yl}-N-isopropylmethanesulfonamide;

N-{5-amino-3-cyano-1-[2,6-dichloro-4-pentafluorothiophenyl]-1H-pyrazol-4-yl}-N-(pyridin-3-ylmethyl)methanesulfonamide;

N-{5-amino-3-cyano-1-[2,6-dichloro-4-pentafluorothiophenyl]-1H-pyrazol-4-yl}-N-(1H-1-pyrazol-3-ylmethyl)methanesulfonamide;

N-{5-amino-3-cyano-1-[2,6-dichloro-4-pentafluorothiophenyl]-1H-pyrazol-4-yl}-N-(2,2,3,3,3-pentafluoropropyl)methanesulfonamide;

N-{5-amino-3-cyano-1-[2,6-dichloro-4-pentafluorothiophenyl]-1H-pyrazol-4-yl}-N-(2-pyrrolidin-1-ylethyl)methanesulfonamide;

N-{5-amino-3-cyano-1-[2,6-dichloro-4-pentafluorothiophenyl]-1H-pyrazol-4-yl}-N-(2-morpholin-4-ylethyl)methanesulfonamide;

N-{5-amino-3-cyano-1-[2,6-dichloro-4-(trifluoromethyl)phenyl]-1H-pyrazol-4-yl}-N-methylethanesulfonamide;

N-{5-amino-3-cyano-1-[2,6-dichloro-4-(trifluoromethyl)phenyl]-1H-pyrazol-4-yl}-N-methylpropane-1-sulfonamide;

N-{5-amino-3-cyano-1-[2,6-dichloro-4-(trifluoromethyl)phenyl]-1H-pyrazol-4-yl}-N-methylcyclopropanesulfonamide;

N-{5-amino-3-cyano-1-[2,6-dichloro-4-(trifluoromethyl)phenyl]-1H-pyrazol-4-yl}-2,2,2-trifluoro-N-methylethanesulfonamide;

N-{5-amino-3-cyano-1-[2,6-dichloro-4-pentafluorothiophenyl]-1H-pyrazol-4-yl}-N-[(1-methyl-1H-imidazol-2-yl)methyl]methanesulfonamide;

N-{5-amino-3-cyano-1-[2,6-dichloro-4-pentafluorothiophenyl]-1H-pyrazol-4-yl}-N-[(5-methylisoxazol-3-yl)methyl]methanesulfonamide;

[{5-amino-3-cyano-1-[2,6-dichloro-4-pentafluorothiophenyl]-1H-pyrazol-4-yl}(methylsulfonyl)amino]methyl pivalate;

N-{5-amino-3-cyano-1-[2,6-dichloro-4-pentafluorothiophenyl]-1H-pyrazol-4-yl}-N-ethylmethanesulfonamide;

N-{5-amino-3-cyano-1-[2,6-dichloro-4-pentafluorothiophenyl]-1H-pyrazol-4-yl}-N-benzylmethanesulfonamide;

N-{5-amino-3-cyano-1-[2,6-dichloro-4-pentafluorothiophenyl]-1H-pyrazol-4-yl}-N-(4-fluorobenzyl)methanesulfonamide;

N-{5-amino-3-cyano-1-[2,6-dichloro-4-(trifluoromethyl)phenyl]-1H-pyrazol-4-yl}-1-(methylsulfonyl)ethanesulfonamide;

N-{5-amino-1-[2-chloro-4-pentafluorothio-phenyl]-3-cyano-1H-pyrazol-4-yl}-N-(methylsulfonyl)methanesulfonamide;

5-amino-1-[2,6-dichloro-4-pentafluorothiophenyl]-4-(1,1-dioxido-1,2-thiazinan-2-yl)-1H-pyrazole-3-carbonitrile;

N-{5-(benzylamino)-3-cyano-1-[2,6-dichloro-4-pentafluorothiophenyl]-1H-pyrazol-4-yl}-N-(methylsulfonyl)methanesulfonamide;

N-{3-cyano-1-[2,6-dichloro-4-pentafluorothiophenyl]-5-[(ethoxymethyl)amino]-1H-pyrazol-4-yl}-N-(methylsulfonyl)methanesulfonamide;

N-{3-cyano-1-[2,6-dichloro-4-pentafluorothiophenyl]-5-(methylamino)-1H-pyrazol-4-yl}methanesulfonamide;

N-{3-cyano-1-[2,6-dichloro-4-pentafluorothiophenyl]-4-[(methylsulfonyl)(2,2,2-trifluoroethyl)amino]-1H-pyrazol-5-yl}-2-methoxyacetamide;

ethyl 4-[bis(methylsulfonyl)amino]-3-cyano-1-[2,6-dichloro-4-pentafluorothiophenyl]-1H-pyrazol-5-ylimidoformate;

N-{3-cyano-5-[(cyclopropylmethyl)amino]-1-[2,6-dichloro-4-pentafluorothiophenyl]-1H-pyrazol-4-yl}methanesulfonamide;

N-{3-cyano-1-[2,6-dichloro-4-pentafluorothiophenyl]-4-[(methylsulfonyl)(2,2,2-trifluoroethyl)amino]-1H-pyrazol-5-yl}acetamide;

N-{3-cyano-1-[2,6-dichloro-4-pentafluorothiophenyl]-5-methoxy-1H-pyrazol-4-yl}methanesulfonamide;

N-[3-cyano-1-[2,6-dichloro-4-(trifluoromethyl)phenyl]-5-(methylamino)-1H-pyrazol-4-yl]-N-(methylsulfonyl)methanesulfonamide;

N-(3-cyano-1-[2,6-dichloro-4-pentafluorothiophenyl]-5-{[(dimethylamino)methylene]amino}-1H-pyrazol-4-yl)-N-(methylsulfonyl)methanesulfonamide;

N-(3-cyano-1-[2,6-dichloro-4-pentafluorothiophenyl]-5-{[2-(dimethylamino)ethyl]amino}-1H-pyrazol-4-yl)-N-(methylsulfonyl)methanesulfonamide;

N-{5-amino-3-cyano-1-[2,6-dichloro-4-pentafluorothiophenyl]-1H-pyrazol-4-yl}-N, (2,2,2-trifluoroethylsulfonyl)-2,2,2-trifluoroethanesulfonamide;

N-{3-cyano-1-[2,6-dichloro-4-pentafluorothiophenyl]-5-[(2-pyrrolidin-1-ylethyl)amino]-1H-pyrazol-4-yl}-N-(methylsulfonyl)methanesulfonamide;

N-{3-cyano-1-[2,6-dichloro-4-pentafluorothiophenyl]-5-[(2-morpholin-4-ylethyl)amino]-1H-pyrazol-4-yl}-N-(methylsulfonyl)methanesulfonamide;

N-{3-cyano-1-[2,6-dichloro-4-pentafluorothiophenyl]-5-[(2-piperidin-1-ylethyl)amino]-1H-pyrazol-4-yl}-N-(methylsulfonyl)methanesulfonamide;

N-[3-cyano-1-[2,6-dichloro-4-pentafluorothiophenyl]-5-(methylamino)-1H-pyrazol-4-yl]-N-(methylsulfonyl)methanesulfonamide;

N-{3-cyano-5-[(cyclopropylmethyl)amino]-1-[2,6-dichloro-4-pentafluorothiophenyl]-1H-pyrazol-4-yl}-N-(methylsulfonyl)methanesulfonamide;

N-{5-amino-3-cyclopropyl-1-[2,6-dichloro-4-pentafluorothiophenyl]-1H-pyrazol-4-yl}-N-(methylsulfonyl)methanesulfonamide;

N-{5-amino-1-[2,6-dichloro-4-pentafluorothiophenyl]-1H-pyrazol-4-yl}methanesulfonamide;

N-{3-cyano-1-[2,6-dichloro-4-pentafluorothiophenyl]-5-[(pyridin-4-ylmethyl)amino]-1H-pyrazol-4-yl}methanesulfonamide;

N-{5-amino-3-cyano-1-[2,6-dichloro-4-pentafluorothiophenyl]-1H-pyrazol-4-yl}-N-(aminosulfonyl)methanesulfonamide;

tert-butyl ({5-amino-3-cyano-1-[2,6-dichloro-4-pentafluorothiophenyl]-1H-pyrazol-4-yl}amino)sulfonylcarbamate;

N-{5-amino-3-cyano-1-[2,6-dichloro-4-pentafluorothiophenyl]-1H-pyrazol-4-yl}-N-(2-pyridin-4-ylethyl)methanesulfonamide;

N-{5-amino-3-cyano-1-[2,6-dichloro-4-pentafluorothiophenyl]-1H-pyrazol-4-yl}-N-(pyrazin-2-ylmethyl)methanesulfonamide;

N-{5-amino-3-cyano-1-[2,6-dichloro-4-pentafluorothiophenyl]-1H-pyrazol-4-yl}-N-[(6-aminopyridin-3-yl)methyl]methanesulfonamide;

N-{5-amino-3-cyano-1-[2,6-dichloro-4-pentafluorothiophenyl]-1H-pyrazol-4-yl}-N-(pyrimidin-4-ylmethyl)methanesulfonamide;

N-{5-amino-3-cyano-1-[2,6-dichloro-4-pentafluorothiophenyl]-1H-pyrazol-4-yl}-N-(1-pyridin-4-ylethyl)methanesulfonamide;

N-{3-cyano-1-[2,6-dichloro-4-pentafluorothiophenyl]-1H-pyrazol-4-yl}-2-oxo-N-(2,2,2-trifluoroethyl)propane-1-sulfonamide;

N-(3-cyano-1-[2,6-dichloro-4-pentafluorothiophenyl]-5-{[3-(dimethylamino)propyl]amino}-1H-pyrazol-4-yl)-N-(2,2,2-trifluoroethyl)methanesulfonamide;

N-{3-cyano-1-[2,6-dichloro-4-pentafluorothiophenyl]-5-[(2-piperidin-1-ylethyl)amino]-1H-pyrazol-4-yl}-N-(2,2,2-trifluoroethyl)methanesulfonamide;

N-{5-amino-3-cyano-1-[2,6-dichloro-4-pentafluorothiophenyl]-1H-pyrazol-4-yl}-N-(2,2,2-trifluoroethyl)sulfamide;

N-{5-amino-3-cyano-1-[2,6-dichloro-4-pentafluorothiophenyl]-1H-pyrazol-4-yl}sulfamide;

N-{5-amino-3-cyano-1-[2,6-dichloro-4-(trifluoromethyl)phenyl]-1H-pyrazol-4-yl}-4-fluoro-N-(methylsulfonyl)benzenesulfonamide;

N-{5-amino-3-cyano-1-[2,6-dichloro-4-(trifluoromethyl)phenyl]-1H-pyrazol-4-yl}-2,4-difluoro-N-(methylsulfonyl)benzenesulfonamide;

methyl 3-cyano-1-[2,6-dichloro-4-pentafluorothiophenyl]-4-[(methylsulfonyl)(2,2,2-trifluoroethyl)amino]-1H-pyrazol-5-ylcarbamate;

2,2,2-trifluoroethyl 3-cyano-1-[2,6-dichloro-4-pentafluorothiophenyl]-4-[(methylsulfonyl)(2,2,2-trifluoroethyl)amino]-1H-pyrazol-5-ylcarbamate;

N-{5-({[(2-aminoethyl)amino]carbonyl}amino)-3-cyano-1-[2,6-dichloro-4-pentafluorothiophenyl]-1H-pyrazol-4-yl}-N-(2,2,2-trifluoroethyl)methanesulfonamide;

trifluoroacetate salt of N-{5-[(2-azetidin-1-ylethyl)amino]-3-cyano-1-[2,6-dichloro-4-pentafluorothiophenyl]-1H-pyrazol-4-yl}-N-(2,2,2-trifluoroethyl)methanesulfonamide;

N-(3-cyano-1-[2,6-dichloro-4-pentafluorothiophenyl]-5-{[(2,4-dihydroxyphenyl)methylene]amino}-1H-pyrazol-4-yl)-N-(2,2,2-trifluoroethyl)methanesulfonamide;

N-(3-cyano-1-[2,6-dichloro-4-pentafluorothiophenyl]-5-{[phenylmethylene]amino}-1H-pyrazol-4-yl)-N-(2,2,2-trifluoroethyl)methanesulfonamide;

N-{5-chloro-3-cyano-1-[2,6-dichloro-4-pentafluorothiophenyl]-1H-pyrazol-4-yl}-N-(2,2,2-trifluoroethyl)methanesulfonamide; or N-(3-cyano-1-[2,6-dichloro-4-pentafluorothiophenyl]-5-{[3-(dimethylamino)ethyl]amino}-1H-pyrazol-4-yl)-N-(methylsulfonyl)methanesulfonamide;

or a pharmaceutically, veterinarily or agriculturally acceptable salt or solvate thereof.

Compounds of formula (I) possess parasiticidal activity in humans, animals and agriculture. They are particularly useful in the control of ectoparasites.

In a further aspect, the present invention provides a process for the preparation of a compound of formula (I), or a pharmaceutically, veterinarily or agriculturally acceptable salt thereof, or a pharmaceutically, veterinarily, or agriculturally acceptable solvate (including hydrate) of either entity, as illustrated below.

The following processes are illustrative of the general synthetic procedures which may be adopted in order to obtain the compounds of the invention.

When one or more of $R^1$, $R^2$, $R^3$, $R^4$ and $R^5$ contain reactive functional groups then additional protection may be provided according to standard procedures during the synthesis of compounds of formula (I). In the processes described below, for all synthetic precursors used in the synthesis of compounds of formula (I), the definitions of $R^1$, $R^2$, $R^3$, $R^4$, and $R^5$, wherein $R^1$, $R^2$, $R^3$, $R^4$, and $R^5$ are as defined for formula (I), are intended to optionally include suitably protected variants, $P^1$, $P^2$, $P^3$, $P^4$ and $P^5$. Such suitable protecting groups for these functionalities are described in the references listed below and the use of these protecting groups where needed is specifically intended to fall within the scope of the processes described in the present invention for producing compounds of formula (I) and its precursors. When suitable protecting groups are used, then these will need to be removed to yield compounds of formula (I). Deprotection can be effected according to standard procedures including those described in the references listed below.

For example, when $R^5$ in formula (I) is an unsubstituted amino group, certain precursors may require protection of the amino group in order to perform the necessary transformations, for example, by an imidoformamide group such as a compound of formula (Ib), where $R^1$-$R^4$ are as described for formula (I) and $R^5$ represents —N=C(H)—NR$^a$R$^b$, where $R^a$ and $R^b$ independently represent $C_{1-6}$alkyl, e.g. to form a N,N-dimethyl group. Such imidoformamides may be prepared by methods herein described and may be removed under suitable acid conditions, such as at elevated with a suitable acid such as hydrochloric acid or para-toluenesulfonic acid in a solvent such as methanol or dioxane.

According to a first general method, a compound of formula (I), in which $R^4$ is H and $R^1$, $R^2$, $R^3$ and $R^5$ are as previously defined for formula (I), may be prepared from a compound of formula (II):

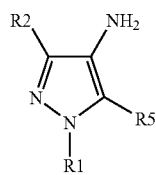

(II)

wherein $R^1$, $R^2$ and $R^5$ are as previously defined for formula (I) by sulfonation by a suitable sulfonating agent, e.g. $R^3SO_2Cl$ or a sulfonic acid anhydride under standard conditions, e.g. in a suitable solvent, for example, dichloromethane, in the presence of base, typically pyridine/4-dimethylaminopyridine mixtures, under an inert atmosphere.

Compounds of formula (I) where $R^4$ is not hydrogen may be prepared from compounds of formula (I) where $R^4$ is hydrogen by standard procedures. For example, a compound of formula (I) where $R^4$ is $R^9SO_2$— may be prepared by the addition of a suitable sulfonating agent, e.g. $R^9SO_2Cl$, to a solution of a compound of formula (I) in an aprotic solvent, e.g. acetonitrile or dichloromethane, in the presence of base, e.g., triethylamine, potassium carbonate or pyridine/4-dimethylaminopyridine mixtures.

Compounds of formula (II) may be bis-sulfonated in a one pot process, under well-known conditions, to form compounds of formula (I).

A compound of formula (I) where $R^4$ and $R^3$ are taken together with the nitrogen and sulphur atoms to which they are attached to form a 4 to 7-membered monosulfonamide ring, may be prepared from a compound of formula (II), by the single step addition of a chloro-$C_{1-6}$alkylsulfonyl chloride to a solution of a compound of formula (II) in a suitable solvent, such as pyridine, allowing the reaction to progress then subsequently adding a mild base, typically potassium carbonate in a suitable solvent, such as N,N-dimethylformamide and heating at elevated temperatures for several hours.

A compound of formula (I) where $R^4$ is $SO_2R^9$ and $R^9$ and $R^3$ are taken together with the nitrogen and sulphur atoms to which they are attached to form a 4 to 7-membered bis-sulfonamide ring, may be prepared from a compound of formula (II) by the two step addition of a $C_{1-6}$ alkyl bis-sulfonyl chloride to a solution of a compound of formula (II) in a suitable solvent, such as pyridine, and heating at reflux for several hours, typically overnight.

Compounds of formula (I) where $R^4$ is an alkyl group may be prepared, for example, by reaction of the compound of formula (I) with a suitable alkylating agent, e.g. $R^4$—X, where X may be any leaving group, typically I, Br, Cl, OTs, OTf, O-mesylate, or O-trichloromethylsulphonate, in a suitable solvent, e.g. acetone, dichloromethane, acetonitrile, dimethylformamide or N-methylpyrrolidinone, in the presence of base, e.g. potassium carbonate, caesium carbonate, and sodium hydride. Other salts may aid the reaction, for example, sodium iodide or potassium iodide.

A compound of formula (I) in which $R^4$ is an alkyl group, may be prepared by alkylation of a compound of formula (I) where $R^4$ is hydrogen, using suitably acidic alcohol reagents via a Mitsunobu reaction.

A compound of formula (I) in which $R^4$ is $C_{1-6}$ alkoxycarbonyl may be prepared by acylation of a compound of formula (I), where $R^4$ is H, with an alkylhaloformate, e.g. a chloroformate, in a suitable solvent, such as acetone at reflux temperature for several hours using a suitable base such as potassium carbonate.

Standard chemical procedures may be used to modify sidechains $R^2$, $R^3$, $R^4$ and $R^5$ of compounds of formula (I) provided that any reactive functional groups in the remaining sidechains are appropriately protected, as hereinbefore mentioned.

For example, a compound of formula (I) in which $R^2$ is CN may be converted to a compound of formula (I) where $R^2$ is —C(O)N(R$^a$)R$^b$ and $C_{1-6}$ alkanoyl under standard conditions well-known to those skilled in the art.

Compounds of formula (I) where $R^4$ is —($C_{0-3}$alkylene)-cyclopropyl may be prepared from compounds of formula (I) where $R^4$ is the corresponding alkenyl by standard cyclopropanation procedures, e.g. conversion of an ethenyl derivative to the corresponding difluorocyclopropyl derivative by heating a solution in a suitable solvent such as toluene with methyl benzoate at elevated temperature followed by addition of trimethylsilyl-2,2-difluoro-2-(fluorosulfonyl)acetate dropwise over several hours. Such transformations are also described in WO98/24767.

Compounds of formula (I), where $R^4$ is an $C_{2-6}$ alkenyl may be prepared from the corresponding bromoalkyl compound by dehydrobromination under standard conditions. Also, compounds of formula (I), where $R^4$ is a bromoalkyl group can also be used to prepare other compounds of formula (I) where the bromo-group is displaced with a suitable nucleophile e.g. a heteroaryl, in a suitable polar solvent, in the presence of a suitable base.

Compounds of formula (I) where $R^4$ is a readily oxidisable group, can be used to prepare alternative compounds of formula (I), e.g. conversion of thioethers and hydroxyl substituted alkyl substituents to sulphones and carbonyl derivatives respectively, using standard oxidising agents, such as oxone or those described in "Handbook of Reagents for Organic Synthesis—Oxidising and Reducing Agents" edited by S. D. Burke and R. L. Danheiser.

Compounds of formula (I) where $R^4$ is an alkyl group containing an aldehyde or ketone group can be prepared by oxidation of the corresponding hydroxyalkyl group under standard conditions, such as Dess-Martin periodinane in an aprotic solvent, such as dichloromethane. The resulting aldehyde or ketone groups can be further treated with nucleophilic reagents, in a suitable solvent, typically tetrahydrofuran, and optionally in the presence of a suitable catalyst, to give the nucleophilically substituted secondary or tertiary alcohol.

Additionally, compounds of formula (I) in which $R^4$ is —($C_{1-3}$alkylene)-$CO_2H$ may be prepared by saponification of the corresponding carboxylic acid ester.

A compound of formula (I) in which $R^5$ is $NH_2$, may be used to prepare an alternative compound of formula (I) by derivatisation of the amino group, including methods as discussed above for formation of $R^4$ groups, e.g. alkylation or acylation. Additionally, a compound of formula (I) where $R^5$ represents an optionally substituted $C_{1-6}$ alkylimino group, may be prepared by heating the corresponding compound of formula (I) where $R^5$ represents $NH_2$ with an akdehyde, at elevated temperature, with a suitable catalyst, typically p-toluenesulfonic acid, with the optional addition of molecular sieves. A compound of formula (I) where $R^5$ represents an optionally substituted $C_{1-6}$ alkylimino group may be used to form a different compound of formula (I) by reduction of the imine bond by a suitable reducing agent, for example, sodium borohydride, in a suitable solvent, typically ethanol.

Compounds of formula (I) where $R^5$ is a derivatised amino group can be further manipulated depending on the desired derivatisation. For example N-alkenyl derivatives may be oxidatively cleaved to produce aldehydes under standard conditions. Such aldehyde derivatives may be further manipulated to give other derivatives, e.g. reductive amination under standard conditions to give secondary and tertiary amines.

Also, reaction of compounds of formula (I) in which $R^5$ is $NH_2$, with an acid chloride or an acid anhydride in an aprotic solvent, such as acetonitrile at reflux overnight, produces a compound of formula (I) in which $R^5$ is —$NHR^{13}$ and $R^{13}$ represents an optionally substituted $C_{1-6}$ alkanoyl or $C_{1-6}$ alkoxycarbonyl group. Alternatively, the reaction may take place coupling a carboxylic acid with an amine in the presence of a suitable coupling agent such as a water-soluble carbodiimide.

A compound of formula (I) in which $R^5$ is $NH_2$, can undergo reaction with a tri-alkyl orthoformate, e.g. triethyl orthoformate, in acidic conditions, by heating at elevated temperatures, typically 60° C., for several hours, typically 2 to 4 hours, to give compounds of formula (I) in which $R^5$ is a methylimino group, substituted by an optionally substituted $C_{1-6}$ alkoxy group, e.g. ethoxy. These imino-ethers can be refluxed with primary or secondary amines optionally in a suitable solvent to give other compounds of formula (I) wherein $R^5$ is a methylimino group, substituted by a di-$C_{1-6}$ alkyl amino group, e.g. dimethylamino.

A compound of formula (I) in which $R^5$ is H, may be prepared by the diazotisation of a compound of formula (I) in which $R^5$ is $NH_2$ by a variety of standard diazotisation procedures.

Compounds of formula (I) in which $R^5$ is $NH_2$, can be converted to give a compound of formula (I) wherein $R^5$ is halo, utilising standard Sandmeyer reaction conditions.

Compounds of formula (I) in which $R^5$ is $NH_2$ can also be converted to carbamates or ureas under standard conditions. Halo-substituted carbamates may be further reacted with nucleophiles such as primary or secondary amines in a suitable alcoholic solvent, optionally with the addition of lithium iodide and allowing to stir at room temperature for several hours, to give the nucleophilically substituted product e.g. a secondary or tertiary amine substituted derivative.

A compound of formula (II) may be prepared as shown in Scheme 1 below, wherein $R^1$, $R^2$ and $R^5$ are as previously defined, the —$CO_2Me$ group is illustrative of any carboxylic acid ester group and the —$CO_2(CH_2)_2Si(CH_3)_2$ is illustrative of any suitable amino protecting group resulting from the Curtius rearrangement.

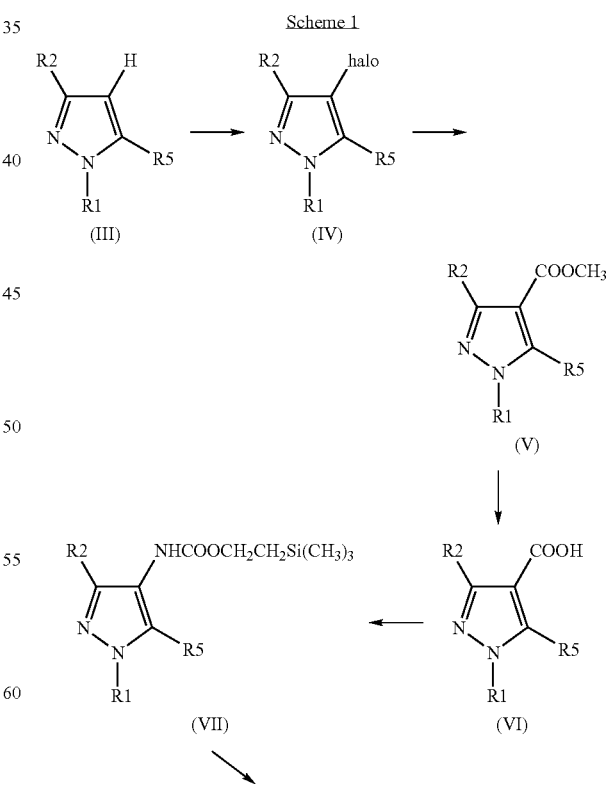

Scheme 1

-continued

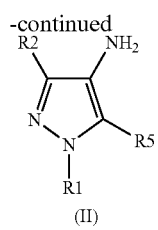

(II)

A compound of formula (IV) may be obtained from a compound of formula (III) by conventional halogenation procedures, e.g. treatment of N-iodosuccinimide in a suitable solvent such as acetonitrile to give the iodo compound. A compound of formula (IV) may be carbonylated using conventional procedures to give a compound of formula (V), e.g., using a palladium catalyst. Saponification of the methyl ester, of formula (V), to give the acid, of formula (VI), may be achieved using standard ester hydrolysis conditions. A compound of formula (VII) may be prepared from a compound of formula (VI) by the Curtius rearrangement of the acyl azide prepared in situ by conventional procedures, e.g., diphenylphosphoryl azide is added dropwise to a solution of a compound of formula (VI), triethylamine and 2-(trimethylsilyl)ethanol in 1,4-dioxane at elevated temperature. Deprotection to yield the amine of formula (II) may be effected using a variety of fluoride induced desilylation procedures, such as heating a solution of a compound of formula (VII) and tetrabutylammonium fluoride in a suitable solvent, typically tetrahydrofuran, at elevated temperatures.

An alternative route to compounds of formula (II) is via nitration of compounds of formula (III) to give nitro compounds of formula (VIII) followed by reduction of the nitro substituent of compounds of formula (VIII) to the amines of formula (II) as shown in Scheme 2, wherein $R^1$, $R^2$ and $R^5$ are as previously defined for compounds of formula (I).

Scheme 2

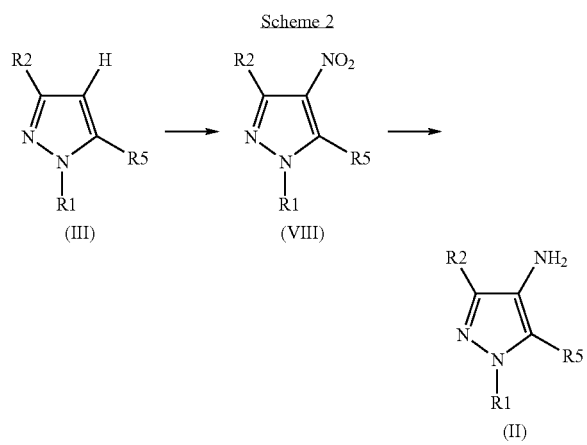

The preparation of compounds of formula (VIII), wherein $R^1$, $R^2$ and $R^5$ are as previously defined for formula (I), may be effected by conventional electrophilic nitration procedures, then reduction of compounds of formula (VIII) may be facilitated by a variety of reducing agents including those described in "Handbook of Reagents for Organic Synthesis—Oxidising and Reducing Agents" edited by S. D. Burke and R. L. Danheiser.

Compounds of formula (III) and (VIII) are useful compounds to undergo functional group interconversion at, for example, position $R^5$ to give different groups of formula (VIII) using transformations herein described and obvious to those skilled in the art.

The preparation of a compound of formula (III) may be achieved by the reduction of a compound of formula (IV), wherein halo is iodo, e.g. by transmetallation with a suitable organometallic reagent such as a Grignard reagent, typically isopropylmagnesium chloride, in a suitable solvent such as tetrahydrofuran at reduced temperature, under suitable aqueous work-up conditions.

Synthesis of the arylpyrazole template can be readily performed.

A compound of formula (III) wherein $R^2$ is $C_{1-6}$ alkyl optionally substituted by halo or $C_{3-8}$ cycloalkyl may be prepared from a hydrazine of formula (IX) by reaction with a α-cyanoketone of formula (X)

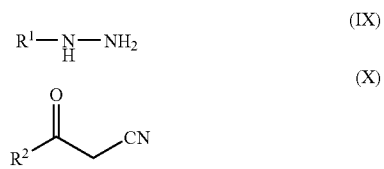

wherein $R^2$ represents $C_{1-6}$ alkyl optionally substituted by halo or $C_{3-8}$ cycloalkyl, at elevated temperatures. Compounds of formula (X) are well-known or can be prepared by methods well-known to those skilled in the art.

A compound of formula (IX) may be prepared by diazotisation of a compound of formula (XI), by reaction with sodium nitrite in an acidic mixture, for example glacial acetic acid and sulphuric acid at temperatures between 5-60° C. to give the diazonium salt of formula (XII)

followed by reduction of the diazonium salt of formula (XII) with an agent such as stannous chloride in a concentrated acid such as hydrochloric acid.

Alternatively, a compound of formula (XIII)

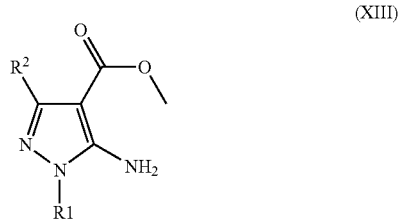

where $R^2$ represents an optionally substituted $C_{1-6}$alkyl and the methyl group is illustrative of any suitable carboxylic ester protecting group, may be prepared from a hydrazine of formula (IX) and a compound of formula (XIV)

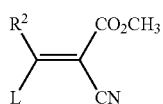

(XIV)

wherein L is a leaving group, typically Cl, in a suitable solvent, typically diethyl ether, and a suitable base such as potassium carbonate.

A compound of formula (III), wherein $R^2$ is hydrogen, $C_{1-6}$ alkyl optionally substituted by halo or $C_{3-8}$ cycloalkyl, may be prepared by reaction of a compound of formula (IX) with a compound of formula (XV),

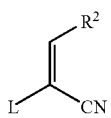

(XV)

wherein $R^2$ is hydrogen, $C_{1-6}$ alkyl optionally substituted by halo or $C_{3-8}$ cycloalkyl, and L is a leaving group such as chloro, bromo, iodo, at elevated temperatures.

A compound of formula (V) where $R^2$ represents $C_{1-6}$ alkyl, $C_{1-6}$haloalkyl, $C_{3-8}$ cycloalkyl or cyano may be prepared by reaction of a compound of formula (IX) with a compound of formula (XVI)

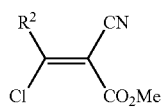

(XVI)

wherein $R^2$ represents $C_{1-6}$ alkyl, $C_{1-6}$haloalkyl, $C_{3-8}$ cycloalkyl or cyano, in aprotic solvents such as diethyl ether in the presence of a mild base such as potassium carbonate.

Chloroalkenes of formula (XVI) are obtained by chlorination of alkenes of formula (XVII) using phosphorous pentachloride in a solvent such as dichloromethane at room temperature.

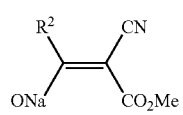

(XVII)

Functionalised alkenes of formula (XVII) may be synthesised using a wide variety of literature methodology.

Alternatively, compounds of formula (III), where $R^2$ represents CN and $R^5$ represents OH or $NH_2$ can be synthesised via the Japp-Klingemann reaction: the reaction of aryl diazonium salts of formula (IX) with compounds of formula (XVIII) or (XIX), wherein R and R" are alkyl groups.

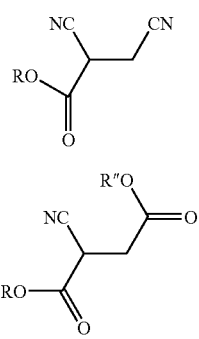

(XVIII)

(XIX)

The diazonium salts of formula (IX) are typically generated in situ, for example by the dropwise addition of a solution of the aminobenzenes of formula (VIII) in glacial acetic acid to a solution of sodium nitrite in concentrated sulphuric/ glacial acetic acid mixtures at reduced temperature, typically 10° C., followed by heating at 50° C. for several hours, typically 1 hour and allowing to cool to room temperature. This solution of the diazonium salt is then added dropwise to a solution of a compound of formula (XVIII) or (XIX) in a suitable solvent, such as acetic acid followed by stirring at room temperature for up to 1 hour. The reaction mixture is poured into water and extracted with a water immiscible organic solvent such as dichloromethane. Aqueous ammonium hydroxide is added to the organic extract and stirred overnight to give compounds of formula (III).

Compounds of formula (XIX) can be prepared by the addition of glycolonitrile to alpha-nitrile esters in a suitable solvent, in the presence of a mild base, typically, potassium carbonate, and stirred for several hours at room temperature.

An arylpyrazole compound of formula (XX),

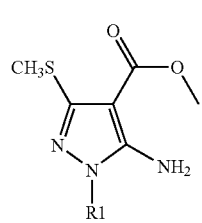

(XX)

where $R^1$ is previously defined and the methyl group is illustrative of any carboxylic acid protecting group, may be prepared by reaction of a hydrazine of formula (IX) with an electrophile such as a compound of formula (XXI)

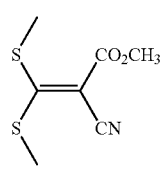

(XXI)

in an aprotic solvent, such as isopropyl alcohol, at reflux for several hours.

The synthesis of the desired 1-aminobenzenes can be achieved using standard conditions. For example, 2,6-unsubstituted aniline derivatives can be mono- or di-chlorinated by the addition of N-chlorosuccinimide in a suitable solvent, such as acetonitrile, and heating at elevated temperatures, typically 45-50° C., for several hours, typically from 1 to 3 hours.

Moreover, persons skilled in the art will be aware of variations of, and alternatives to, the processes described which allow the compounds defined by formula (I) to be obtained.

It will also be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps. It will also be appreciated that various standard substituent or functional group interconversions and transformations within certain compounds of formula (I) will provide other compounds of formula (I).

The skilled person will appreciate that the compounds of the invention could be made by methods other than those herein described, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions), "March's Advanced Organic Chemistry—Reactions, Mechanisms and Structure", M B Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis— The Disconnection Approach", S Warren (Wiley), (1982 or later editions), "Designing Organic Syntheses" S Warren (Wiley) (1983 or later editions), "Guidebook To Organic Synthesis" R K Mackie and DM Smith (Longman) (1982 or later editions), etc., and the references therein as a guide.

It is to be understood that the synthetic transformation methods mentioned herein are exemplary only and they may be carried out in various different sequences in order that the desired compounds can be efficiently assembled. The skilled chemist will exercise his judgement and skill as to the most efficient sequence of reactions for synthesis of a given target compound. For example, substituents may be added to and/or chemical transformations performed upon, different intermediates to those mentioned hereinafter in conjunction with a particular reaction. This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis. The procedures may be adapted as appropriate to the reactants, reagents and other reaction parameters in a manner that will be evident to the skilled person by reference to standard textbooks and to the examples provided hereinafter.

It will be apparent to those skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

Pharmaceutically acceptable salts of the compounds of formula (I) include the acid addition and base salts thereof for compounds of sufficient acidity or basisity.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, and all polymorphs and prodrugs thereof. The invention also includes all isomers of the compounds of formula (I) (including optical, geometric and tautomeric isomers) as hereinafter defined and isotopically-labeled compounds of formula (I).

Within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. It will be appreciated that certain compounds of formula (I) may themselves act as prod-drugs of other compounds of formula (I). Further information on the use of prodrugs may be found in 'Pro-drugs as Novel Delivery Systems', Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing the 5-amino substituent on the pyrazole ring in the compounds of formula (I) with certain moieties known to those skilled in the art as 'pro-drug moieties' as described, for example, in "Design of Prodrugs" by H Bundgaard (Elsevier, 1985); "Design and application of prodrugs," Textbook of Drug Design and Discovery, (3$^{rd}$ Edition), 2002, 410-458, (Taylor and Francis Ltd., London); and references therein.

Suitable prodrugs may have an N-containing group at the 5-position of the pyrazole ring of formula (I) and are bound to the ring through N. The 5-N group can be substituted once or twice. Examples of substituents include: alkyl amines, aryl amines, amides, ureas, carbamates, cyclic carbamates, imines, enamines, imides, cyclic imides, sulfenamides, and sulfonamides. The hydrocarbon portion of these groups contain $C_{1-6}$ alkyl, phenyl, heteroaryl such as pyridyl, $C_{2-6}$ alkenyl, and $C_{3-8}$ cycloalkyl; wherein each of the above groups may include one or more optional substituents where chemically possible independently selected from: halo; hydroxy; $C_{1-6}$ alkyl and $C_{1-6}$ alkoxy.

Further examples of replacement groups in accordance with the foregoing example and examples of other prodrug types may be found in the aforementioned references.

A prodrug according to the invention can be readily identified by administering it to a test animal and sampling a body fluid for a compound of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO. Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof).

Compounds of this invention can also be mixed with one or more biologically active compounds or agents including insecticides, acaricides, anthelmintics, fungicides, nematocides, antiprotozoals, bactericides, growth regulators, entomopathogenic bacteria, viruses or fungi to form a multi-component pesticide giving an even broader spectrum of pharmaceutical, veterinary or agricultural utility. Thus the present invention also pertains to a composition comprising a biologically effective amount of compounds of the invention and an effective amount of at least one additional biologically active compound or agent and can further comprise one or more of surfactant, a solid diluent or a liquid diluent.

The following list of biologically active compounds together with which the compounds of the invention can be used is intended to illustrate the possible combinations, but not to impose any limitation.

For example, compounds of the present invention may be co-administered or used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel.

Compounds of this invention may also be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE-19520936.

Compounds of this invention may be co-administered or used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

Compounds of this invention may be co-administered or used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

Other examples of such biologically active compounds include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinaiphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, β-cyfluthrin, cyfluthrin, α-cypermethrin, β-cypermethrin, bioallethrin, bioallethrin ((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, λ-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene, fenoxycarb; d) lipid biosynthesis inhibitors: spirodiclofen Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin Biological agents: *Bacillus thuringiensis* ssp aizawai, kurstaki, *Bacillus thuringiensis* delta endotoxin, baculovirus, entomopathogenic bacteria, virus and fungi Bactericides: chlortetracycline, oxytetracycline, streptomycin, Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form. The compounds of the invention are of particular value in the control of parasites which are injurious to, or spread or act as vectors of diseases in, man and domestic animals, for example those hereinbefore mentioned, and more especially in the control of ticks, mites, lice, fleas, midges and biting, nuisance and myiasis flies. They are particularly useful in controlling arthropods which are present inside domestic host animals or which feed in or on the skin or suck the blood of the animal, for which purpose they may be administered orally, parenterally, percutaneously or topically.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

With respect to their use in mammals, the compounds may be administered alone or in a formulation appropriate to the specific use envisaged, the particular species of host mammal being treated and the parasite involved.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001).

The compounds of the invention may also be administered directly into the blood stream, into muscle, or into an internal organ. Suitable means for parenteral administration include bolus, intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include drenches, gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999). Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal. Injectable formulations may be prepared in the form of a sterile solution which may contain other substances, for example enough salts or glucose to make the solution isotonic with blood.

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 to 1000 µg of the compound of formula (I). The overall daily dose will typically be in the range 100 µg to 100 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.01 to 10% by weight of the active ingredient.

Such formulations are prepared in a conventional manner in accordance with standard medicinal or veterinary practice.

These formulations will vary with regard to the weight of active compound contained therein, depending on the species of host animal to be treated, the severity and type of infection and the body weight of the host. For parenteral, topical and oral administration, typical dose ranges of the active ingredient are 0.01 to 100 mg per kg of body weight of the animal. Preferably the range is 0.1 to 10 mg per kg.

As an alternative the compounds may be administered to a non-human animal with the drinking water or feedstuff and for this purpose a concentrated feed additive or premix may be prepared for mixing with the normal animal feed or drink.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to animal patients, the total daily dose of the compounds of the invention is typically in the range 0.1 mg/kg to 100 mg/kg depending, of course, on the mode of administration. For example, oral administration may require a total daily dose of from 0.5 mg/kg to 100 mg/kg, while an intravenous dose may only require from 0.1 mg/kg to 10 mg/kg. The total daily dose may be administered in single or divided doses. The veterinarian will readily be able to determine doses for individual animals according to age, weight and need.

The compounds of the invention also have utility in the control of plant pests, soil inhabiting pests and other environmental pests.

Compositions suitable for applications in agriculture, horticulture include formulations suitable for use as, for example, sprays, dusts, granules, fogs, foams, emulsions. The active compound is generally applied to the locus in which arthropod or nematode infestation is to be controlled at a rate of about 0.02 kg to about 20 kg of active compound per hectare of locus treated. Adverse weather conditions, pest resistance and other factors may require that the active ingredient be used in higher proportions. For foliar application, a rate of 0.01 to 1 kg/ha may be used.

The compounds of the invention may also be applied in solid or liquid compositions to the soil principally to control those nematodes dwelling therein but also to the foliage principally to control those nematodes attacking the aerial parts of the plants. The active component can be washed into the soil by spraying with water or by the natural action of rainfall. During or after application, the formulation can, if desired, be distributed mechanically in the soil.

Application can be prior to planting, at planting, after planting but before sprouting has taken place or after sprouting.

The compounds of the invention are of particular value in the protection of field, grassland, forage, plantation, glasshouse, orchard, grove and vineyard crops; or of vegetables and salads, of ornamental plants flowers and shrubs and of plantation and forest trees.

The effective use doses of the compounds employed in the invention can vary within wide limits, particularly depending on the nature of the pest to be eliminated or degree of infestation. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application. This carrier is therefore generally inert and it must be acceptable (for example, agronomically acceptable, particularly to the treated plant).

The carrier may be a solid, for example, ground natural minerals, such as attapulgite, bentonite, clays, chalk, diatomaceous earth, kaolins, montmorillonite, quartz, or talc, ground synthetic minerals, such as alumina, silica, or silicates, naturalsilicates, silica, resins, waxes, or solid fertilizers). As solid carriers for granules the following are suitable: crushed natural rocks such as calcite, dolomite, marble, pumice, and sepiolite; synthetic granules of inorganic or organic meals; granules of organic material such as, coconut shells, corn cobs, corn husks or sawdust; absorbent carbon black, kieselguhr, or powdered cork; water soluble polymers, resins, waxes; or solid fertilizers. Such solid compositions may, if desired, contain one or more compatible wetting, dispersing, emulsifying or colouring agents which, when solid, may also serve as a diluent.

The carrier may also be liquid, for example: water; alcohols, particularly butanol or glycol, as well as their ethers or esters, particularly methyl glycol acetate; ketones, particularly acetone, cyclohexanone, methylethyl ketone, methylisobutylketone, or isophorone; petroleum fractions such as aliphatic or aromatic hydrocarbons, particularly xylenes; mineral or vegetable oils; chlorinated hydrocarbons, particularly trichloroethane, methylene chloride or chlorobenzenes; water-soluble or strongly polar solvents such as dimethylformamide, dimethyl sulphoxide, or N-methylpyrrolidone; or a mixture thereof.

The surface-active agent may be an emulsifying agent, dispersing agent or wetting agent of the ionic or non-ionic type or a mixture of such agents. The presence of at least one surface-active agent is generally essential when the active ingredient and/or the inert carrier are not or only slightly water soluble and the carrier agent of the composition for application is water.

Compositions of the invention may further contain other additives such as adhesives or colorants. Adhesives such as natural or synthetic phospholipids or carboxymethylcellulose or natural or synthetic polymers in the form of powders, granules or lattices, can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or It is also possible to use trace nutrients such as salts of boron, cobalt, iron, manganese, copper, cobalt, molybdenum or zinc.

For their agricultural application, the compounds of the formula (I), or pesticidally acceptable salts thereof, are therefore generally in the form of compositions, which are in various solid or liquid forms.

Solid forms of compositions which can be used are dusting powders (with a content of the compound of formula (I), or a pesticidally acceptable salt thereof, ranging up to 80%), wettable powders or granules (including water dispersible granules), particularly those obtained by extrusion, compacting, impregnation of a granular carrier, or granulation starting from a powder (the content of the compound of formula (I), or a pesticidally acceptable salt thereof, in these wettable powders or granules being between about 0.5 and about 80%). Solid homogenous or heterogenous compositions containing one or more compounds of formula (I), or pesticidally acceptable salts thereof, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or nonaqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.0 1 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod, plant nematode, helminth or protozoan pests usually contain from about 0.00001% to about 95%, more particularly from about 0.0005% to about 50% by weight of one or more compounds of formula (I), or pesticidally acceptable salts thereof, or of total active ingredients (that is to say the compound of formula (I), or a pesticidally acceptable salt thereof, together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

They are also valuable in the protection of timber (standing, felled, converted, stored or structural) from attack by sawflies or beetles or termites. They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack. Solid or liquid compositions for application topically to timber, stored products or household goods usually contain from about 0.00005% to about 90%, more particularly from about 0.001% to about 10%, by weight of one or more compounds of formula (I) or pesticidally acceptable salts thereof.

The compounds of the invention (and their pharmaceutically, veterinarily and agriculturally acceptable salts) may be used, for example, in the following applications and on the following pests:

In the field of veterinary medicine or livestock husbandry or in the maintenance of public health against arthropods which are parasitic internally or externally upon vertebrates, particularly warm-blooded vertebrates, including man and domestic animals such as dogs, cats, cattle, sheep, goats, equines, swine, poultry and fish. Also, in the field of control of plant pests, soil inhabiting pests and other environmental pests. Illustrative of specific parasites which may be controlled by the compounds of this invention include arthropods such as:

Actinedida/Acaridida: chicken mite (*Mesostigmata* spp e.g. *Dermanyssus gallinae*); itch/scab mites (*Sarcoptes* spp e.g. *Sarcoptes scabiei*) mange mites (*Psoroptes* spp e.g. *Psoroptes ovis, Chorioptes* spp e.g. *Chorioptes bovis*); chiggers (*Trombicula* spp e.g. *Trombicula aifteddugesi*); *Damalinia* spp; *Demodex* spp; *Acarapis* spp; *Cheyletiella* spp; *Ornithocheyletia* spp; *Myobia* spp; *Listrophorus* spp; *Acarus* spp; *Tyrophagus* spp; *Caloglyphus* spp; *Hypodectes* spp; *Pterolichus* spp; *Otodectes* spp; *Notoedres* spp; *Cytodites* spp; *Knemidocoptes* spp; *Laminiosioptes* spp.

Siphonapterida: *Ctenocephalides* spp e.g. *Ctenocephalides canis, Ctenocephalides fells; Xenopsylla* spp e.g. *Xenopsylla cheopis; Pulex* spp e.g. *Pulex irritans; Ceratophyllus* spp.

Ticks: *Argas* spp e.g. *Argas persicus; Ornithodorus* spp e.g. *Ornithodorus moubata; Otobius* spp e.g. *Otobius megnini; Ixodes* spp e.g. *Ixodes ricinus, Ixodes rubicundus; Amblyomma* spp e.g. *Amblyomma americanum, Amblyomma variegatum; Boophilus* spp e.g. *Boophilus annulatus, Boophilus decoloratus, Boophilus microplus; Dermacentor* spp e.g. *Dermacentor silvarum; Haemophysalis* spp; *Hyalomma* spp e.g. *Hyalomma truncatum; Rhipicephalus* spp e.g. *Rhipicephalus sanguineus, Rhipicephalus appendiculatus, Rhipicephalus evertsi; Dermanyssus* spp; *Railletia* spp; *Pneumonyssus* spp; *Stemostoma* spp; *Varroa* spp; and other ticks e.g. *Brevipalpus phoenicis, Bryobia praetiosa, Eotetranychus carpini, Eriophyes sheldoni, Paratetranychus pilosus, Phyllocoptruta oleivora, Polyphagotarsonemus latus, Tetranychus cinnabarinus, Tetranychus kanzawai, Tetranychus pacificus, Tetranychus telarius.*

Adult flies (Diptera): Horn fly (*Haematobia irritans*); Horse fly (*Tabanus* spp e.g. *Tabanus* bovines); Stable fly (*Stomoxys calcitrans*); Black fly (*Simulium* spp); Deer fly (*Chrysops* spp); Louse fly (*Melophagus ovinus*); Tsetse fly (*Glossina* spp e.g. *Glossina morsitans*); Mosquitoes (*Culex* spp e.g. *Culex pipiens; Anopheles* spp e.g. *Anopheles maculipennis; Aedes* spp e.g. *Aedes egypti, Aedes vexans*); *Eusimulium* spp; *Phlebotonius* spp; *Lutzomyia* spp; *Culicoides* spp; *Hybomitra* spp; *Atylotus* spp; *Haematopota* spp; *Philipomyia* spp; *Braula* spp; *Hydrotaea* spp; *Morellia* spp; *Fannia* spp e.g. *Fannia canucularis; Calliphora* spp; *Wohlfahrtia* spp; *Sarcophaga* spp; *Hippobosca* spp; *Lipoptena* spp; *Melophagus* spp; and other Diptera such as *Anastrepha ludens; Ceratitis capitata; Chrysomya bezziana; Chrysomya hominivorax; Chrysomya macellaria; Contarinia sorghicola; Cordylopia anthropophaga; Dacus cucurbitae; Dasineura brassicae; Gasterophilus intestinalis; Haplodiplosis equestris; Hylemyia platura; Hypoderma lineata; Liriomyza sativae; Liriomyza trifolii; Lycoria pectoralis; Mayettiola destructor; Musca domestica; Muscina stabulans; Oestrus ovis; Oscinella frit; Pegomya hysocyami; Phorbia brassicae; Phorbia coarctata; Rhagoletia cerasi; Rhagoletis pomonella; Tipula oleraceam; Tipula paludosa*; and also Blow flies; Soldierflies; Midges and Punkies.

Parasitic fly maggots: Bot fly (*Oestrus ovis, Cuterebra* spp); Blow fly (*Phaenicia* spp, *Lucilia sericata, Lucilia cuprina*); Screwworm (*Cochliomyia hominivorax*); Cattle grub (*Hypoderma* spp); *Dermatobia hominis*.

Anoplurida: sucking lice (*Menopon* spp; *Bovicola* spp); biting lice (*Haematopinus* spp; *Linognathus* spp; *Solenoptes* spp; *Phtirus* spp).

True bugs: common bed bug (Cimicidae e.g. *Cimex lectularius*); kissing bugs (*Triatoma* spp e.g. *Rhodnius prolixus*).

Brachycera: Black flies; Biting midges; Sand flies; Sciarids.

Orthoptera: *Periplaneta* spp; *Blatella* spp e.g. *Blatella germanica; Gryllotalpa* spp e.g. *Gryllotalpa gryllotalpa; Acheta domestica; Blatta orientalis Forficula auricularia; Leucophaea maderae; Melanoplus bivittatus; Melanoplus femur-rubrum; Melanoplus mexicanus; Melanoplus sanguinipes; Melanoplus spretus; Momadacris septemfasciata; Schistocerca peregrina; Stauronotus maroccanus; Tachycines asynamorus.*

Dictyoptera: *Periplaneta fuliginosa; Periplaneta japonica; Periplaneta Americana.*

Hymenoptera: Carpenter ants; Bees; Hornets; Wasps.

Lepidoptera: *Adoxophyes orana fasciata; Agrotis ypsilon; Agrotis segetum; Alabama argillacea* Hubner; *Anticarsia gemmatalis; Archips argyrospila* Walker; *Archips rosana; Argyresthia conjugella; Autographa gamma; Autographa nigrisigna Barathra brassicae; Bupalus piniarius; Cacoecia murinana; Caloptilia theivora; Capua reticulana; Carposina niponensis; Chematobia brumata; Chilo polychrysus; Chilo suppressalis* Walker, *Choristoneura fumiferana; Choristoneura occidentalis; Cirphis unipuncta; Cnaphalocrosis medinalis* Guenee; *Cydia pomonella; Dendrolimus pini; Diaphania nitidalis; Diatraea grandiosella; Earias insulana* Boisduval; *Earias vittella* Fabricius; *Elasmopalpus lignosellus; Eupoecilia ambiguella; Evetria bouliana; Feltia subterrana; Galleria mellonella; Grapholitha funebrana; Grapholitha molesta; Helicoverpa armigera; Helicoverpa assulta; Helicoverpa zea; Heliothis virescens; Hellula unda-* lis; Hibernia defoliaria; Hyphantria cunea; Hyponomeuta malinellus; Keiferia lycopersicella; Lambdina fiscellaria; Laphygma exigua; Leucoptera coffeella; Leucoptera scitella; Lithocolletis blancardella; Lobesia botrana; Loxostege sticticalis; Lymantria monacha; Lyonetia clerkella; Malacosoma neustria; Mamestra brassicae; Naranga aenescens; Notarcha derogata; Orgyia pseudotsugata; Ostrinia nubilalis; Ostrinia fumacalis; Parnara guttata; Panolis flammea; Pectinophora gossypiella; Peridroma saucia; Phalera bucephala; Phyllocnistis citrella; Pieris brassicae; Pieris rapae; Plutella xylostella; Pseudaletia separate; Phthorimaea operculella; Phyllonorycter ringoneells; Plathypena scabra; Pseudoplusia includens; Rhyacionia frustrana; Scrobipalpula absoluta; Sitotroga cerealella; Sparganothis pilleriana; Spodoptera exigua; Spodoptera frugiperda; Spodoptera littoralis; Spodoptera litura; Thaumatopoea pityocampa; Tortrix viridans; Trichoplusia ni Hubner, Tryporyza incertulas; Tuta absoluta; Zeiraphera Canadensis; Lyonetid moths; Tussock moths; Casemaking clothes moth; Webbing clothes moth.

Coleoptera: *Agrilus sinuatus; Agriotes lineatus; Agriotes obscurus; Amphimellus solstitialis; Anisandrus dispar; Anobium punctatum; Anoplophora malasiaca; Anthonomus grandis; Anthonomus pomorum; Anthrenus verbasci; Apate monachus; Atomaria linearis; Aulacophora femoralis; Blastophagus piniperda; Blitophaga undata; Bostrychos capucins; Bruchus rufimanus; Bruchus pisorum; Bruchis lentis; Byctiscus betulae; Callosobruchus chinensis; Cassida nebulosa; Cerotoma trifurcata; Ceuthorrhynchus assimilis; Ceuthorrhynchus napi; Chaetocnema tibialis; Chlorophorus pilosis; Conoderus vespertinus; Crioceris asparagi; Diabrotica longicomis; Dendrobium pertinex; Diabrotica 12-punctata; Diabrotica virgifera; Dinoderus minutes; Echinocnemus squameus; Elilachna vigintioctopunctata; Ernobius mollis; Epilachna varivestis; Epitrix hirtipennis; Eutinobothrus brasiliensis; Heterobostrychus brunneus; Hylobius abietis; Hylotrupes bajulus; Hypera brunneipennis; Hypera postica; Ips typographus; Lasioderma serricome; Lema bilineata; Lema melanopus; Limonius californicus; Lissorhoptus oryzophilus; Lyctus brunneus; Lyctus linearis; Lyctus pubescens; Melanotus communis; Meligethes aeneus; Melolontha hippocastani; Melolontha melolontha; Minthes rugicollis; Oulema oryzae; Ortiorrhynchus sulcatus; Otiorrhynchus ovatus; Paederus fuscipes; Phaedon cochleariae; Phyllotreta chrysocephala; Phyllophaga spp; Phyllopertha horticola; Phyllotreta nemorum; Phyllotreta striotata; Popillia japonica; Priobium carpini; Ptilinus pecticornis; Sitona lineatus; Sitophilus granaria; Sphenophorus venatus; Tomicus piniperda; Tribolium castaneum; Trogoxylon aequale; Xestobium rufovillosum; Aupreous chafer*; Western corn rootworm; Rice water weevil; Adzuki bean beetle; Yellow mealworm; Red flour beetle; Striped flea beetle; Cucurbit leaf beetle; Deathwatch beetle; Drugetose beetle; Mexican bean beetle; Flea beetle; Japanese beetle; Boll weevil; Rice water weevil; Granary weevil; Rice weevil; Wireworms (*Agriotes* spp; *Athous* spp; *Limonius* spp); *Xyleborus* spp; *Tryptodendron* spp; *Sinoxylon* spp;

Homoptera: *Acyrthosiphon onobrychis; Adelges laricis; Aleurodes brassicae; Aphidula nasturtii; Aphis fabae; Aphis gossypii; Aphis pomi; Aphis sambuci; Aspiodotus hederae; Bemisia tabaci; Bemisia argentifolii; Brachycaudus cardui; Brevicoryne brassicae; Cerosipha gossypii; Cryptomyzus ribis; Diuraphis noxia; Dreyfusia nordmannianae; Dreyfusia piceae; Dysaphis radicola; Dysaulacorthum pseudosolani; Empoasca fabae; Eriosoma lanigerum; Euscelis bilobatus; Hyalopterus arundinis; Laodelphax stiatellus; Lecanium comi; Macrosiphum avenae; Macrosiphum euphorbiae; Macrosiphon rosae; Megoura viciae; Metolophium dirhodum; Myzodes persicae; Myzus cerasi; Myzus persicae; Nilaparvata lugens; Pemphigus bursarius; Perkinsiella saccharicida; Phorodon humuli; Psylla mall; Psylla piri; Rhopalomyzus ascalonicus; Rhopalosiphum maidis; Rhopalosiphum padi; Saissetia oleae; Sappaphis mala; Sappaphis mali; Schizaphis graminum; Schizoneura lanuginose; Sitobion avenae; Trialeurodes vaporariorum; Vites vitifolii.*

Hemiptera: *Aulacorthum solani; Aphis glycines; Eysarcoris parvus; Eurydema rugosum; Icerva purchasi; Laodelphax striatellus; Lipaphis etysimi; Nephotettix cincticeps; Planococcus citri; Pseudococcus comstocki; Riptortus clavatus; Scotinophora lurida; Sogatella furcifera; Stephanitis nashi; Unaspis vanonensis*; Small brown planthopper; Brown rice planthopper; Whitebacked rice planthopper; Stink bugs; Whiteflies; Lace bugs, Jumping plantlice.

And species of the orders: Hymenoptera; Isoptera; Isopoda; Diplopoda; Chilopoda; Symphyla; Thysanura; Dermaptera; and Heteroptera;

In the field of veterinary medicine or livestock husbandry or in the maintenance of public health for controlling helminths, nematodes and protozoa such as:

Trematoda: *Fasciola; Fascioloides; Paramphistomum; Dicrocoelium; Eurytrema; Ophisthorchis; Fasciolopsis; Echinostoma; Paragonimus.*

Nematodes: *Haemonchus; Ostertagia; Cooperia; Oesphagastomum; Nematodirus; Dictyocaulus; Trichuris; Dirofilaria; Ancyclostoma; Ascaris; Trichostrongylus.*

Protozoa: *Eimeria* spp; *Leishmania* spp; *Plasmodium* spp; *Babesis* spp; *Trichomonadidae* spp; *Toxoplasma* spp and *Theileria* spp.

In the protection of stored products, for example cereals, including grain or flour, groundnuts, animal feedstuffs, timber or household goods, e.g. carpets and textiles, compounds of the invention are useful against attack by arthropods such as:

Flour moths (*Ephestia* spp); Carpet beetles (*Anthrenus* spp); Flour beetles (*Tribolium* spp); Grain weevils (*Sitophilus* spp); Mites (*Acarus* spp)

In the protection against soil inhabiting insects such as:

Western corn rootworm, other *Diabrotica* spp, European chafer and other coleopteran grubs, and wireworms; adults and larvae of the orders Hemiptera and Homoptera including tarnished plant bug and other plant bugs (Miridae), aster leafhopper and other leaf hoppers (Cicadellidae), rice plant hopper, brown planthopper, and other planthoppers (Fulgoroidae), paylids, whiteflies (Aleurodidae), aphids (Aphidae), scales (Coccidae and Diaspididae), lace bugs (Tingidae), stink bugs (Pentamodidae), cinch bugs and other seed bugs (Lygaeidae), cicadas (Cicadidae), spittlebugs (Cercopids), squash bugs (Coreidae), red bugs and cotton stainers (Pyrrhocoridae); adults and larvae of the order acari including European red mite, two spotted mite, rust mites, McDaniel mite and other foliar feeding mites; adults and immatures of the order Orthoptera including grasshoppers; adults and immatures of the order Diptera including leafminers, midges, fruit flies (Tephritidae), and soil maggots; adults and immatures of the order Thysanoptera including onion thrips and other foliar feeding thrips.

For the avoidance of doubt, references herein to "treatment" include references to curative, palliative and prophylactic treatment, references to "control" (of parasites and/or pests etc.) include kill, repel, expel, incapacitate, deter, eliminate, alleviate, minimise, eradicate.

The compounds of the invention are of particular value in the control of arthropods which are injurious to, or spread or act as vectors of diseases in, man and domestic animals, for example those hereinbefore mentioned, and more especially in the control of ticks, mites, lice, fleas, midges and biting, nuisance and myiasis flies. They are particularly useful in controlling arthropods which are present inside domestic host animals or which feed in or on the skin or suck the blood of the animal, for which purpose they may be administered orally, parenterally, percutaneously or topically.

Regarding the use of the compounds of the invention in mammals, there is provided:

a pharmaceutical or veterinary parasiticidal composition comprising a compound of formula (I), or a pharmaceutically or veterinarily acceptable salt thereof, or a pharmaceutically or veterinarily acceptable solvate of either entity, together with a pharmaceutically or veterinarily acceptable diluent or carrier, which may be adapted for oral, parenteral or topical administration;

a compound of formula (I), or a pharmaceutically or veterinarily acceptable salt thereof, or a pharmaceutically or veterinarily acceptable solvate of either entity, or a pharmaceutical or veterinary composition containing any of the foregoing, for use as a medicament;

the use of a compound of formula (I), or a pharmaceutically or veterinarily acceptable salt thereof, or a pharmaceutically or veterinarily acceptable solvate of either entity, or a pharmaceutical or veterinary composition containing any of the foregoing, for the manufacture of a medicament for the treatment of a parasitic infestation; and a method of treating a parasitic infestation in a mammal which comprises treating said mammal with an effective amount of a compound of formula (I), or a pharmaceutically or veterinarily acceptable salt thereof, or a pharmaceutically or veterinarily acceptable solvate of either entity, or a pharmaceutical or veterinary composition containing any of the foregoing.

According to another aspect of the present invention, there is provided a method for the control of arthropod, plant nematode or helminth pests at a locus which comprises the treatment of the locus (e.g. by application or administration) with an effective amount of a compound of general formula I, or a pesticidally acceptable salt thereof.

The present invention also relates to a method of cleaning animals in good health comprising the application to the animal of compound of formula (I) or a veterinarily acceptable salt. The purpose of such cleaning is to reduce or eliminate the infestation of humans with parasites carried by the animal and to improve the environment which humans inhabit.

The flea membrane feed test is used to measure the biological activities of the compounds claimed. The assay involves in vitro testing against *Ctenocephalides felis* conducted according to the following general procedure.

Fleas are cultured in vitro using dog blood. 25-30 adult *Ctenocephalides felis* (cat flea) were collected and placed in a test chamber (50 ml polystyrene tube with fine nylon mesh sealing the end). Citrated dog blood was prepared by adding aqueous sodium citrate solution (10 ml, 20% w/v, 20 g sodium citrate in 100 ml water) to dog blood (250 ml). Test compounds were dissolved in dimethylsulfoxide to give a working stock solution of 4 mg/ml. The stock solution (12.5 µl) was added to citrated dog blood (5 ml) to give an initial test concentration of 10 µg/ml. For testing at 30 µg/ml, working stock solutions of 12 mg/ml were prepared.

Citrated dog blood containing the test compound (5 ml, 10 µg/ml) was placed into a plastic Petri dish lid, which was kept at 37° C. on a heated pad. Parafilm was stretched over the open top to form a tight membrane for the fleas to feed through. The test chamber containing the fleas was placed carefully onto the parafilm membrane and the fleas commenced feeding.

The fleas were allowed to feed for 2 hours and the test chambers were then removed and stored overnight at room temperature.

The fleas were observed and the percentage of fleas killed recorded. Compounds were initially tested at 10 µg/ml, wherefrom relevant dose responses (100, 30, 10, 3, 1, 0.3, 0.1 µg/ml) were conducted and repeated n=5. Data was plotted to generate ED80, ED90 & ED95 values.

The compounds of the present invention have significantly better activity than the prior art compounds. All the examples of the present invention have flea ED80 values of less than 100 µg/ml. Results for some of the compounds are presented below.

| Example | Flea feed ED80 results |
| --- | --- |
| 5 | 1 |
| 84 | 3 |
| 27 | 0.1 |

Instruments Used to Acquire Characterising Data

Nuclear magnetic resonance spectral data were obtained using Varian (nova 300, Varian (nova 400, Varian Mercury 400, Varian Unityplus 400, Bruker AC 300 MHz, Bruker AM 250 MHz or Varian T60 MHz spectrometers, the observed chemical shifts being consistent with the proposed structures. Mass spectral data were obtained on a Waters Micromass ZQ, or a Hewlett Packard GCMS System Model 5971 spectrometer. The calculated and observed ions quoted refer to the isotopic composition of lowest mass. HPLC means high performance liquid chromatography. Room temperature means 20 to 25° C.

Compounds of the present invention are exemplified below.

EXAMPLE 1

N-{5-amino-3-cyano-1-[2,6-dichloro-4-pentafluorothiophenyl]-1H-pyrazol-4-yl}-N-(2,2-difluoroethyl)methanesulfonamide

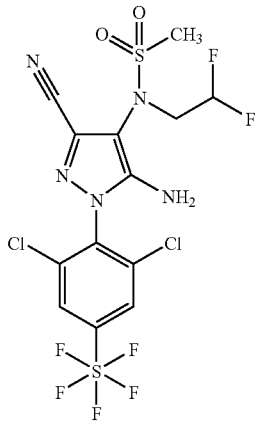

To a mixture of N-{5-amino-3-cyano-1-[2,6-dichloro-4-pentafluorothiophenyl]-1H-pyrazol-4-yl}methanesulfonamide (200 mg, 0.42 mmol) and 2,2-difluoroethyl trifluoromethanesulphonate (600 mg, 2.80 mmol)

in acetonitrile (12 ml) was added potassium carbonate (116 mg, 0.84 mmol). The reaction mixture was then stirred at 40° C. for 1 h. To the reaction mixture was added water (10 ml) and the mixture was extracted with diethyl ether (2×8 ml). The combined extracts were dried (MgSO$_4$) and concentrated in vacuo. The residue was dissolved in acetonitrile (1.5 ml) and the solution was purified by automated preparative liquid chromatography (Gilson system, 150 mm×30 mm Phenomonex LUNA II 10 μm C18 column) using an acetonitrile:water gradient [50:50 to 98:2]. The appropriate fractions were concentrated in vacuo to give the titled compound (145 mg).

Experimental MH$^+$ 535.9; expected 536.0.

$^1$H-NMR (DMSO): 3.05-3.09 (3H), 3.53-3.77 (1H), 3.86-4.09 (1H), 5.99-6.27 (1H), 6.53-6.61 (2H), 8.41-8.45 (2H)

EXAMPLE 2

N-{5-amino-3-cyano-1-[2,6-dichloro-4-pentafluorothiophenyl]-1H-pyrazol-4-yl}-1,1,1-trifluoro-N-methylmethanesulfonamide

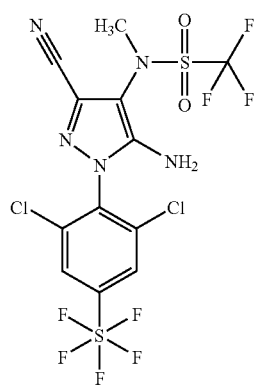

To Preparation 14 in methanol (5 ml) was added hydrochloric acid (4N, 3 ml) and the reaction mixture was heated at 80° C. overnight. The reaction mixture was concentrated in vacuo and the residue was partitioned between ethyl acetate (20 ml) and water (20 ml). The organic layer was separated, washed with water (2×20 ml), dried (Na$_2$SO$_4$) and concentrated in vacuo. The crude product was dissolved in a mixture of acetonitrile, dimethyl sulphoxide and water (4:5:1, 2 ml) and purified by automated preparative liquid chromatography (Gilson system, 150 mm×30 mm Phenomonex LUNA C18 (2) 10 μm column) using an acetonitrile:water gradient [60:40 to 95:5]. The appropriate fractions were concentrated in vacuo to give the titled compound (60 mg).

Experimental MH$^+$ 539.9; expected 539.9

$^1$H-NMR (CDCl3): 3.53-3.55 (3H), 4.08-4.12 (2H), 7.89-7.92 (2H)

Similarly prepared were:

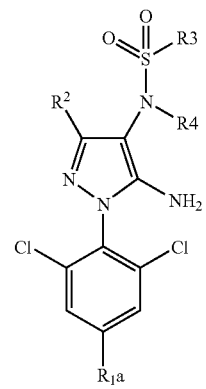

| Ex | R1a | R2 | R4 | R3 | From prep. |
|---|---|---|---|---|---|
| 3 | CF$_3$ | CN | H | 3,4-difluorophenyl | 1 |
| 4 | ' | ' | cyclopropylmethyl | Me | 6 |
| 5 | ' | ' | cyanomethyl | Me | 7 |
| 6 | ' | ' | pyridin-2-ylmethyl | Me | 8 |
| 7 | ' | ' | benzyl | Me | 9 |
| 8 | ' | ' | 2-(N,N-dimethylamino)ethyl | Me | 13 |
| 9 | ' | ' | H | methylsulfonylmethyl | 2 |
| 10 | ' | ' | 2-hydroxyethyl | Me | 10 |
| 11 | ' | ' | methylthiomethyl | Me | 11 |
| 12 | ' | ' | cyclopropylsulfonyl | Me | 17 |
| 13 | ' | ' | N,N-dimethylsulfonyl | Me | 18 |
| 14 | ' | ' | methylsulfonyl | Me | 12 |
| 15 | ' | ' | H | Me | 15 |
| 16 | ' | ' | H | benzyl | 4 |
| 17 | ' | ' | H | 2-phenylethenyl | 5 |
| 18 | SF$_5$ | CF$_3$ | methylsulfonyl | Me | 20 |
| 19 | CF$_3$ | CN | | | 50 |

EXAMPLE 3

Experimental MH$^+$ 512.0; expected 512.0

$^1$H-NMR (CDCl3): 3.46-3.46 (2H), 6.28-6.31 (1H), 7.32-7.38 (1H), 7.56-7.61 (2H), 7.77-7.79 (2H)

EXAMPLE 4

Experimental MH$^+$ 468.2; expected 468.0

$^1$H-NMR (CDCl3): 0.17-0.23 (2H), 0.50-0.56 (2H), 0.97-1.05 (1H), 3.06-3.07 (3H), 3.50-3.55 (2H), 4.15-4.19 (2H), 7.77-7.78 (2H)

EXAMPLE 5

Experimental MH$^+$ 453.2; expected 453.0

$^1$H-NMR (CDCl3): 3.08-3.12 (3H), 3.30-3.39 (2H), 4.49-4.52 (2H), 7.69-7.72 (2H)

EXAMPLE 6

Experimental MH$^+$ 505.3; expected 505.0

$^1$H-NMR (CDCl3): 3.06-3.08 (3H), 4.91-4.98 (2H), 7.23-7.28 (2H), 7.32-7.36 (1H), 7.71-7.73 (2H), 8.51-8.54 (1H)

EXAMPLE 7

Experimental MH+ 504.3; expected 504.0
1H-NMR (CDCl3): 3.15-3.16 (3H), 3.66-3.71 (2H), 7.24-7.28 (3H), 7.29-7.33 (2H), 7.67-7.69 (2H)

EXAMPLE 8

Experimental MH+ 485.0; expected 485.1
1H-NMR (CDCl3): 2.19-2.38 (6H), 2.41-2.57 (2H), 3.10-3.15 (3H), 3.70-3.94 (2H), 4.97-5.23 (2H), 7.75-7.78 (2H)

EXAMPLE 9

Experimental MH+ 491.9; expected 492.0
1H-NMR (DMSO): 3.19-3.22 (3H), 4.98-5.03 (2H), 6.19-6.28 (2H), 8.19-8.25 (2H), 9.83-9.87 (1H)

EXAMPLE 10

Experimental MH+ 458.0; expected 458.0
1H-NMR (CD3OD): 3.07-3.08 (3H), 3.61-3.75 (4H), 7.98-8.01 (2H)

EXAMPLE 11

1H-NMR (CDCl3): 2.23-2.25 (3H), 3.10-3.12 (3H), 4.21-4.25 (2H), 4.76-4.80 (2H), 7.77-7.78 (2H)

EXAMPLE 12

Experimental MH+ 517.9; expected 518.0
1H-NMR (CD3OD): 1.18-1.26 (4H), 3.06-3.10 (1H), 3.45-3.46 (3H), 7.55-7.59 (2H)

EXAMPLE 13

Experimental MH+ 520.9; expected 521.0
1H-NMR (CDCl3): 2.98-3.02 (6H), 3.44-3.47 (3H), 4.25-4.33 (2H), 7.76-7.80 (2H)

EXAMPLE 14

Experimental MH+ 491.9; expected 492.0
1H-NMR (CDCl3): 3.44-3.54 (6H), 4.11-4.23 (2H), 7.75-7.85 (2H)

EXAMPLE 15

Experimental MH+ 414.0; expected 414.0. 1H-NMR (CD3OD): 3.02-3.07 (3H), 7.97-8.02 (2H)

EXAMPLE 16

Experimental MH+ 490.0; expected 490.0
1H-NMR (CD3OD): 4.41-4.44 (2H), 7.30-7.37 (3H), 7.41-7.46 (2H), 7.95-8.01 (2H)

EXAMPLE 17

Experimental MH+ 502.0; expected 502.0
1H-NMR (CD3OD): 6.97-7.03 (1H), 7.25-7.31 (1H), 7.35-7.40 (3H), 7.52-7.56 (2H), 7.90-7.95 (2H)

EXAMPLE 18

Experimental MH+ 592.9; expected 592.9
1H-NMR (CDCl3): 3.38-3.42 (6H), 4.06-4.12 (2H), 7.89-7.92 (2H)

EXAMPLE 19

Experimental MW 440.0; expected 440.0
1H-NMR (CDCl3): 2.54-2.67 (2H), 3.33-3.44 (2H), 3.79-3.89 (2H), 4.20-4.36 (2H), 7.73-7.81 (2H)

EXAMPLE 20

N-{5-amino-3-cyano-1-[2,6-dichloro-4-(trifluoromethyl)phenyl]-1H-pyrazol-4-yl}-1,1,1-trifluoro-N-methylmethanesulfonamide

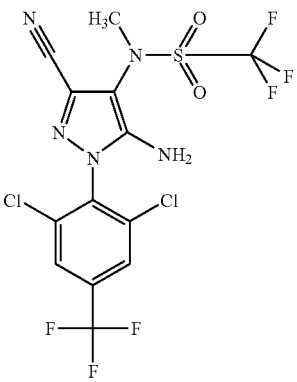

To a solution of N-(3-cyano-1-[2,6-dichloro-4-(trifluoromethyl)phenyl]-5-{[(dimethylamino)methylene]amino}-1H-pyrazol-4-yl)-1,1,1-trifluoro-N-methylmethanesulfonamide (240 mg, 0.45 mmol) in methanol (7 ml) was added hydrochloric acid (4N, 4 ml) and the reaction mixture was heated at reflux for 4 h. The reaction mixture was concentrated under nitrogen and the residue partitioned between ethyl acetate and water. The two layers were separated and the aqueous layer was extracted with ethyl acetate (×2). The combined organic phases were dried (MgSO4) and concentrated under nitrogen. The crude product was dissolved in acetonitrile (4 ml) and purified by automated preparative liquid chromatography (Gilson system, 150 mm×21.2 mm Phenomonex LUNA 100 Å C18 column) using an acetonitrile:water gradient [50:50 to 98:2]. The appropriate fractions were concentrated in vacuo to give the titled compound (105 mg).

Experimental MH+ 482.0; expected 482.0
1H-NMR (CDCl3): 3.50-3.52 (3H), 4.00-4.10 (2H), 7.71-7.76 (2H)

EXAMPLE 21

N-{5-amino-3-cyano-1-[2,6-dichloro-4-(trifluoromethyl)phenyl]-1H-pyrazol-4-yl}-N-(cyclopropylmethyl)-1,1,1-trifluoromethanesulfonamide

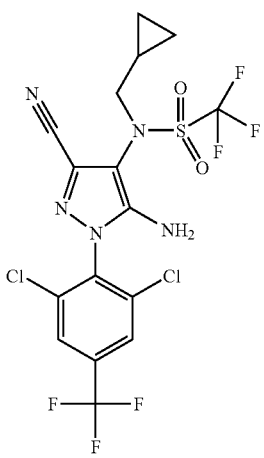

To a solution of N-(3-cyano-1-[2,6-dichloro-4-(trifluoromethyl)phenyl]-5-{[(dimethylamino)methylene]amino}-1H-pyrazol-4-yl)-1,1,1-trifluoromethanesulfonamide (250 mg, 0.48 mmol) in acetone (6 ml) was added potassium carbonate (100 mg, 0.72 mmol), a catalytic amount of sodium iodide and (bromomethyl)cyclopropane (69.5 µl, 0.72 mmol). The reaction mixture was then stirred at 60° C. overnight. The reaction mixture was concentrated under a stream of nitrogen and the residue was partitioned between dichloromethane (20 ml) and water (20 ml). The two layers were separated and the organic phase was washed with water, dried (Na$_2$SO$_4$) and concentrated in vacuo to give the protected compound. To a solution of the protected compound in methanol (5 ml) was added hydrochloric acid (4M, 3 ml) and the reaction mixture was heated at reflux. The reaction mixture was concentrated in vacuo and the residue was extracted with ethyl acetate (20 ml). The organic phase was washed with water (2×20 ml), dried (Na$_2$SO$_4$) and concentrated in vacuo. The crude product was dissolved in a mixture of acetonitrile (1 ml), dimethyl sulphoxide (2.4 ml) and water (0.6 ml) and purified by automated preparative liquid chromatography (Gilson system, 150 mm×30 mm Phenomonex LUNA C18 (2) 10 µm column) using an acetonitrile:water gradient [60:40 to 95:5]. The appropriate fractions were concentrated in vacuo to give the titled compound (120 mg).

Experimental MH$^+$ 522.3; expected 522.0

$^1$H-NMR (CDCl3): 0.19-0.29 (2H), 0.54-0.64 (2H), 0.99-1.10 (1H), 3.53-3.78 (2H), 4.01-4.13 (2H), 7.72-7.84 (2H)

EXAMPLE 22

N-{5-amino-3-cyano-1-[2,6-dichloro-4-(trifluoromethyl)phenyl]-1H-pyrazol-4-yl}-N-(2,2,2-trifluoroethyl)methanesulfonamide

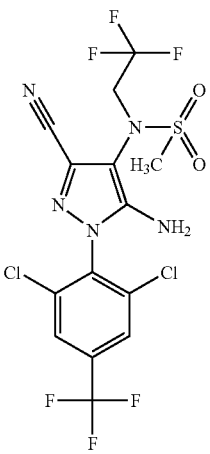

To a solution of N-(3-cyano-1-[2,6-dichloro-4-(trifluoromethyl)phenyl]-5-{[(dimethylamino)methylene]amino}-1H-pyrazol-4-yl)methanesulfonamide (250 mg, 0.53 mmol) in 1-methyl-2-pyrrolidinone (anhydrous, 5 ml) was added sodium hydride (60% in oil, 16.6 mg, 0.69 mmol) and 2,2,2-trifluoroethyl trichloromethanesulphonate (195 mg, 0.69 mmol). The reaction mixture was then stirred at room temperature for 3 h. To the reaction mixture was added dichloromethane (20 ml) and the resulting mixture was extracted with water (20 ml). The organic phase was washed with water (2×20 ml) and brine (2×20 ml), dried (Na$_2$SO$_4$) and concentrated in vacuo. To the residue was added methanol (5 ml) and hydrochloric acid (4M, 3 ml) and the mixture was heated at reflux for 60 h. The reaction mixture was concentrated in vacuo and to the residue was added ethyl acetate (20 ml) and water (20 ml). The organic phase was separated, washed with water (2×20 ml) and brine (2×20 ml), dried (Na$_2$SO$_4$) and concentrated in vacuo. The crude product was dissolved in acetonitrile/dimethyl sulphoxide/water (1:4:1, 6 ml) and purified by automated preparative liquid chromatography (Gilson system, 150 mm×30 mm Phenomonex LUNA C18 (2) 10 µm column) using an acetonitrile:water gradient [52.5:47.5 to 95:5]. The appropriate fractions were concentrated in vacuo to give the titled compound (135 mg).

Experimental MH$^+$ 496.2; expected 496.0

$^1$H-NMR (CDCl3): 3.10-3.14 (3H), 4.07-4.33 (4H), 7.74-7.80 (2H)

EXAMPLE 23

N-{5-amino-3-cyano-1-[2,6-dichloro-4-(trifluoromethyl)phenyl]-1H-pyrazol-4-yl}-1,1,1-trifluoro-N-(methylsulfonyl)methanesulfonamide

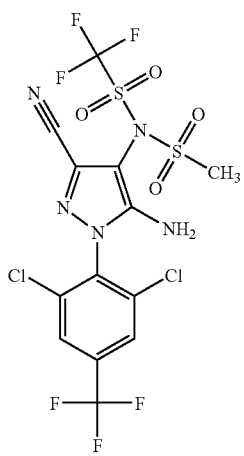

To a solution of N-{5-amino-3-cyano-1-[2,6-dichloro-4-(trifluoromethyl)phenyl]-1H-pyrazol-4-yl}methanesulfonamide (73 mg, 0.18 mmol) in dichloromethane (4 ml), at 0° C., was added dropwise triethylamine (30 μl, 0.21 mmol), followed by trifluoromethanesulphonic anhydride (30 μl, 0.18 mmol). The reaction mixture was allowed to warm to room temperature and stirred for 4 h. To the reaction mixture was added water and dichloromethane. The two layers were separated and the aqueous layer was extracted with dichloromethane (×3). The combined organic phases were then dried (MgSO$_4$) and concentrated in vacuo. The crude product was dissolved in acetonitrile/water (7:3, 5 ml) and purified by automated preparative liquid chromatography (Gilson system, 150 mm×30 mm Phenomenex LUNA C18(2) 10 μm column) using an acetonitrile:water gradient [55:45 to 95:5]. The appropriate fractions were concentrated in vacuo to give the titled compound (50 mg).

Experimental MH$^+$ 543.9; expected 543.9

$^1$H-NMR (CDCl3): 3.57-3.58 (3H), 4.12-4.20 (2H), 7.77-7.81 (2H)

EXAMPLE 24

N-{5-amino-3-cyano-1-[2,6-dichloro-4-(trifluoromethyl)phenyl]-1H-pyrazol-4-yl}-N-[(methylsulfonyl)methyl]methanesulfonamide To a solution of N-{5-amino-3-cyano-1-[2,6-dichloro-4-(trifluoromethyl)phenyl]-1H-pyrazol-4-yl}-N-[(methylthio)methyl]methanesulfonamide (108 mg, 0.23 mmol) in acetone (35 ml) was added sodium carbonate (318 mg, 3.04 mmol), followed by Oxone® (924 mg, 1.52 mmol) in water (12 ml). The reaction mixture was then stirred at room temperature for 5 h. To the reaction mixture was added water and the solution was extracted with ethyl acetate. The combined extracts were washed with brine, dried (MgSO$_4$) and concentrated in vacuo. The crude product was dissolved in a mixture of acetonitrile (1 ml) and water (1 ml) and purified by automated preparative liquid chromatography (Gilson system, 150 mm×30 mm Phenomenex LUNA C18(2) 10 μm column) using an acetonitrile:water gradient [45:55 to 95:5]. The appropriate fractions were concentrated in vacuo to give the titled compound (55 mg).

Experimental MH$^+$ 505.9; expected 506.0

$^1$H-NMR (CDCl3): 3.05-3.07 (3H), 3.15-3.18 (3H), 4.43-4.54 (2H), 7.74-7.80 (2H)

EXAMPLE 25

N-{5-am H-pyrazol-4-yl}-N-cyclobutyl-1,1,1-trifluoromethanesulfonamide

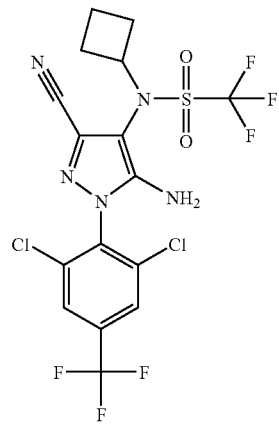

To a solution of Preparation 12 (250 mg, 0.43 mmol) in tetrahydrofuran (15 ml) was added hydrochloric acid (4M, 15 ml). The reaction mixture was then heated at reflux overnight. The reaction mixture was concentrated in vacuo and the residue was partitioned between water (50 ml) and dichloromethane (75 ml). The organic layer was separated, dried (Na$_2$SO$_4$) and concentrated in vacuo. The crude product was dissolved in acetonitrile (6 ml) and the solution was passed through a 0.45μ filter. The solution was then purified by automated preparative liquid chromatography (Gilson system, 150 mm×30 mm Phenomonex LUNA II 10μ C18 column) using an acetonitrile:water gradient [60:40 to 95:5]. The appropriate fractions were concentrated in vacuo to give the titled compound (113 mg).

Experimental MH$^+$ 522.0; expected 522.0

$^1$H-NMR (Acetone): 0.23-0.31 (2H), 0.56-0.64 (2H), 1.12-1.20 (1H), 3.56-3.78 (2H), 6.12-6.22 (2H), 8.02-8.13 (2H)

EXAMPLE 26

N-{5-amino-3-cyano-1-[2,6-dichloro-4-pentafluorothiophenyl]-1H-pyrazol-4-yl}-N-(methylsulfonyl)methanesulfonamide

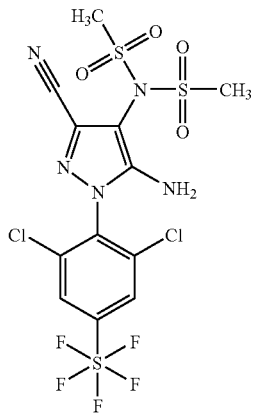

To a solution of Preparation 23 (200 mg, 0.45 mmol) in anhydrous dichloromethane (5 ml), at 0° C., was added triethylamine (124 μl, 0.9 mmol) and methanesulphonyl chloride (70 μl, 0.9 mol). The reaction mixture was then stirred under nitrogen for 30 min. To the reaction mixture was added dichloromethane (20 ml) and the resulting mixture was extracted with water (20 ml). The organic phase was washed with water (2×20 ml) and brine (2×20 ml), dried (Na$_2$SO$_4$) and concentrated in vacuo. To the residue was added methanol (5 ml) and hydrochloric acid (4M, 3 ml) and the mixture was heated at reflux for 60 h. The reaction mixture was concentrated in vacuo and to the residue was added ethyl acetate (20 ml) and water (20 ml). The organic phase was separated, washed with water (2×20 ml) and brine (2×20 ml), dried (Na$_2$SO$_4$) and concentrated in vacuo. The crude product was dissolved in a mixture of acetonitrile and water (1:1:5 ml) and purified by automated preparative liquid chromatography (Gilson system, 150 mm×30 mm Phenomonex LUNA C18 (2) 10 μm column) using an acetonitrile:water gradient [60:40 to 95:5]. The appropriate fractions were concentrated in vacuo to give the titled compound (80 mg).

Experimental MH$^+$ 549.9; expected 549.9

$^1$H-NMR (CDCl3): 3.41-3.47 (6H), 4.09-4.19 (2H), 7.88-7.94 (2H)

EXAMPLE 27

N-{3-cyano-1-[2,6-dichloro-4-(trifluoromethyl)phenyl]-1H-pyrazol-4-yl}-1,1,1-trifluoro-N-methyl methanesulfonamide

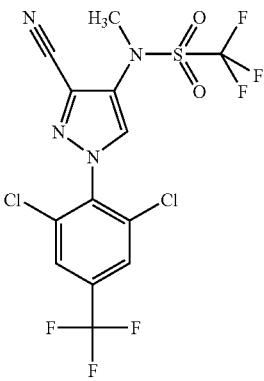

To a solution of Example 20 (150 mg, 0.31 mmol) in tetrahydrofuran (5 ml) was added dropwise tert-butyl nitrite (111 μl, 0.93 mmol). The reaction mixture was then heated at 60° C. overnight. The reaction mixture was concentrated in vacuo and the residue was partitioned between ethyl acetate (20 ml) and water (20 ml). The organic layer was separated, washed with brine (20 ml), dried (Na$_2$SO$_4$) and concentrated in vacuo. The residue was purified by column chromatography (silica, 10 g) eluting with dichloromethane/ethyl acetate [9:1]. The appropriate fractions were combined and concentrated to give the crude product. The crude product was dissolved in a mixture of acetonitrile, dimethyl sulphoxide and water (4:5:1, 2 ml) and purified by automated preparative liquid chromatography (Gilson system, 150 mm×30 mm Phenomonex LUNA C18(2) 10 μm column) using an acetonitrile:water gradient [60:40 to 95:5]. The appropriate fractions were concentrated in vacuo to give the titled compound (80 mg).

Experimental MH$^+$ 467.0; expected 467.0

$^1$H-NMR (CDCl3): 3.65-3.65 (3H), 7.77-7.80 (2H), 7.80-7.82 (1H)

Similarly prepared was:

EXAMPLE 28

N-{3-cyano-1-[2,6-dichloro-4-(trifluoromethyl)phenyl]-1H-pyrazol-4-yl}-N-(methylsulfonyl)methanesulfonamide

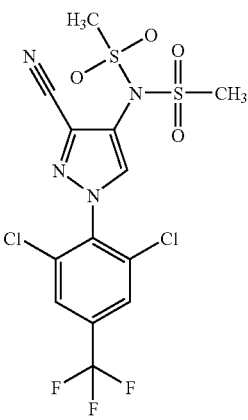

from the compound of Example 14 (1.00 g, 2.03 mmol) to give the title compound (855 mg).

Experimental MH⁺ 477.0; expected 477.0

¹H-NMR (CDCl3): 3.45-3.46 (6H), 7.75-7.78 (2H), 7.80-7.83 (1H)

EXAMPLE 29

N-{3-cyano-1-[2,6-dichloro-4-pentafluorothiophenyl]-1H-pyrazol-4-yl}-N-(methylsulfonyl)methanesulfonamide

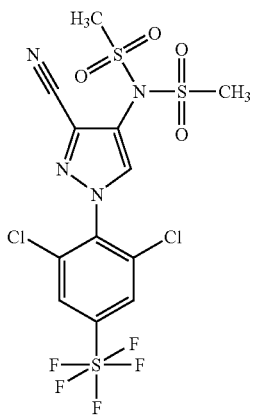

To a solution of Example 26 (310 mg, 0.56 mmol) in tetrahydrofuran (4 ml) was added dropwise tert-butyl nitrite (200 µl, 1.69 mmol). The reaction mixture was then heated at reflux for 16 h. The reaction mixture was concentrated in vacuo and the crude product was dissolved in acetonitrile (6 ml). The solution was passed through a 0.45µ filter and purified by automated preparative liquid chromatography (Gilson system, 150 mm×30 mm Phenomonex LUNA II 10µ C18 column) using an acetonitrile:water gradient [60:40 to 95:5]. The appropriate fractions were concentrated in vacuo to give the titled compound (169 mg).

¹H-NMR (Acetone): 3.56-3.57 (6H), 8.28-8.35 (2H), 8.73-8.79 (1H)

EXAMPLE 30

N-{3-cyano-1-[2,6-dichloro-4-(trifluoromethyl)phenyl]-1H-pyrazol-4-yl}methanesulfonamide

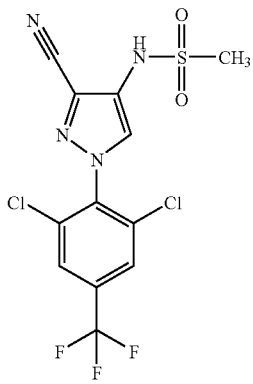

To a solution of Example 28 (855 mg, 1.79 mmol) in tetrahydrofuran (20 ml) was added potassium carbonate (617 mg, 4.48 mmol) in methanol (20 ml), containing a few drops of water. The reaction mixture was then stirred at room temperature for 2 h. The reaction mixture was concentrated in vacuo and to the residue was added hydrochloric acid (2M, 50 ml) and dichloromethane (100 ml). The organic phase was then separated, dried (Na₂SO₄) and concentrated in vacuo. The residue was purified using an Isolute™ cartridge (silica, 20 g) with gradient elution, cyclohexane:ethyl acetate [1:0 to 1:1]. The appropriate fractions were combined and concentrated to give the titled compound (600 mg).

Experimental MH⁺ 399.0; expected 399.0

¹H-NMR (CDCl3): 3.08-3.10 (3H), 6.69-6.74 (1H), 7.73-7.78 (2H), 7.80-7.84 (1H)

EXAMPLE 31

N-{3-cyano-1-[2,6-dichloro-4-(trifluoromethyl)phenyl]-1H-pyrazol-4-yl}-N-(2,2,2-trifluoroethyl)methanesulfonamide

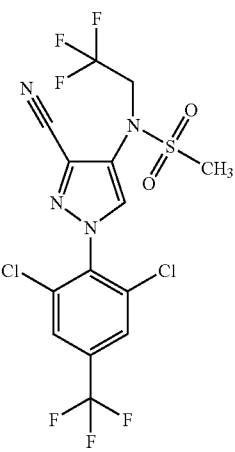

To a solution of sodium hydride (60% in oil, 14 mg, 0.35 mmol) in 1-methyl-2-pyrrolidinone (6 ml) was added Example 30 (115 mg, 0.29 mmol), followed by 2,2,2-trifluoroethyl trichloromethane sulphonate (185 mg, 0.66 mmol), added via syringe. The reaction mixture was then heated at 65° C. for 6 days. The reaction mixture was concentrated in vacuo and the residue was purified using an Isolute™ cartridge (silica, 5 g) with gradient elution, dichloromethane: methanol [100:0 to 95:5]. The appropriate fractions were combined and concentrated to give the titled compound (41 mg).

¹H-NMR (CDCl3): 3.09-3.13 (3H), 4.27-4.34 (2H), 7.72-7.79 (2H), 7.83-7.87 (1H)

EXAMPLE 32

N-{5-amino-3-cyano-1-[2,6-dichloro-4-pentafluorothiophenyl]-1H-pyrazol-4-yl}-N-(2,2,2-trifluoroethyl)methanesulfonamide

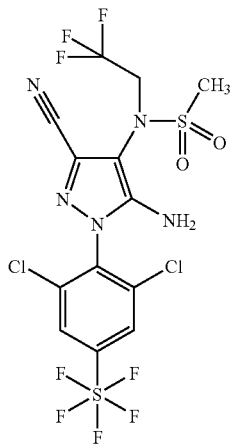

To a solution of Preparation 24 (80 mg, 0.13 mmol) in dioxane (2 ml) and methanol (1 ml) was added hydrochloric acid (5N, 1 ml). The reaction mixture was then heated at 85° C. overnight. The reaction mixture was concentrated in vacuo and the residue was partitioned between water (5 ml) and ethyl acetate (10 ml). The organic layer was separated, dried (MgSO$_4$) and concentrated in vacuo. The crude product was dissolved in a mixture of acetonitrile and water and dimethyl (1:2, 1.6 ml) and purified by automated preparative liquid chromatography (Gilson system, 150 mm×30 mm Phenomonex LUNA C18(2) 10 μm column) using an acetonitrile:water gradient [55:45 to 95:5]. The appropriate fractions were concentrated in vacuo to give the titled compound (43 mg).

Experimental MH$^+$ 553.9; expected 554.0
$^1$H-NMR (CDCl3): 3.11-3.14 (3H), 4.12-4.30 (4H), 7.90-7.93 (2H)

Similarly prepared were:

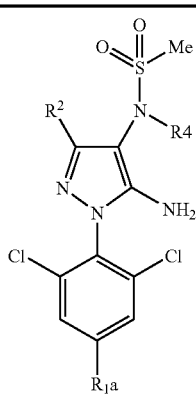

| Ex | R1a | R2 | R4 | From Prep |
|---|---|---|---|---|
| 33 | SF$_5$ | CN | 2-(1H-1,2,4-triazoly-yl)ethyl | 42 |
| 34 | " | CONH$_2$ | Methylsulfonyl | 37 |
| 35 | OCF$_3$ | CN | " | 21 |
| 36 | SF$_5$ | COCH$_3$ | " | 38 |
| 37 | OCHF$_2$ | CN | " | 22 |

EXAMPLE 33

Experimental MH$^+$ 567.0; expected 567.0
$^1$H-NMR (CDCl3): 2.97-3.02 (3H), 4.05-4.18 (2H), 4.34-4.42 (2H), 4.69-4.96 (2H), 7.88-7.91 (2H), 7.91-7.95 (1H), 8.34-8.39 (1H)

EXAMPLE 34

Experimental MH$^+$ 567.9; expected 567.9
$^1$H-NMR (CDCl3): 3.43-3.47 (6H), 4.09-4.20 (2H), 5.36-5.44 (1H), 6.58-6.65 (1H), 7.89-7.93 (2H)

EXAMPLE 35

Experimental MH$^+$ 507.9; expected 508.0
$^1$H-NMR (CDCl3): 3.43-3.46 (6H), 4.08-4.12 (2H), 7.39-7.41 (2H)

EXAMPLE 36

Experimental MH$^+$ 566.9; expected 566.9
$^1$H-NMR (CDCl3): 2.91-2.94 (3H), 3.10-3.13 (3H), 4.23-4.32 (2H), 4.62-4.66 (2H), 6.65-6.69 (1H), 7.91-7.93 (2H)

EXAMPLE 37

Experimental MH$^+$ 489.9; expected 490.0
$^1$H-NMR (CDCl3): 3.43-3.46 (6H), 4.09-4.13 (2H), 6.56-6.65 (1H), 7.30-7.32 (2H)

EXAMPLE 38

N-{5-amino-3-cyano-1-[2,6-dichloro-4-pentafluorothiophenyl]-1H-pyrazol-4-yl}methanesulfonamide

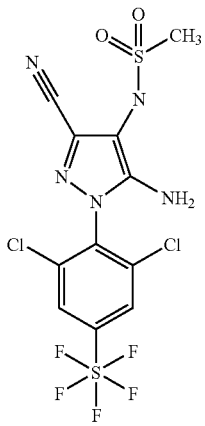

To a solution of Preparation 3 (121 mg, 0.23 mmol) in dioxane (4 ml) and methanol (1 ml) was added hydrochloric acid (5N, 0.5 ml). The reaction mixture was then heated at 90° C. for 5 h. The reaction mixture was concentrated in vacuo and the residue was partitioned between ethyl acetate (5 ml) and water (5 ml). The two layers were separated and the aqueous layer was extracted with ethyl acetate (2×5 ml). The combined organic phases were dried (MgSO$_4$) and concentrated in vacuo. The crude product was dissolved in acetonitrile/dimethyl sulphoxide (1:1, 0.15 ml) and the solution was purified by automated preparative liquid chromatography (Gilson system, 150 mm×30 mm Phenomonex LUNA II 10 μm C18 column) using an acetonitrile:water gradient [50:50 to 95:5]. The appropriate fractions were concentrated in vacuo to give the titled compound (63 mg).

Experimental MH+ 471.8; expected 472.0

¹H-NMR (CDCl3): 3.10-3.13 (3H), 4.25-4.31 (2H), 5.98-6.01 (1H), 7.89-7.92 (2H)

EXAMPLE 39

N-{5-amino-3-cyano-1-[2,6-dichloro-4-pentafluorothiophenyl]-1H-pyrazol-4-yl}-N-{[1-(trifluoromethyl)cyclopropyl]methyl}methanesulfonamide

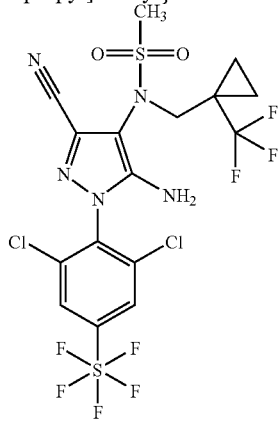

To a solution of Preparation 25 (155 mg, 0.24 mmol) in dioxane (3 ml) and methanol (1 ml) was added hydrochloric acid (5N, 0.5 ml). The reaction mixture was then heated at 90° C. for 5 h. The reaction mixture was concentrated in vacuo and the residue was partitioned between ethyl acetate (6 ml) and water (6 ml). The organic phase was separated, dried (MgSO4) and concentrated in vacuo. The crude product was dissolved in acetonitrile/dimethyl sulphoxide (1:1, 1.2 ml) and the solution was purified by automated preparative liquid chromatography (Gilson system, 150 mm×30 mm Phenomonex LUNA II 10 μm C18 column) using an acetonitrile:water gradient [60:40 to 95:5]. The appropriate fractions were concentrated in vacuo to give the titled compound (72 mg).

Experimental MH+ 593.9; expected 594.0

¹H-NMR (CDCl3): 0.61-0.87 (2H), 0.99-1.06 (2H), 3.00-3.04 (3H), 3.44-3.64 (1H), 4.14-4.38 (3H), 7.89-7.93 (2H)

EXAMPLE 40

N-{5-amino-3-cyano-1-[2,6-dichloro-4-pentafluorothiophenyl]-1H-pyrazol-4-yl}-N-(methylsulfonyl)methanesulfonamide

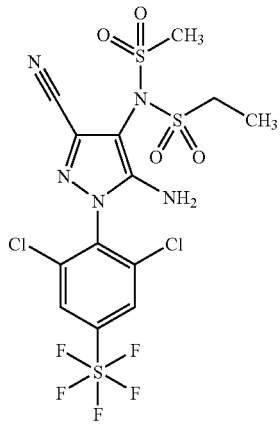

To a mixture of Example 38 (200 mg, 0.42 mmol) and ethanesulphonyl chloride (0.11 ml, 1.20 mmol) in acetonitrile (12 ml) was added potassium carbonate (116 mg, 0.84 mmol). The reaction mixture was then stirred at room temperature for 66 h. The reaction mixture was concentrated in vacuo and the residue was partitioned between water (20 ml) and ethyl acetate (20 ml). The two layers were separated and the organic layer was dried (MgSO4) and concentrated in vacuo. The residue was dissolved in acetonitrile/water (9:1, 4 ml) and the solution was purified by automated preparative liquid chromatography (Gilson system, 150 mm×30 mm Phenomonex LUNA II 10 μm C18 column) using an acetonitrile:water gradient [55:45 to 95:5]. The appropriate fractions were concentrated in vacuo to give the titled compound (143 mg).

Experimental MH+ 563.9; expected 563.9

¹H-NMR (DMSO): 1.31-1.37 (3H), 3.45-3.49 (3H), 3.53-3.68 (2H), 6.74-6.81 (2H), 8.40-8.44 (2H)

EXAMPLE 41 methyl 5-amino-3-cyano-1-[2,6-dichloro-4-(trifluoromethyl)phenyl]-1H-pyrazol-4-yl(methylsulfonyl)carbamate

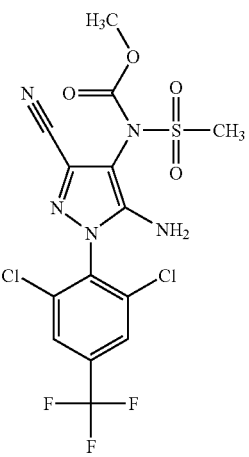

To a solution of Example 15 (100 mg, 0.24 mmol) in acetone (4 ml) was added potassium carbonate (50 mg, 0.36 mmol) and methyl chloroformate (22.4 μl, 0.29 mmol). The reaction mixture was then heated at reflux for 3 h. The reaction mixture was concentrated in vacuo and the residue was partitioned between dichloromethane and water. The two layers were separated and the aqueous layer was extracted with dichloromethane (×3). The combined organic layers were then dried (MgSO4) and concentrated in vacuo. The crude product was dissolved in acetonitrile/water (4:1, 5 ml) and purified by automated preparative liquid chromatography (Gilson system, 150 mm×30 mm Phenomenex LUNA C18(2) 10 μm column) using an acetonitrile:water gradient [50:50 to 95:5]. The appropriate fractions were concentrated in vacuo to give the titled compound (90 mg).

Experimental MH+ 471.8; expected 472.0

¹H-NMR (CD3OD): 3.50-3.52 (3H), 3.85-3.86 (3H), 7.96-8.00 (2H)

EXAMPLE 42

N-{5-amino-3-cyano-1-[2,6-dichloro-4-pentafluorothiophenyl]-1H-pyrazol-4-yl}-N-methylmethanesulfonamide

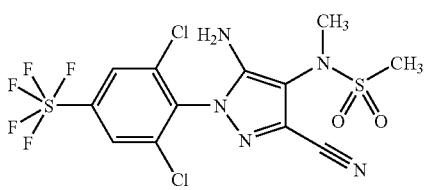

To a mixture of Example 38 (200 mg, 0.42 mmol) and methyl iodide (52 μl, 0.84 mmol) in acetonitrile (12 ml) was added potassium carbonate (116 mg, 0.84 mmol). The reaction mixture was then stirred at room temperature for 66 h. The reaction mixture was partitioned between hydrochloric acid (1M) and ethyl acetate and the two layers were separated. The organic layer was washed with water, dried (MgSO$_4$) and concentrated in vacuo. The residue was dissolved in acetonitrile/water (9:1, 8 ml) and the solution was purified by automated preparative liquid chromatography (Gilson system, 150 mm×30 mm Phenomonex LUNA II 10 μm C18 column) using an acetonitrile:water gradient [50:50 to 95:5]. The appropriate fractions were concentrated in vacuo to give the titled compound (54 mg).

Experimental MH$^+$ 485.8; expected 486.0
$^1$H-NMR (DMSO): 2.99-3.03 (3H), 3.14-3.17 (3H), 6.40-6.46 (2H), 8.41-8.44 (2H)

Similarly prepared from Example 38 were:

| Ex | R4 |
|---|---|
| 43 | 2-fluoroethyl |
| 44 | 1,2,4-oxadiazol-3-ylmethyl |
| 45 | aminocarbonylmethyl |
| 46 | 1H-pyrazol-3-ylmethyl |
| 47 | 2,2,3,3,3-pentafluoropropyl |
| 48 | 2-pyrrolidin-1-ylethyl |
| 49 | 2-morpholin-4-ylethyl |

EXAMPLE 43

Experimental MH$^+$ 517.9; expected 518.0
$^1$H-NMR (DMSO): 3.01-3.06 (3H), 3.61-3.93 (2H), 4.38-4.44 (1H), 4.50-4.56 (1H), 6.44-6.51 (2H), 8.41-8.44 (2H)

EXAMPLE 44

Experimental MH$^+$ 553.9; expected 554.0
$^1$H-NMR (DMSO): 3.12-3.14 (3H), 4.69-5.03 (2H), 6.54-6.59 (2H), 8.40-8.43 (2H), 9.61-9.63 (1H)

EXAMPLE 45

Experimental MH$^+$ 528.9; expected 529.0
$^1$H-NMR (DMSO): 2.28-2.31 (3H), 3.46-3.57 (2H), 4.00-4.01 (2H), 7.36-7.38 (2H)

EXAMPLE 46

Experimental MH$^+$ 552.0; expected 552.0
$^1$H-NMR (CDCl3): 3.15-3.20 (3H), 4.90-4.97 (2H), 5.43-5.57 (2H), 6.40-6.43 (1H), 7.61-7.65 (1H), 7.87-7.90 (2H)

EXAMPLE 47

Experimental MH$^+$ 603.9; expected 604.0
$^1$H-NMR (CDCl3): 3.10-3.14 (3H), 4.20-4.27 (2H), 7.90-7.93 (2H)

EXAMPLE 48

Experimental MH$^+$ 569.0; expected 569.0
$^1$H-NMR (CDCl3): 1.67-1.83 (4H), 2.41-2.76 (6H), 3.08-3.15 (3H), 3.51-3.99 (2H), 5.02-5.30 (2H), 7.88-7.91 (2H)

EXAMPLE 49

Experimental MH$^+$ 585.0; expected 585.0
$^1$H-NMR (CDCl3): 2.41-2.55 (4H), 2.56-2.59 (4H), 3.09-3.14 (3H), 3.61-3.73 (4H), 4.72-4.91 (2H), 7.88-7.91 (2H)

EXAMPLE 50

N-{5-amino-3-cyano-1-[2,6-dichloro-4-pentafluorothiophenyl]-1H-pyrazol-4-yl}-N-[(1-methyl-1H-imidazol-2-yl)methyl]methanesulfonamide

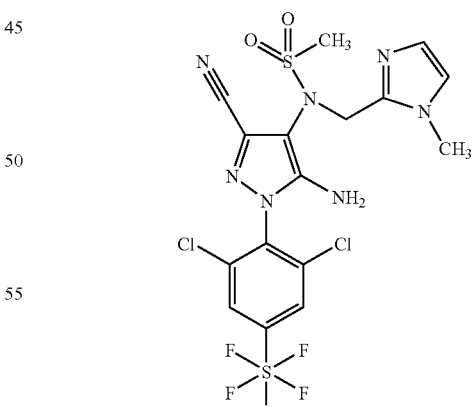

To a mixture of Example 38 (200 mg, 0.42 mmol) and 1-(N-methyl)-2-chloromethylimidazole (106 mg, 0.64 mmol) in acetonitrile (12 ml) was added potassium carbonate (116 mg, 0.84 mmol). The reaction mixture was then stirred at 40° C. for 18 h. To the reaction mixture was added water (6 ml) and ethyl acetate (10 ml). The two layers were separated and the aqueous layer was extracted with ethyl acetate (2×5 ml). The combined organic phases were then dried (MgSO₄) and concentrated in vacuo. The residue was dissolved in acetonitrile/water (3 ml) and the solution was purified by automated preparative liquid chromatography (Gilson system, 150×50 mm, LUNA II C18 10 μm column) using an acetonitrile:water gradient [45:55 to 95:5]. The appropriate fractions were concentrated to give the titled compound (98 mg).

Experimental MH⁺ 565.9; expected 566.0

¹H-NMR (CDCl3): 2.88-2.91 (3H), 3.70-3.74 (3H), 4.80-5.03 (2H), 6.09-6.18 (2H), 6.87-6.89 (1H), 6.92-6.95 (1H), 7.87-7.90 (2H)

EXAMPLE 51

N-{5-amino-3-cyano-1-[2,6-dichloro-4-pentafluorothiophenyl]-1H-pyrazol-4-yl}-N-[(5-methylisoxazol-3-yl)methyl]methanesulfonamide

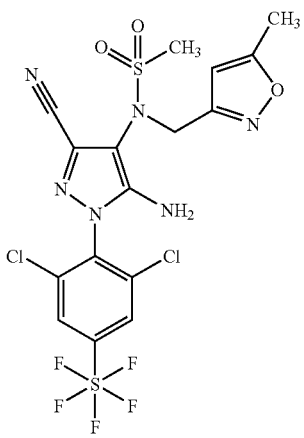

To a mixture of Example 38 (200 mg, 0.42 mmol) and 3-chloromethyl-5-methylisoxazole (84 mg, 0.64 mmol) in acetonitrile (12 ml) was added potassium carbonate (116 mg, 0.84 mmol). The reaction mixture was then stirred at 40° C. for 18 h. To the reaction mixture was added water (6 ml) and ethyl acetate (10 ml). The two layers were separated and the aqueous layer was extracted with ethyl acetate (2×5 ml). The combined organic phases were dried (MgSO₄) and concentrated in vacuo to give a mixture of products. The residue was dissolved in acetonitrile/water (3.1 ml) and the solution was purified by automated preparative liquid chromatography (Gilson system, 150×50 mm, LUNA II C18 10 μm column) using an acetonitrile:water gradient [50:50 to 95:5]. The appropriate fractions were concentrated to give the titled compound (144 mg).

Experimental MH⁺ 566.9; expected 567.0

¹H-NMR (CDCl3): 2.35-2.39 (3H), 3.11-3.15 (3H), 4.41-4.49 (2H), 4.81-4.87 (2H), 6.01-6.04 (1H), 7.86-7.89 (2H)

EXAMPLE 52

[{5-amino-3-cyano-1-[2,6-dichloro-4-pentafluorothiophenyl]-1H-pyrazol-4-yl}(methylsulfonyl)amino]methyl pivalate

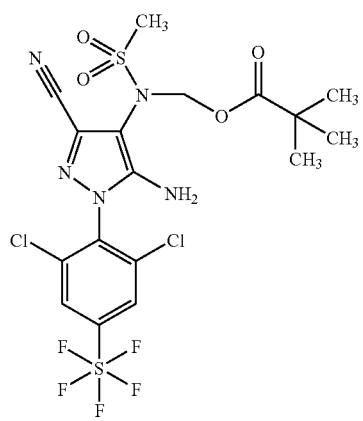

To a solution of Example 26 (200 mg, 0.36 mmol) and potassium carbonate (150 mg, 1.08 mmol) in acetonitrile (5 ml) was added chloromethyl pivalate (0.16 ml, 1.08 mmol) and potassium iodide (10 mg). The reaction mixture was then heated at 50° C. for 16 h. The reaction mixture was passed through a silica plug, eluting with methanol/dichloromethane [5:95]. The filtrate was then concentrated in vacuo. The residue was dissolved in acetonitrile (1.5 ml) and purified by automated preparative liquid chromatography (Gilson system, 150 mm×30 mm Phenomonex LUNA C18(2) 10 μm column) using an acetonitrile:water gradient [55:45 to 95:5]. The appropriate fractions were concentrated in vacuo to give the titled compound (24 mg).

Experimental MH⁺ 586.0; expected 586.0

¹H-NMR (CDCl3): 1.27-1.30 (9H), 3.21-3.23 (3H), 4.22-4.27 (2H), 5.58-5.61 (2H), 7.92-7.95 (2H)

EXAMPLE 53

N-{5-amino-3-cyano-1-[2,6-dichloro-4-pentafluorothiophenyl]-1H-pyrazol-4-yl}-N-ethylmethanesulfonamide

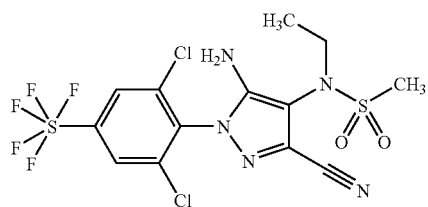

To a mixture of Example 38 (200 mg, 0.42 mmol) and ethyl iodide (67 μl, 0.84 mmol) in acetonitrile (12 ml) was added potassium carbonate (116 mg, 0.84 mmol). The reaction mixture was then stirred at room temperature for 66 h. The reaction mixture was partitioned between hydrochloric acid (1M) and ethyl acetate and the two layers were separated. The organic layer was washed with water, dried (MgSO₄) and concentrated in vacuo. The residue was dissolved in acetonitrile/water (9:1, 6 ml) and the solution was purified by automated preparative liquid chromatography (Gilson system, 150 mm×30 mm Phenomonex LUNA II 10 µm C18 column) using an acetonitrile:water gradient [60:40 to 95:5]. The appropriate fractions were concentrated in vacuo to give the titled compound (147 mg).

Experimental MH+ 499.9; expected 500.0

$^1$H-NMR (DMSO): 1.03-1.08 (3H), 2.99-3.02 (3H), 3.46-3.54 (2H), 6.41-6.45 (2H), 8.41-8.44 (2H)

EXAMPLE 54

N-{5-amino-3-cyano-1-[2,6-dichloro-4-pentafluorothiophenyl]-1H-pyrazol-4-yl}-N-benzylmethanesulfonamide

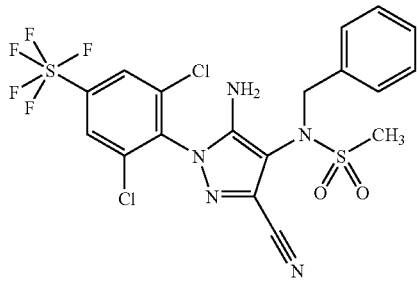

To a mixture of Example 38 (200 mg, 0.42 mmol), potassium carbonate (116 mg, 0.84 mmol) and potassium iodide (140 mg, 0.84 mmol) in acetonitrile (12 ml) was added benzyl bromide (100 µl, 0.84 mmol). The reaction mixture was then stirred at room temperature for 16 h. The reaction mixture was partitioned between hydrochloric acid (2M) and dichloromethane and the two layers were separated. The organic layer was dried (MgSO$_4$) and concentrated in vacuo. The residue was dissolved in acetonitrile/water (4 ml) and the solution was purified by automated preparative liquid chromatography (Gilson system, 150×50 mm, LUNA II C18 10 µm column) using an acetonitrile:water gradient [55:45 to 9:5]. The appropriate fractions were concentrated to give the titled compound (285 mg).

Experimental MH+ 561.9; expected 562.0

$^1$H-NMR (DMSO): 3.10-3.14 (3H), 4.46-4.82 (2H), 6.38-6.45 (2H), 7.22-7.28 (5H), 8.34-8.41 (2H)

EXAMPLE 55

N-{5-amino-3-cyano-1-[2,6-dichloro-4-pentafluorothiophenyl]-1H-pyrazol-4-yl}-N-(4-fluorobenzyl)methanesulfonamide

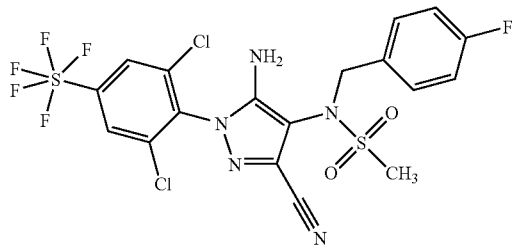

To a mixture of Example 38 (200 mg, 0.42 mmol), potassium carbonate (116 mg, 0.84 mmol) and potassium iodide (140 mg, 0.84 mmol) in acetonitrile (12 ml) was added 4-fluorobenzyl bromide (105 µl, 0.84 mmol). The reaction mixture was then stirred at room temperature for 16 h. The reaction mixture was partitioned between hydrochloric acid (2M) and dichloromethane and the two layers were separated. The organic layer was dried (MgSO$_4$) and concentrated in vacuo. The residue was dissolved in acetonitrile/water (3 ml) and the solution was purified by automated preparative liquid chromatography (Gilson system, 150×50 mm, LUNA II C18 10 µm column) using an acetonitrile:water gradient [55:45 to 95:5]. The appropriate fractions were concentrated to give the titled compound (269 mg).

Experimental MH+ 580.0; expected 580.0

$^1$H-NMR (DMSO): 3.10-3.14 (3H), 4.43-4.81 (2H), 6.38-6.45 (2H), 7.08-7.14 (2H), 7.24-7.29 (2H), 8.36-8.41 (2H)

EXAMPLE 56

N-{5-amino-3-cyano-1-[2,6-dichloro-4-(trifluoromethyl)phenyl]-1H-pyrazol-4-yl}-1-(methylsulfonyl)ethanesulfonamide

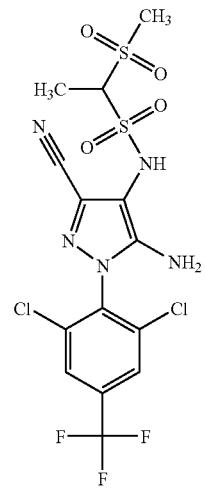

To a solution of Example 9 (90 mg, 0.18 mmol) in acetone (3 ml) was added methyl iodide (11 µl, 0.18 mmol) and potassium carbonate (20 mg). The reaction mixture was then stirred at room temperature overnight. The reaction mixture was concentrated in vacuo and the residue was partitioned between ethyl acetate (3 ml) and water (3 ml). The organic phase was then separated, dried and concentrated in vacuo. The crude product was dissolved in a mixture of acetonitrile (0.5 ml) and dimethyl sulphoxide (0.3 ml) and purified by automated preparative liquid chromatography (Gilson system, 150 mm×30 mm Phenomonex LUNA II C18 10µ column) using an acetonitrile:water gradient [10:90 to 98:2]. The appropriate fractions were concentrated in vacuo to give the titled compound (21 mg).

$^1$H-NMR (DMSO): 1.55-1.60 (3H), 3.21-3.22 (3H), 5.20-5.26 (1H), 6.38-6.49 (2H), 8.22-8.24 (2H)

EXAMPLE 57

N-{5-amino-1-[2-chloro-4-pentafluorothio-phenyl]-3-cyano-1H-pyrazol-4-yl}-N-(methylsulfonyl)methanesulfonamide

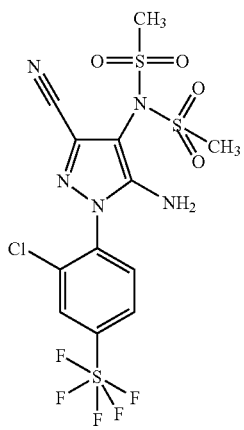

To a solution of Example 26 (50 mg, 0.09 mmol) in tetrahydrofuran (10 ml), under nitrogen, was added ethylmagnesium bromide (3M in tetrahydrofuran, 0.09 ml, 0.27 mmol). The reaction mixture was then stirred under nitrogen, at room temperature, overnight. The reaction mixture was quenched by addition of methanol and the mixture was concentrated in vacuo. The residue was partitioned between dichloromethane and water and the organic phase was separated, dried and concentrated in vacuo. The residue was dissolved in acetonitrile/water (1.5 ml) and the solution was purified by automated preparative liquid chromatography (Gilson system, 150×30 mm, LUNA II C18 10 μm column) using an acetonitrile:water gradient [45:55 to 98:2]. The appropriate fractions were concentrated to give the titled compound (3 mg).

Experimental MH$^+$ 515.9; expected 516.0

$^1$H-NMR (DMSO): 3.50-3.54 (6H), 6.70-6.74 (2H), 7.87-7.91 (1H), 8.08-8.12 (1H), 8.39-8.41 (1H)

Alternative Synthesis

To a solution of Preparation 28 (680 mg, 1.89 mmol) in dichloromethane (20 ml) was added triethylamine (1.52 ml, 7.56 mmol), followed by methanesulphonyl chloride (870 mg, 7.56 mmol). The reaction mixture was then stirred overnight at room temperature. The reaction mixture was washed with hydrochloric acid (1N, 50 ml) and the organic phase was separated, dried (MgSO$_4$) and concentrated in vacuo. The residue was dissolved in acetonitrile/water (2 ml) and the solution was purified by automated preparative liquid chromatography (Gilson system, 150 mm×30 mm LUNA II C18 10 μm column) using an acetonitrile:water gradient [50:50 to 95:5]. The appropriate fractions were combined and concentrated to give the titled compound (37 mg).

Experimental MH$^+$ 514.1; expected 514.0

$^1$H-NMR (DMSO): 3.50-3.54 (6H), 6.70-6.74 (2H), 7.87-7.91 (1H), 8.08-8.12 (1H), 8.39-8.41 (1H)

EXAMPLE 58

5-amino-1-[2,6-dichloro-4-pentafluorothiophenyl]-4-(1,1-dioxido-1,2-thiazinan-2-yl)-1H-pyrazole-3-carbonitrile

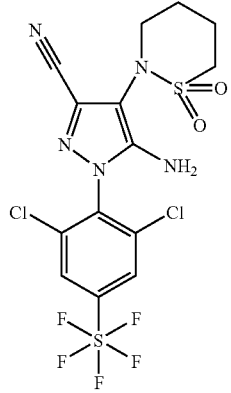

To a solution of Preparation 43 (350 mg, 0.89 mmol) in pyridine (5 ml) was added 4-chlorobutane-1-sulfonyl chloride (WO 2004050619 A1, 254 mg, 1.33 mmol). The reaction mixture was then stirred at room temperature for 18 h. The reaction mixture was partitioned between dichloromethane (20 ml) and water (20 ml) and the organic phase was separated, dried and concentrated in vacuo. To the residue was added N,N-dimethylformamide (5 ml) and potassium carbonate (123 mg, 0.89 mmol). The mixture was then heated at 85° for 60 h. The reaction mixture was concentrated in vacuo and the residue was partitioned between dichloromethane (25 ml) and water (25 ml). The organic phase was separated, dried and concentrated in vacuo. The residue was dissolved in acetonitrile/water (9:1, 2 ml) and the solution was purified by automated preparative liquid chromatography (Gilson system, 150×30 mm, LUNA II C18 10 μm column) using an acetonitrile:water gradient [50:50 to 9:5]. The appropriate fractions were concentrated to give the titled compound (28 mg).

Experimental MH$^+$ 511.9; expected 512.0

$^1$H-NMR (CDCl3): 1.98-2.02 (2H), 2.30-2.36 (2H), 3.26-3.30 (2H), 3.73-3.77 (2H), 4.13-4.22 (2H), 7.87-7.90 (2H)

EXAMPLE 59

N-{5-(benzylamino)-3-cyano-1-[2,6-dichloro-4-pentafluorothiophenyl]-1H-pyrazol-4-yl}-N-(methylsulfonyl)methanesulfonamide

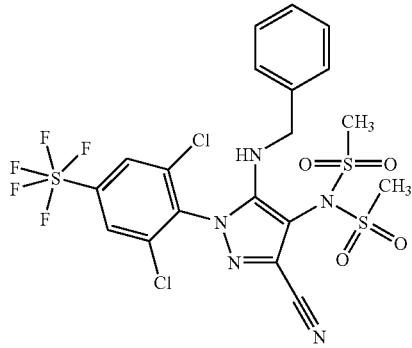

To a solution of Preparation 44 (120 mg, 0.18 mmol) in ethanol (5 ml), at 0° C., was added sodium borohydride (14 mg, 0.36 mmol). The reaction mixture was then allowed to warm to room temperature over 2 h. To the reaction mixture was added hydrochloric acid (2N, 5 ml), followed by water (10 ml) and ethyl acetate (15 ml). The two layers were separated and the aqueous layer was extracted with ethyl acetate (3×15 ml). The combined organic phases were then washed with brine, dried (MgSO₄) and concentrated in vacuo. The residue was dissolved in acetonitrile/dimethyl sulphoxide (8:2, 2 ml) and the solution was purified by automated preparative liquid chromatography (Gilson system, 150×30 mm, LUNA II C18 10 µm column) using an acetonitrile:water gradient [60:40 to 98:2]. The appropriate fractions were concentrated to give the titled compound (45 mg).

Experimental MH⁺ 639.9; expected 640.0

¹H-NMR (DMSO): 3.36-3.38 (6H), 4.41-4.44 (2H), 7.13-7.29 (6H), 8.35-8.36 (2H)

EXAMPLE 60

N-{3-cyano-1-[2,6-dichloro-4-pentafluorothiophenyl]-4-[(methylsulfonyl)(2,2,2-trifluoroethyl)amino]-1H-pyrazol-5-yl}-2-methoxyacetamide

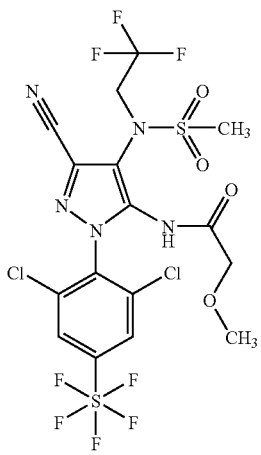

To a solution of Example 32 (200 mg, 0.36 mmol) in acetonitrile (5 ml), at 0° C., was added methoxyacetyl chloride (587 mg, 5.4 mmol) and pyridine (142 mg, 1.80 mmol). The reaction mixture was then heated at reflux for 36 h. The reaction mixture was concentrated in vacuo and the residue was partitioned between ethyl acetate and water. The organic phase was separated, washed with brine, dried (MgSO₄) and concentrated in vacuo. The residue was dissolved in acetonitrile (3 ml) and the solution was purified by automated preparative liquid chromatography (Gilson system, 150×30 mm, LUNA II C18 10 µm column) using an acetonitrile:water gradient [60:40 to 98:2]. The appropriate fractions were concentrated to give the titled compound (164 mg).

Experimental MH⁺ 625.9; expected 626.0

¹H-NMR (CDCl3): 3.12-3.15 (3H), 3.41-3.44 (3H), 3.82-3.86 (2H), 4.20-4.30 (2H), 7.83-7.86 (2H), 8.74-8.79 (1H)

EXAMPLE 61 ethyl 4-[bis(methylsulfonyl)amino]-3-cyano-1-[2,6-dichloro-4-pentafluorothiophenyl]-1H-pyrazol-5-ylimidoformate

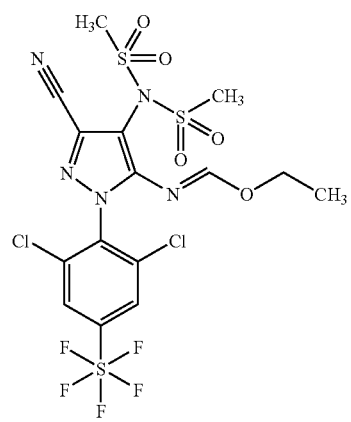

To a solution of Example 26 (200 mg, 0.36 mmol) in triethyl orthoformate (8 ml) was added hydrochloric acid (concentrated, 2 ml). The reaction mixture was then heated at 60° C. for 2 h. The reaction mixture was concentrated in vacuo and the residue was washed with toluene. The residue was dissolved in acetonitrile (2 ml) and the solution was purified by automated preparative liquid chromatography (Gilson system, 150×30 mm, LUNA II C18 10 µm column) using an acetonitrile:water gradient [55:45 to 95:5]. The appropriate fractions were concentrated to give the titled compound (104 mg).

Experimental MH⁺ 605.9; expected 606.0

¹H-NMR (CDCl3): 1.19-1.24 (3H), 3.41-3.45 (6H), 4.09-4.16 (2H), 7.84-7.87 (2H), 8.23-8.25 (1H)

EXAMPLE 62

N-{3-cyano-5-[(cyclopropylmethyl)amino]-1-[2,6-dichloro-4-pentafluorothiophenyl]-1H-pyrazol-4-yl}methanesulfonamide

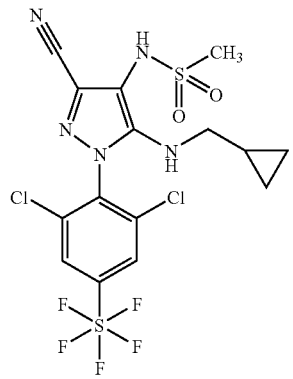

To a suspension of Example 26 (100 mg, 0.18 mmol) in toluene (4 ml) was added molecular sieves (400 mg), cyclopropanecarboxaldehyde (40 µl, 0.54 mmol) and p-toluenesul-

EXAMPLE 63

N-{3-cyano-1-[2,6-dichloro-4-pentafluorothiophenyl]-4-[(methylsulfonyl)(2,2,2-trifluoroethyl)amino]-1H-pyrazol-5-yl}acetamide

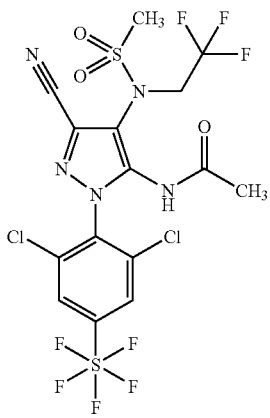

To a solution of Example 32 (50 mg, 0.09 mmol) and 4-dimethylaminopyridine (122 mg, 1.0 mmol) in dichloromethane (0.5 ml) was added acetic anhydride (0.11 ml, 1.2 mmol) and N,N-dimethylformamide (1 drop). The reaction mixture was then stirred at room temperature for 4 h. The reaction mixture was partitioned between hydrochloric acid (1M) and dichloromethane and the organic phase was separated, washed with water, dried (MgSO$_4$) and concentrated in vacuo. The residue was dissolved in acetonitrile (1.5 ml) and purified by automated preparative liquid chromatography (Gilson system, 150 mm×30 mm Phenomonex LUNA C18 (2) 10 µm column) using an acetonitrile:water gradient [55:45 to 95:5]. The appropriate fractions were concentrated in vacuo to give the titled compound (34 mg).

Experimental MH$^+$ 596.0; expected 596.0

$^1$H-NMR (DMSO): 1.94-1.98 (3H), 3.16-3.21 (3H), 4.44-4.56 (2H), 8.49-8.53 (2H), 10.38-10.42 (1H)

EXAMPLE 64

N-{3-cyano-1-[2,6-dichloro-4-pentafluorothiophenyl]-5-methoxy-1H-pyrazol-4-yl}methanesulfonamide

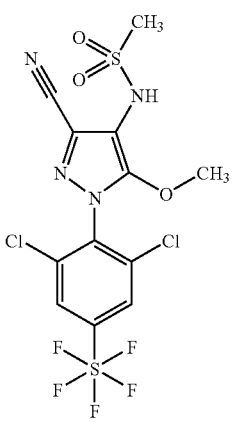

A mixture of Example 66 (140 mg, 0.25 mmol) and sodium hydroxide (1M, 0.5 ml, 0.5 mmol) in tetrahydrofuran (5 ml) was stirred at room temperature for 60 h. To the reaction mixture was added hydrochloric acid (2N, 10 ml) and the mixture was extracted with ethyl acetate (2×10 ml). The combined extracts were dried (MgSO$_4$) and concentrated in vacuo. The residue was dissolved in acetonitrile (1.5 ml) and purified by automated preparative liquid chromatography (Gilson system, 150 mm×30 mm Phenomonex LUNA C18 (2) 10 µm column) using an acetonitrile:water gradient [50:50 to 95:5]. The appropriate fractions were concentrated in vacuo to give the titled compound (67 mg).

Experimental MH$^+$ 486.8; expected 487.0

$^1$H-NMR (CDCl3): 3.19-3.22 (3H), 4.22-4.25 (3H), 5.90-5.94 (1H), 7.84-7.88 (2H)

EXAMPLE 65

N-[3-cyano-1-[2,6-dichloro-4-(trifluoromethyl)phenyl]-5-(methylamino)-1H-pyrazol-4-yl]-N-(methylsulfonyl)methanesulfonamide

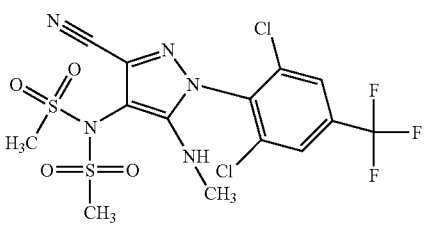

To a mixture of Preparation 30 (35 mg, 0.10 mmol) and triethylamine (28 µl, 0.20 mmol) in dichloromethane (1 ml), at 0° C., was added dropwise methanesulphonyl chloride (16 µl, 0.20 mmol). The reaction mixture was allowed to warm to room temperature and stirred for 2 h. To the reaction mixture was added dichloromethane (5 ml) and the solution was washed with hydrochloric acid (2N, 5 ml) and brine (5 ml), dried (MgSO$_4$) and concentrated in vacuo. The residue was dissolved in acetonitrile/dimethyl sulphoxide (1:1, 1 ml) and the solution was purified by automated preparative liquid chromatography (Gilson system, 250×21.2 mm, LUNA II C18 5 μm column) using an acetonitrile:water gradient [45:55 to 98:2]. The appropriate fractions were concentrated to give the titled compound (7 mg).

Experimental MH+ 505.9; expected 506.0

$^1$H-NMR (CDCl3): 2.82-2.86 (3H), 3.46-3.49 (6H), 3.78-3.86 (1H), 7.75-7.77 (2H)

Similarly prepared were:

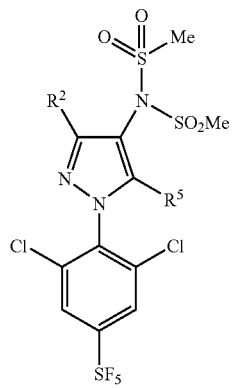

| Ex | R2 | R5 | From prep |
|---|---|---|---|
| 66 | CN | OMe | 29 |
| 67 | CN | N=CH-N(CH3)(CH3) | 33 |
| 68 | " | [2-(dimethylamino)ethyl]amino | 32 |
| 69 | " | (2-pyrrolidin-1-ylethyl)amino | 34 |
| 70 | " | (2-morpholin-4-ylethyl)amino | 31 |
| 71 | " | (2-piperidin-1-ylethyl)amino | 36 |
| 72 | cyclopropyl | NH2 | 26 |

EXAMPLE 66

$^1$H-NMR (CDCl3): 3.48-3.52 (6H), 4.07-4.10 (3H), 7.87-7.90 (2H)

EXAMPLE 67

Experimental MH+ 605.0; expected 605.0

$^1$H-NMR (CDCl3): 2.77-2.84 (3H), 2.99-3.05 (3H), 3.34-3.43 (6H), 7.78-7.84 (2H), 8.02-8.07 (1H)

EXAMPLE 68

Experimental MH+ 621.0; expected 621.0

$^1$H-NMR (CDCl3): 2.74-2.79 (6H), 3.20-3.24 (2H), 3.47-3.51 (6H), 3.75-3.81 (2H), 7.11-7.17 (1H), 7.85-7.87 (2H)

EXAMPLE 69

MS (ES): M/Z [MH+] 647.0; expected mass for C18H21Cl2F5N6O4S3+H is 647.0

$^1$H-NMR (DMSO): 1.72-1.84 (2H), 1.86-1.97 (2H), 2.85-2.95 (2H), 3.15-3.22 (2H), 3.36-3.45 (2H), 3.56-3.64 (8H), 6.88-6.93 (1H), 8.43-8.46 (2H)

EXAMPLE 70

MS (ES): M/Z [MH+] 663.1; expected mass for C18H21Cl2F5N6O5S3+H is 663.0

$^1$H-NMR (CDCl3): 2.84-2.95 (2H), 3.22-3.28 (2H), 3.37-3.44 (2H), 3.47-3.51 (6H), 3.80-3.89 (4H), 3.91-4.00 (2H), 6.56-6.68 (1H), 7.85-7.88 (2H)

EXAMPLE 71

MS (ES): M/Z [MH+] 661.0; expected mass for C19H23Cl2F5N6O4S3+H is 661.0

$^1$H-NMR (DMSO): 1.31-1.40 (1H), 1.65-1.71 (1H), 1.72-1.79 (4H), 2.80-2.90 (2H), 3.11-3.17 (2H), 3.27-3.31 (2H), 3.64-3.67 (6H), 3.67-3.73 (2H), 7.03-7.07 (1H), 8.46-8.48 (2H)

EXAMPLE 72

Experimental MH+ 565.0; expected 565.0

$^1$H-NMR (CDCl3): 0.90-0.98 (4H), 1.83-1.91 (1H), 3.41-3.45 (6H), 3.75-3.89 (2H), 7.82-7.85 (2H)

EXAMPLE 73

N-{5-amino-1-[2,6-dichloro-4-pentafluorothiophenyl]-1H-pyrazol-4-yl}methanesulfonamide

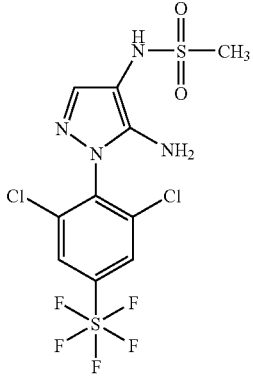

To a mixture of Preparation 27 (177 mg, 0.33 mmol) and triethylamine (115 μl, 0.83 mmol) in dichloromethane (3 ml) and tetrahydrofuran (1 ml) was added methanesulphonyl chloride (53 μl, 0.83 mmol). The reaction mixture was then stirred at room temperature for 16 h. The reaction mixture was washed with hydrochloric acid (1M) and water, dried (MgSO4) and concentrated in vacuo to give the crude product. The residue was dissolved in acetonitrile/water (1.2 ml) and the solution was purified by automated preparative liquid chromatography (Gilson system, 150×50 mm, LUNA II C18 10 μm column) using an acetonitrile:water gradient [35:65 to 95:5]. The appropriate fractions were concentrated to give the titled compound (74 mg).

¹H-NMR (CDCl3): 2.99-3.03 (3H), 3.44-3.47 (2H), 5.74-5.83 (1H), 7.53-7.56 (1H), 7.86-7.89 (2H)

Similarly prepared was:

EXAMPLE 74

N-{3-cyano-1-[2,6-dichloro-4-pentafluorothiophenyl]-5-[(pyridin-4-ylmethyl)amino]-1H-pyrazol-4-yl}methanesulfonamide

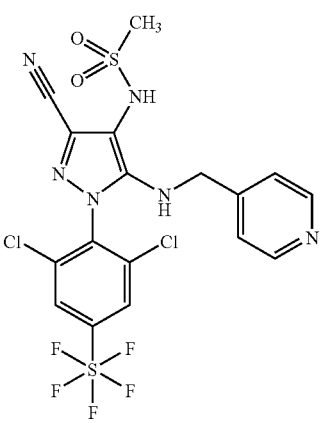

from the compound of Preparation 35 (257 mg, 0.53 mmol) and methanesulphonyl chloride (0.12 ml, 1.59 mmol) to give the title compound (13 mg).

Experimental MH⁺ 562.9; expected 563.0

¹H-NMR (DMSO): 3.03-3.06 (3H), 4.63-4.67 (2H), 7.06-7.11 (1H), 7.40-7.44 (2H), 8.47-8.49 (2H), 8.59-8.63 (2H), 9.10-9.13 (1H)

EXAMPLE 75 tert-butyl ({5-amino-3-cyano-1-[2,6-dichloro-4-pentafluorothiophenyl]-1H-pyrazol-4-yl}amino)sulfonylcarbamate

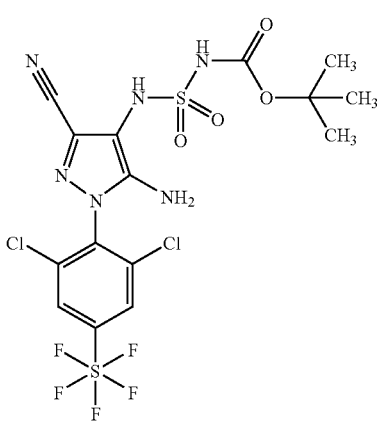

A mixture of tert-butanol (0.27 ml, 2.87 mmol) and chlorosulphonyl isocyanate (0.25 ml, 2.87 mmol) in dichloromethane (12 ml) was stirred at room temperature for 1 h, before the dropwise addition of Preparation 43 (1.13 g, 2.87 mmol) and triethylamine (0.6 ml, 4.31 mmol) in dichloromethane (12 ml). The reaction mixture was then stirred at room temperature for 2 h. The reaction mixture was partitioned between hydrochloric acid (0.5M) and dichloromethane and the organic phase was separated, washed with water, dried (MgSO₄) and concentrated in vacuo. The residue was purified by column chromatography, eluting with ethyl acetate/cyclohexane [1:9]. The appropriate fractions were combined and concentrated to give the titled compound (0.62 g).

Experimental MH⁺ 573.0; expected 573.0

¹H-NMR (DMSO): 1.36-1.41 (9H), 5.83-5.94 (2H), 8.39-8.42 (2H), 9.57-9.60 (1H), 11.07-11.11 (1H)

EXAMPLE 76

N-{5-amino-3-cyano-1-[2,6-dichloro-4-pentafluorothiophenyl]-1H-pyrazol-4-yl}-N-(2-pyridin-4-yl-ethyl)methanesulfonamide

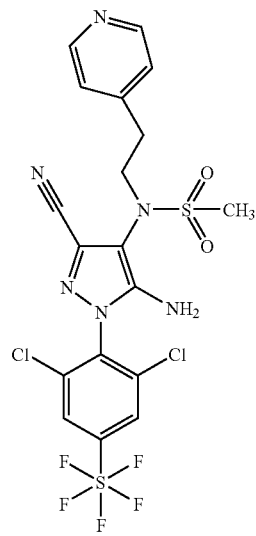

A mixture of Example 38 (200 mg, 0.42 mmol), 4-(2-hydroxyethyl)pyridine (52 mg, 0.42 mmol) and triphenylphosphine (167 mg, 0.64 mmol) in anhydrous tetrahydrofuran (5 ml) was cooled to 0° C. and diethyl azodicarboxylate (0.1 ml, 0.64 mmol) was added. The reaction mixture was warmed to room temperature and stirred under nitrogen overnight. The reaction mixture was concentrated in vacuo and the residue was partitioned between dichloromethane and water. The organic phase was then separated, dried and concentrated in vacuo. The residue was dissolved in acetonitrile/water (4 ml) and the solution was purified by automated preparative liquid chromatography (Gilson system, 150×30 mm, LUNA II C18 10 μm column) using an acetonitrile:0.1% trifluoroacetic acid gradient [35:65 to 95:5]. The appropriate fractions were concentrated to give the titled compound (55 mg).

Experimental MH⁺ 577.0; expected 577.0

¹H-NMR (CDCl3): 2.99-3.04 (3H), 3.11-3.18 (2H), 4.12-4.17 (2H), 4.19-4.41 (2H), 7.62-7.69 (2H), 7.86-7.89 (2H), 8.59-8.67 (2H)

Similarly prepared were:

EXAMPLE 77

N-{5-amino-3-cyano-1-[2,6-dichloro-4-pentafluorothiophenyl]-1H-pyrazol-4-yl}-N-(pyrazin-2-ylmethyl)methanesulfonamide

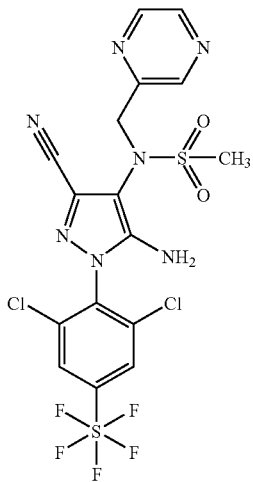

from the compound of Example 38 (200 mg, 0.42 mmol) and pyrazin-2-ylmethanol (47 mg, 0.42 mmol) to give the title compound (100 mg). Experimental MH+ 564.0; expected 564.0

$^1$H-NMR (CDCl3): 3.19-3.23 (3H), 4.98-5.06 (2H), 7.87-7.91 (2H), 8.52-8.57 (2H), 8.61-8.66 (1H)

EXAMPLE 78

N-{5-amino-3-cyano-1-[2,6-dichloro-4-pentafluorothiophenyl]-1H-pyrazol-4-yl}-N-[(6-aminopyridin-3-yl)methyl]methanesulfonamide

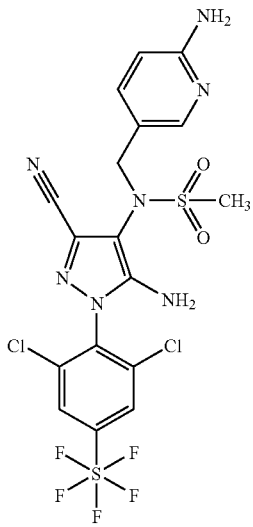

from the compound of Example 38 (200 mg, 0.42 mmol) and (6-aminopyridin-3-yl)methanol (WO 2003000682 A1, 53 mg, 0.43 mmol) to give the title compound (82 mg).

Experimental MH+ 578.0; expected 578.0

$^1$H-NMR (DMSO): 3.15-3.21 (3H), 4.34-4.47 (1H), 4.61-4.75 (1H), 6.48-6.57 (2H), 6.91-6.95 (1H), 7.69-7.73 (1H), 7.78-7.83 (1H), 7.91-8.10 (2H), 8.41-8.47 (2H)

EXAMPLE 79

N-{3-cyano-1-[2,6-dichloro-4-pentafluorothiophenyl]-1H-pyrazol-4-yl}-2-oxo-N-(2,2,2-trifluoroethyl)propane-1-sulfonamide

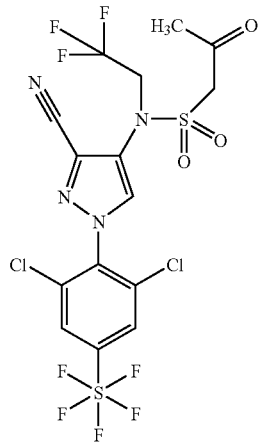

To a solution of Preparation 47 (192 mg, 0.29 mmol) in tetrahydrofuran (2 ml), at −30° C., was added dropwise isopropylmagnesium chloride (2M in tetrahydrofuran, 0.16 ml, 0.32 mmol). After 30 min, acetyl chloride (41 µl, 0.58 mmol) was added via syringe and the reaction mixture was allowed to warm to room temperature and stirred for 2 h. To the reaction mixture was added hydrochloric acid (2N, 10 ml) and the mixture was extracted with ethyl acetate (2×10 ml). The combined extracts were dried (MgSO$_4$) and concentrated in vacuo to give a mixture of products. The residue was dissolved in acetonitrile (1 ml) and purified by automated preparative liquid chromatography (Gilson system, 250 mm×30 mm Phenomonex LUNA C18(2) 10 µm column) using an acetonitrile:0.1% trifluoroacetic acid gradient [60:40 to 98:2]. The appropriate fractions were concentrated in vacuo to give a mixture of the titled compound (15 mg) and other products.

Experimental MH+ 580.9; expected 581.0

$^1$H-NMR (CDCl3): 2.36-2.39 (3H), 4.17-4.20 (2H), 4.30-4.38 (2H), 7.88-7.92 (3H)

EXAMPLE 80 hydrochloride salt of N-(3-cyano-1-[2,6-dichloro-4-pentafluorothiophenyl]-5-{[3-(dimethylamino)ethyl]amino}-1H-pyrazol-4-yl)-N-(2,2,2-trifluoroethyl)methanesulfonamide

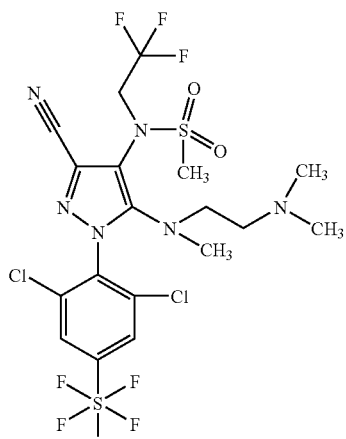

To a mixture of Preparation 40 (505 mg, 0.91 mmol) and potassium carbonate (800 mg, 5.80 mmol) in acetonitrile (10 ml) was added dropwise 2,2,2-trifluoroethyl trichloromethane sulphonate (0.30 ml, 1.83 mmol). The reaction mixture was then heated at 40° C. for 19 h. The reaction mixture was partitioned between ethyl acetate and water and the two layers were separated. The aqueous layer was extracted with ethyl acetate and the combined organic phases were washed with saturated sodium hydrogencarbonate solution and brine, dried (MgSO$_4$) and concentrated in vacuo. The residue was dissolved in acetonitrile (2 ml) and the solution was purified by automated preparative liquid chromatography (Gilson system, 150×30 mm, LUNA II C18 10 μm column) using an acetonitrile:0.1% trifluoroacetic acid gradient [40:60 to 95:5]. The appropriate fractions were concentrated to give the trifluoroacetate salt of the desired compound. A solution of the trifluoroacetate salt in dichloromethane (10 ml) was washed with saturated aqueous sodium hydrogencarbonate solution (10 ml) and brine, dried (MgSO$_4$) and concentrated in vacuo. To a solution of the residue in diethyl ether (5 ml) and methanol (1 drop) was added hydrogen chloride in diethyl ether (2 ml). The reaction mixture was then stirred for 5 min and concentrated in vacuo. To the residue was added acetonitrile (3 ml) and water (0.5 ml) and the solution was freeze-dried to give the titled compound (35 mg).

Experimental MH$^+$ 639.1; expected 639.0

$^1$H-NMR (DMSO): 2.62-2.65 (6H), 2.95-3.11 (2H), 3.29-3.30 (4H), 3.35-3.37 (3H), 4.55-4.63 (2H), 8.52-8.54 (2H)

EXAMPLE 81 hydrochloride salt of N-{3-cyano-1-[2,6-dichloro-4-pentafluorothiophenyl]-5-[(2-piperidin-1-ylethyl)amino]-1H-pyrazol-4-yl}-N-(2,2,2-trifluoroethyl)methanesulfonamide

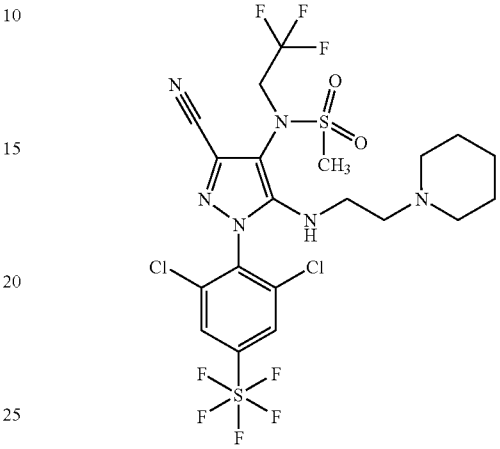

from the compound of Preparation 41 (420 mg, 0.72 mmol) and 2,2,2-trifluoroethyl trichloromethane sulphonate (0.30 ml, 1.83 mmol) to give the title compound (175 mg).

MS (ES): M/Z [MH+] 665.1; expected mass for C20H22Cl2F8N6O2S2+H is 665.1

$^1$H-NMR (DMSO): 1.63-1.74 (4H), 2.72-2.85 (2H), 3.01-3.08 (2H), 3.21-3.28 (4H), 3.30-3.33 (3H), 3.47-3.77 (2H), 4.43-4.52 (2H), 6.74-6.79 (1H), 8.41-8.45 (2H)

EXAMPLE 82

N-{5-amino-3-cyano-1-[2,6-dichloro-4-pentafluorothiophenyl]-1H-pyrazol-4-yl}sulfamide

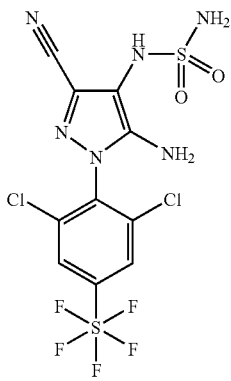

To a solution of Example 75 (150 mg, 0.26 mmol) in dichloromethane (2.4 ml), at 0° C., was added trifluoroacetic acid (0.6 ml, 7.79 mmol). The reaction mixture was then stirred at room temperature for 2.5 h. The reaction mixture was concentrated in vacuo and the residue was dissolved in acetonitrile/water (2 ml). The solution was purified by automated preparative liquid chromatography (Gilson system, 150×30 mm, LUNA II C18 10 µm column) using an acetonitrile:water gradient [40:60 to 95:5]. The appropriate fractions were concentrated to give the titled compound (77 mg).

Experimental MH+ 472.8; expected 473.0

$^1$H-NMR (DMSO): 6.02-6.07 (2H), 6.81-6.85 (2H), 8.41-8.44 (2H), 8.51-8.57 (1H)

EXAMPLE 83

N-{5-amino-3-cyano-1-[2,6-dichloro-4-(trifluoromethyl)phenyl]-1H-pyrazol-4-yl}-4-fluoro-N-(methylsulfonyl)benzenesulfonamide

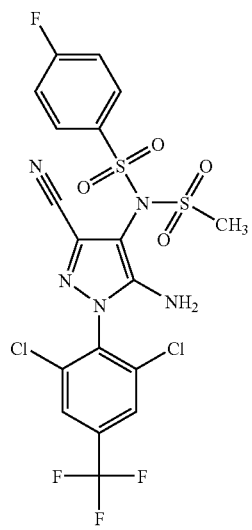

To a mixture of Example 15 (200 mg, 0.48 mmol), 4-dimethylaminopyridine (20 mg) and pyridine (0.2 ml) in dichloromethane (4 ml) was added 4-fluorobenzenesulphonyl chloride (93 mg, 0.48 mmol). The reaction mixture was then stirred overnight at room temperature. The reaction mixture was partitioned between ethyl acetate (25 ml) and water (25 ml) and the two layers were separated. The organic layer was then dried (Na$_2$SO$_4$) and concentrated in vacuo The residue was purified using an Isolute™ cartridge (silica, 25 g) with gradient elution, ethyl acetate:cyclohexane [15:85 to 1:1]. The appropriate fractions were combined and concentrated to give the titled compound (55 mg).

Experimental MH+ 571.9; expected 572.0

$^1$H-NMR (DMSO): 3.69-3.75 (3H), 6.63-6.70 (2H), 7.51-7.57 (2H), 7.89-7.95 (2H), 8.19-8.29 (2H)

Similarly prepared was:

EXAMPLE 84

N-{5-amino-3-cyano-1-[2,6-dichloro-4-(trifluoromethyl)phenyl]-1H-pyrazol-4-yl}-2,4-difluoro-N-(methylsulfonyl)benzenesulfonamide

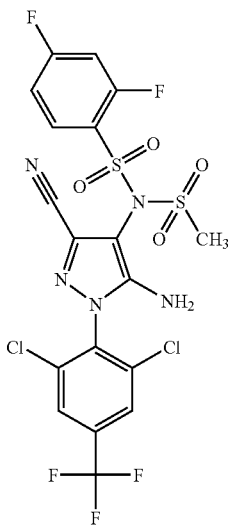

from the compound of Example 15 (200 mg, 0.48 mmol) and 2,4-difluorobenzenesulphonyl chloride (102 mg, 0.48 mmol) to give the title compound (50 mg).

Experimental MH+ 589.9; expected 590.0

$^1$H-NMR (CDCl3): 3.58-3.60 (3H), 4.26-4.34 (2H), 7.00-7.10 (2H), 7.75-7.82 (2H), 7.92-8.01 (1H)

EXAMPLE 85 methyl 3-cyano-1-[2,6-dichloro-4-pentafluorothiophenyl]-4-[(methylsulfonyl)(2,2,2-trifluoroethyl)amino]-1H-pyrazol-5-ylcarbamate

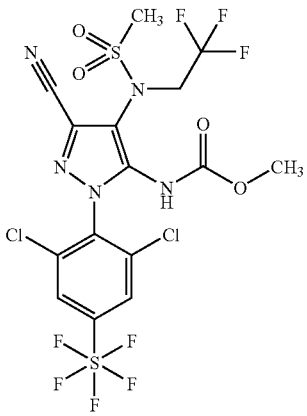

To a solution of N-{5-amino-3-cyano-1-[2,6-dichloro-4-pentafluorothiophenyl]-1H-pyrazol-4-yl}-N-(2,2,2-trifluoroethyl)methanesulfonamide (200 mg, 0.6 mmol), pyridine (73 μl, 0.90 mmol) and 3 Å molecular sieves (0.2 g) in toluene/dichloromethane (2:3, 3.6 ml), at 0° C., was added phosgene (20% in toluene, 1.7M, 2 ml). After stirring for 1 h at 0° C., methanol (2 ml) was added and the reaction mixture was allowed to warm to room temperature. The reaction mixture was concentrated in vacuo to give the crude product. The crude product was dissolved in acetonitrile/dimethyl sulphoxide (1 ml) and the solution was purified by automated preparative liquid chromatography (Gilson system, 250×30 mm, LUNA II C18 10 μm column) using an acetonitrile:0.1% trifluoroacetic acid gradient [55:45 to 95:5]. The appropriate fractions were concentrated to give the titled compound (12 mg).

Experimental MH+ 612.1; expected 612.0

$^1$H-NMR (DMSO): 3.18-3.22 (3H), 3.54-3.58 (3H), 4.44-4.60 (2H), 8.51-8.55 (2H), 10.30-10.35 (1H)

Similarly prepared were:

EXAMPLE 86

N-{5-({[(2-aminoethyl)amino]carbonyl}amino)-3-cyano-1-[2,6-dichloro-4-pentafluorothiophenyl]-1H-pyrazol-4-yl}-N-(2,2,2-trifluoroethyl)methanesulfonamide

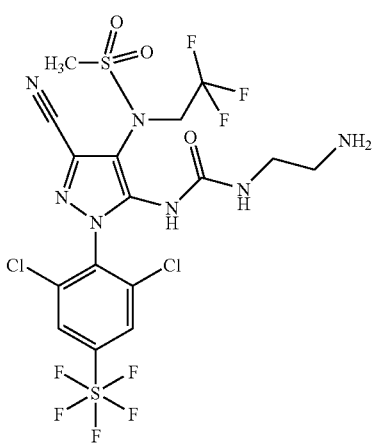

from N-{5-amino-3-cyano-1-[2,6-dichloro-4-pentafluorothiophenyl]-1H-pyrazol-4-yl}-N-(2,2,2-trifluoroethyl)methanesulfonamide (100 mg, 0.18 mmol) and ethylene diamine (1 ml) to give the title compound (12 mg).

Experimental MH+ 640.0; expected 640.0

$^1$H-NMR (CD3OD): 3.23-3.26 (3H), 3.75-3.81 (2H), 3.94-3.99 (2H), 4.11-4.14 (2H), 8.20-8.23 (2H)

EXAMPLE 87 trifluoroacetate salt of N-{5-[(2-azetidin-1-ylethyl)amino]-3-cyano-1-[2,6-dichloro-4-pentafluorothiophenyl]-1H-pyrazol-4-yl}-N-(2,2,2-trifluoroethyl)methanesulfonamide

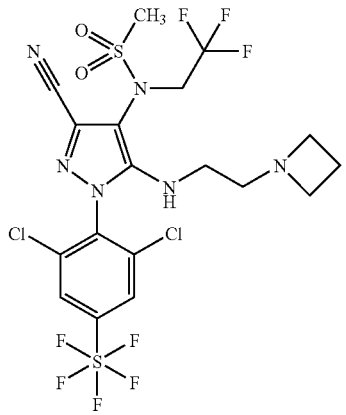

To a mixture of Preparation 48 (120 mg, 0.20 mmol), sodium triacetoxyborohydride (43 mg, 0.20 mmol) and azetidine (14 μl, 0.20 mmol) in dichloromethane (2 ml) was added acetic acid (11 μl, 0.20 mmol). The reaction mixture was then stirred at room temperature for 72 h. The reaction mixture was partitioned between aqueous sodium hydrogencarbonate solution and ethyl acetate. The organic layer was separated, dried (MgSO$_4$) and concentrated in vacuo. The residue was dissolved in acetonitrile/water (1 ml) and the solution was purified by automated preparative liquid chromatography (Gilson system, 150×30 mm, LUNA II C18 10 μm column) using an acetonitrile:0.2% trifluoroacetic acid gradient [40:60 to 95:5]. The appropriate fractions were concentrated to give the titled compound (28 mg).

Experimental MH+ 637.1; expected 637.0

$^1$H-NMR (CDCl3): 2.30-2.42 (1H), 2.58-2.71 (1H), 3.18-3.22 (3H), 3.35-3.49 (2H), 3.74-3.84 (1H), 3.85-4.00 (2H), 4.09-4.19 (1H), 4.21-4.33 (3H), 4.40-4.54 (1H), 6.54-6.63 (1H), 7.82-7.88 (2H)

EXAMPLE 88

N-(3-cyano-1-[2,6-dichloro-4-pentafluorothiophenyl]-5-{[(2,4-dihydroxyphenyl)methylene]amino}-1H-pyrazol-4-yl)-N-(2,2,2-trifluoroethyl)methanesulfonamide

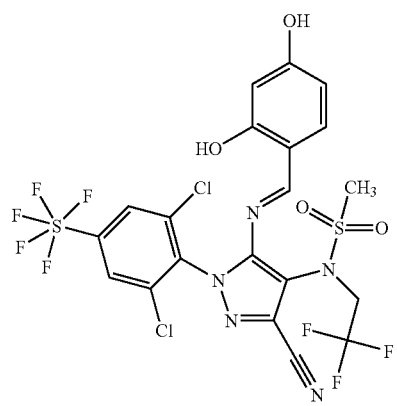

A mixture of N-{5-amino-3-cyano-1-[2,6-dichloro-4-pentafluorothiophenyl]-1H-pyrazol-4-yl}-N-(2,2,2-trifluoroethyl)methanesulfonamide (500 mg, 0.9 mmol), 2,3-dihydroxybenzaldehyde (248 mg, 1.8 mmol), molecular sieves and p-toluenesulphonic acid (17 mg) in toluene (15 ml) was heated at reflux overnight. The reaction mixture was concentrated in vacuo and the residue was washed with water, ethyl acetate and brine, dried (MgSO$_4$) and concentrated in vacuo. The residue was dissolved in acetonitrile/dimethyl sulphoxide (1 ml) and the solution was purified by automated preparative liquid chromatography (Gilson system, 150×50 mm, LUNA II C18 10 µm column) using an acetonitrile:water gradient [65:35 to 95:5]. The appropriate fractions were concentrated to give the titled compound (200 mg).

Experimental MH$^+$ 673.9; expected 674.0

$^1$H-NMR (DMSO): 3.29-3.31 (3H), 4.49-4.57 (2H), 6.13-6.17 (1H), 6.25-6.29 (1H), 7.34-7.39 (1H), 8.52-8.54 (2H), 8.87-8.90 (1H)

EXAMPLE 89

N-{5-chloro-3-cyano-1-[2,6-dichloro-4-pentafluorothiophenyl]-1H-pyrazol-4-yl}-N-(2,2,2-trifluoroethyl)methanesulfonamide

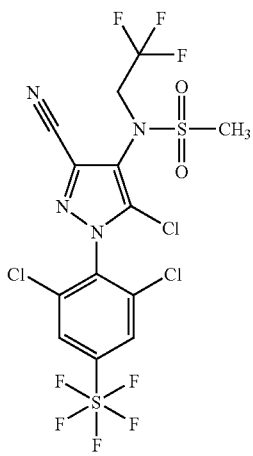

To a mixture of N-{5-amino-3-cyano-1-[2,6-dichloro-4-pentafluorothiophenyl]-1H-pyrazol-4-yl}-N-(2,2,2-trifluoroethyl)methanesulfonamide (250 mg, 0.45 mmol) and copper (II) chloride (303 mg, 2.25 mmol) in acetonitrile (5 ml) was added tert-butyl nitrite (102 µl, 0.68 mmol) in acetonitrile (1 ml). The reaction mixture was then stirred at room temperature for 3 h. The reaction mixture was concentrated in vacuo and the residue was partitioned between ethyl acetate (10 ml) and water (10 ml). The two layers were separated and the aqueous layer was extracted with ethyl acetate (10 ml). The combined organic phases were then dried (MgSO$_4$) and concentrated in vacuo. The residue was dissolved in acetonitrile (1 ml) and the solution was purified by automated preparative liquid chromatography (Gilson system, 150×30 mm, LUNA II C18 10 µm column) using an acetonitrile:water gradient [60:40 to 95:5]. The appropriate fractions were concentrated to give the titled compound (58 mg).

$^1$H-NMR (CDCl3): 3.21-3.25 (3H), 4.22-4.30 (2H), 7.90-7.93 (2H)

EXAMPLE 90

N-(3-cyano-1-[2,6-dichloro-4-pentafluorothiophenyl]-5-{[3-(dimethylamino)ethyl]amino}-1H-pyrazol-4-yl)-N-(methylsulfonyl)methanesulfonamide

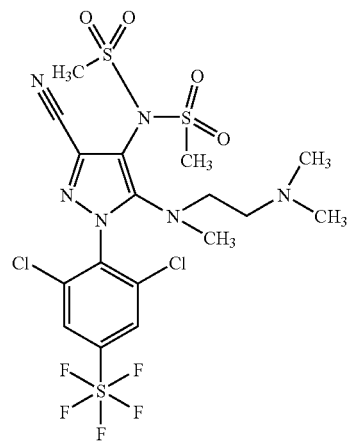

To a mixture of Preparation 33 (550 mg, 1.0 mmol) and triethylamine (0.33 ml, 2.3 mmol) in dichloromethane (15 ml), at 0° C., was added dropwise methanesulphonyl chloride (0.19 ml, 2.3 mmol). The reaction mixture was allowed to warm to room temperature and stirred for 16 h. To the reaction mixture was added water (10 ml) and the two layers were separated. The aqueous layer was extracted with dichloromethane (2×20 ml) and the combined organic phases were washed with brine, dried (MgSO$_4$) and concentrated in vacuo to the titled compound (600 mg).

Experimental MH$^+$ 635.0; expected 635.0

The following Preparations illustrate the synthesis of certain intermediates used in the preparation of the preceding Examples.

Preparation 1

N-(3-cyano-1-[2,6-dichloro-4-(trifluoromethyl)phenyl]-5-{[(dimethylamino)methylene]amino}-1H-pyrazol-4-yl)-3,4-difluorobenzenesulfonamide To a solution of Preparation 51 (200 mg, 0.51 mmol) in dichloromethane (4 ml) was added 4-dimethylaminopyridine (20 mg), pyridine (0.2 ml) and 3,4-difluorobenzenesulphonyl chloride (163 mg, 0.77 mmol). The reaction mixture was then stirred at room temperature overnight. The reaction mixture was concentrated under a stream of nitrogen to give the titled compound (200 mg), as a mixture of mono- and bis-sulphonated product.

Experimental MH$^+$ 567.1; expected 567.0

Similarly prepared from Preparation 51 (except for Preparation 4, which was prepared from Preparation 23) were:

Similarly prepared were:

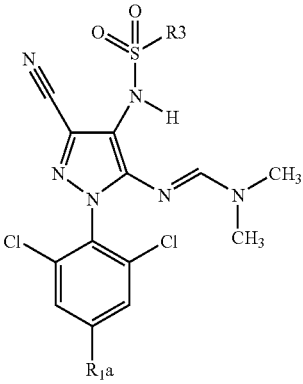

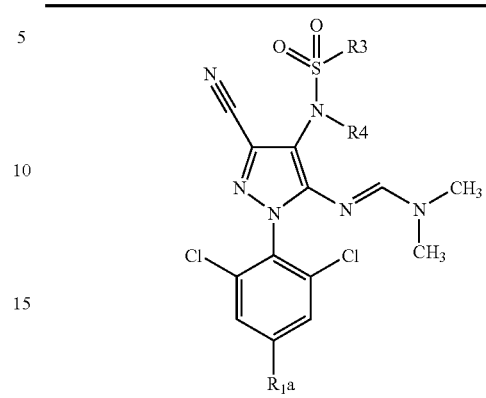

| Prep | R1a | R3 | MS (ES): M/Z [MH+] (expected mass) |
|---|---|---|---|
| 2 | CF₃ | methylsulfonylmethyl | 547.0 (547.0) |
| 3 | SF₅ | Me | 527.0 (527.0) |
| 4 | CF₃ | benzyl | 547.1 (545.1) |
| 5 | ' | 2-phenylethenyl | 555.2 (555.0) |

| Prep | R1a | R4 | R3 | From Prep no. | MS (ES): M/Z [MH+] (expected mass) |
|---|---|---|---|---|---|
| 7 | CF₃ | cyanomethyl | Me | 15 | 508.3; (508.0) |
| 8 | ' | pyridin-2-ylmethyl | Me | ' | 560.4; (560.1) |
| 9 | ' | Benzyl | Me | ' | 559.4; (559.1) |
| 10 | ' | 2-hydroxyethyl | Me | ' | 515.0; (513.1) |
| 11 | ' | methylthiomethyl | Me | ' | 531.0; (529.0) |
| 12 | ' | cyclcobutyl | trifluoromethyl | 16 | 577.0; (577.1) |
| 13 | ' | 2-N,N-dimethylamino-ethyl | Me | 15 | 540.0; (540.1) |
| 14 | SF₅ | Me | trifluoromethyl | 45 | 594.9; (595.0) |

Preparation 6

N-(3-cyano-1-[2,6-dichloro-4-(trifluoromethyl)phenyl]-5-{[(dimethylamino)methylene]amino}-1H-pyrazol-4-yl)-N-(cyclopropylmethyl)methanesulfonamide To a solution of Preparation 15 (100 mg, 0.21 mmol) in acetone (4 ml) was added iv potassium carbonate (38 mg, 0.28 mmol), followed by bromocyclopropane (25 μl, 0.26 mmol). The reaction mixture was then heated at reflux for 2 h. The reaction mixture was concentrated under nitrogen and the residue partitioned between ethyl acetate and water. The two layers were separated and the aqueous layer was extracted with ethyl acetate (×2). The combined organic phases were dried (MgSO₄) and concentrated under nitrogen to give the titled compound (100 mg).

Experimental MH⁺ 523.4; expected 523.1

Preparation 15

N-(3-cyano-1-[2,6-dichloro-4-(trifluoromethyl)phenyl]-5-{[(dimethylamino)methylene]amino}-1H-pyrazol-4-yl)methanesulfonamide To Preparation 19 (3.4 g, 6.21 mmol) in a mixture of tetrahydrofuran (35 ml) and methanol (35 ml) was added potassium carbonate (2.15 g, 15.53 mmol). The reaction mixture was then stirred at room temperature for 2 h.

The reaction mixture was concentrated in vacuo and to the residue was added ethyl acetate. The solution was washed with hydrochloric acid (1N) and brine and then concentrated in vacuo. The residue was purified by column chromatography (silica, 50 g) with gradient elution, dichloromethane:methanol [100:0 to 95:5]. The appropriate fractions were combined and concentrated to give the titled compound (620 mg).

¹H-NMR (DMSO): 2.67-2.70 (3H), 2.90-2.95 (3H), 2.99-3.02 (3H), 8.19-8.23 (2H), 8.30-8.33 (1H), 9.43-9.47 (1H)

Preparation 16

N-(3-cyano-1-[2,6-dichloro-4-(trifluoromethyl)phenyl]-5-{[(dimethylamino)methylene]amino}-1H-pyrazol-4-yl)-1,1,1-trifluoromethanesulfonamide To a solution of Preparation 46 (650 mg, 0.99 mmol) in trifluoroethanol (9 ml) was added aqueous sodium hydroxide solution (2.5N, 16 drops). The reaction mixture was then stirred at room temperature, under nitrogen, for 1 h. To the reaction mixture was added hydrochloric acid (2M, 2 ml) and the solution was concentrated in vacuo. The residue was partitioned between ethyl acetate (20 ml) and water (20 ml)

and the two phases were separated. The organic phase was washed with water (2×20 ml), dried (Na$_2$SO$_4$) and concentrated in vacuo to give the titled compound (505 mg).

Experimental MW 523.2; expected 523.0

Preparation 17

N-(3-cyano-1-[2,6-dichloro-4-(trifluoromethyl)phenyl]-5-{[(dimethylamino)methylene]amino}-1H-pyrazol-4-yl)-N-(methylsulfonyl)cyclopropanesulfonamide To a solution of Preparation 15 (150 mg, 0.32) and triethylamine (66 µl, 0.48 mmol) in dichloromethane (3 ml) was added cyclopropanesulphonyl chloride (35 mg, 0.48 mmol). The reaction mixture was then stirred at room temperature overnight. The reaction mixture was concentrated in vacuo and the residue was purified using an Isolute™ cartridge (silica, 10 g) with gradient elution, cyclohexane:ethyl acetate [3:1 to 1:1]. The appropriate fractions were combined and concentrated to give the titled compound (150 mg).

Experimental MW 572.9; expected 573.0

Similarly prepared were:

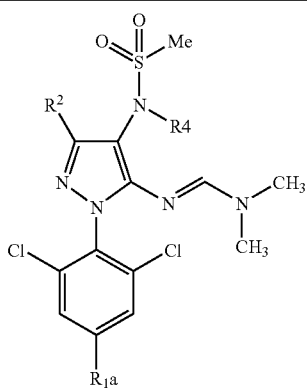

| Prep | R1a | R2 | R4 | From prep | MS (ES): M/Z [MH+] (expected mass) |
|------|-----|-----|-----|-----------|-----------|
| 18 | CF$_3$ | CN | N,N-dimethylamino sulfonyl | 15 | 575.9; (576.0) |
| 19 | ' | ' | methylsulfonyl | 51 | 547.4; (547.1) |
| 20 | SF$_5$ | CF$_3$ | ' | 71 | 647.9; (648.0) |
| 21 | OCF$_3$ | CN | ' | 72 | 578.9; (579.0) |
| 22 | OCHF$_2$ | ' | ' | 73 | 544.9; (545.0) |

Preparation 23

N'-{4-amino-3-cyano-1-[2,6-dichloro-4-pentafluorothiophenyl]-1H-pyrazol-5-yl}-N,N-dimethylimidoformamide To a solution of Preparation 53 (9.0 g, 15.15 mmol) in tetrahydrofuran (120 ml) was added tetrabutylammonium fluoride (60.6 ml, 60.6 mmol) over 5 min. The reaction mixture was heated at 50° C. for 1 h and then allowed to cool to room temperature. The reaction mixture was concentrated in vacuo and the residue was partitioned between ethyl acetate (200 ml) and water (200 ml). The organic layer was separated, washed with water (2×200 ml) and brine (200 ml), dried (MgSO$_4$) and concentrated in vacuo. The residue was purified by column chromatography (silica, 250 g) with gradient elution, ethyl acetate:dichloromethane [0:1 to 1:4]. The appropriate fractions were combined and concentrated to give the titled compound (2.6 g).

Experimental MH$^+$ 449.0; expected 449.0

Alternative Synthesis

A solution of Preparation 55 (10.0 g, 21.0 mmol) in methanol (300 ml) was placed under a hydrogen atmosphere (50 psi), with platinum (5% on charcoal, 1 g), at room temperature for 2 h. The reaction mixture was filtered and concentrated in vacuo and the residue was triturated with diethyl ether. The solution was concentrated in vacuo to give the titled compound (8.5 g).

$^1$H-NMR (CDCl3): 2.74-2.78 (3H), 2.96-2.99 (3H), 7.76-7.81 (2H), 8.18-8.21 (1H)

Preparation 24

N-(3-cyano-1-[2,6-dichloro-4-pentafluorothiophenyl]-5-{[(dimethylamino)methylene]amino}-1H-pyrazol-4-yl)-N-(2,2,2-trifluoroethyl)methanesulfonamide To a solution of Preparation 3 (239 mg, 0.45 mmol) in 1-methyl-2-pyrrolidinone (4 ml) was added sodium hydride (60% in oil, 12 mg, 0.50 mmol). The mixture was stirred at room temperature for 5 min and 2,2,2-trifluoroethyltrichloromethane sulphonate (166 mg, 0.59 mmol) was added. The reaction mixture was then stirred overnight at room temperature. To the reaction mixture was added brine (10 ml) and the mixture was adjusted to pH 4 by addition of hydrochloric acid (2N). The mixture was extracted with ethyl acetate (2×10 ml) and the combined extracts were dried (MgSO$_4$) and concentrated in vacuo. The residue was purified by column chromatography (silica) eluting with ethyl acetate/hexane [1:3]. The appropriate fractions were combined and concentrated to give the titled compound (82 mg).

Experimental MH$^+$ 609.0; expected 609.0

Preparation 25

N-(3-cyano-1-[2,6-dichloro-4-pentafluorothiophenyl]-5-{[(dimethylamino)methylene]amino}-1H-pyrazol-4-yl)-N-{[1-(trifluoromethyl)cyclopropyl]methyl}methanesulfonamide To a solution of Preparation 3 (147 mg, 0.28 mmol) in acetonitrile (6 ml) was added Preparation 52 (107 mg, 0.36 mmol) in acetonitrile (2 ml), followed by caesium carbonate (91 mg, 0.59 mmol) and potassium iodide (catalytic amount). The reaction mixture was then heated at reflux for 5 h. The reaction mixture was concentrated in vacuo and the residue was partitioned between water (10 ml) and ethyl acetate (15 ml). The two layers were separated and the aqueous layer was adjusted to pH 1 by addition of hydrochloric acid (2N) and re-extracted with ethyl acetate (10 ml). The combined organic phases were dried (MgSO$_4$) and concentrated in vacuo. The residue was purified by column chromatography (silica) with gradient elution, ethyl acetate:hexane [1:4 to 1:2]. The appropriate fractions were combined and concentrated to give the titled compound (155 mg).
Experimental MH$^+$ 649.0; expected 649.0

Preparation 26

3-cyclopropyl-1-[2,6-dichloro-4-pentafluorothiophenyl]-1H-pyrazole-4,5-diamine

To a solution of Preparation 56 (150 mg, 0.30 mmol) in ethanol (5 ml) was added tin(II) chloride (288 mg, 1.52 mmol). The reaction mixture was heated at reflux for 6 h, cooled and hydrochloric acid (6N, 0.5 ml) was added. The reaction mixture was then heated at reflux for a further 16 h. To the reaction mixture was added ethyl acetate (25 ml), water and saturated aqueous sodium hydrogencarbonate solution. The two layers were separated and the organic layer was dried (MgSO$_4$) and concentrated in vacuo to give the titled compound as a mixture of products.
Experimental MH$^+$ 409.0; expected 409.01
Similarly prepared were:

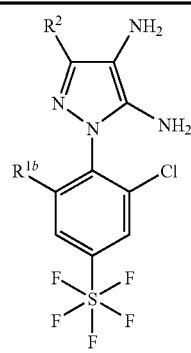

| Prep | R1b | R2 | From prep no. | MS (ES): M/Z [MH+] (expected mass) |
|---|---|---|---|---|
| 27 | Cl | H | 57 | 369.0; (369.0) |
| 28 | H | CN | 58 | 360.0; (360.0) |

Preparation 29

4-amino-1-[2,6-dichloro-4-pentafluorothiophenyl]-5-methoxy-1H-pyrazole-3-carbonitrile To a solution of Preparation 59 (530 mg, 1.21 mmol) in ethanol (10 ml) was added tin(II) chloride (1.14 g, 6.05 mmol), followed by hydrochloric acid (6N, 1 ml). The reaction mixture was then heated at reflux for 2 h. The reaction mixture was concentrated in vacuo and to the residue was added ethyl acetate (40 ml). The solution was then washed with water (30 ml) and brine (30 ml), dried (MgSO$_4$) and concentrated in vacuo to give the titled compound (495 mg).
Experimental MH$^+$ 408.9; expected 409.0

Preparation 30

4-amino-1-[2,6-dichloro-4-(trifluoromethyl)phenyl]-5-(methylamino)-1H-pyrazole-3-carbonitrile To a solution of Preparation 65 (40 mg, 0.11 mmol) in ethanol (2.5 ml) was added iron powder (57 mg, 1.0 mmol), calcium chloride (13 mg, 0.11 mmol) and water (0.5 ml). The reaction mixture was heated at reflux for 6 h and then stirred at room temperature for 8 h. The reaction mixture was filtered through Celite®, washing through with ethyl acetate, and the filtrate was concentrated in vacuo. To the residue was added ethyl acetate and the solution was washed with saturated aqueous sodium hydrogencarbonate solution (10 ml) and brine (10 ml), dried (MgSO$_4$) and concentrated in vacuo to give the titled compound (35 mg).
Experimental MH$^+$ 349.9; expected 350.0
Similarly prepared were:

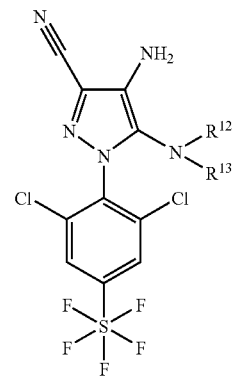

| Prep | R3a | R4a | From prep | MS (ES): M/Z [MH+] (expected mass) |
|---|---|---|---|---|
| 31 | H | 2-morpholin-4-ylethyl | 66 | 507.0; (507.1) |
| 32 | H | 2-N,N-dimethylaminoethyl | 67 | 465.1; (465.1) |
| 33 | Me | 2-N,N-dimethylaminoethyl | 70 | 479.0; (479.1) |
| 34 | H | 2-pyrrolidin-1-ylethyl | 68 | 491.0; (491.1) |
| 35 | H | Pyridin-4-ylmehtyl | 60 | 485.0; (485) |
| 36 | H | 2-piperidin-1-ylethyl | 69 | 505.0; (505.1) |

Preparation 37

4-[bis(methylsulfonyl)amino]-1-[2,6-dichloro-4-pentafluorothiophenyl]-5-{[(dimethylamino)methylene]amino}-1H-pyrazole-3-carboxamide Hydrogen chloride was bubbled through methanol (8 ml) for 10 min. To the solution was added Example 67 (441 mg, 0.73 mmol) and the flow of hydrogen chloride was maintained for a further 5 min. The reaction mixture was then sealed and left overnight. The reaction mixture was concentrated in vacuo and to the residue was added methanol (20 ml) and hydrochloric acid (2N, 10 ml). The mixture was stirred for 1 h and water (30 ml) was added. The mixture was extracted with ethyl acetate (3×20 ml) and the combined extracts were dried (MgSO$_4$) and concentrated in vacuo to give the titled compound (450 mg) as a 20:1 mixture of the amide and the methyl ester. Experimental MH$^+$ 623.0; expected 623.0

Preparation 38

N-(3-acetyl-1-[2,6-dichloro-4-pentafluorothiophenyl]-5-{[(dimethylamino)methylene]amino}-1H-pyrazol-4-yl)-N-(methylsulfonyl)methanesulfonamide To a solution of Example 67 (500 mg, 0.83 mmol) in tetrahydrofuran (10 ml), at 0° C., was added dropwise methylmagnesium bromide (3M in diethyl ether, 0.8 ml, 2.48 mmol). The reaction mixture was then stirred at room temperature for 2 days. The reaction mixture was poured onto ice, water and hydrochloric acid (2N). The mixture was stirred for 30 min and then extracted with ethyl acetate (3×30 ml). The combined extracts were dried (MgSO$_4$) and concentrated in vacuo. The residue was dissolved in acetonitrile (2 ml) and the solution was purified by automated preparative liquid chromatography (Gilson system, 150×30 mm, LUNA II C18 10 μm column) using an acetonitrile:water gradient [50:50 to 95:5]. The appropriate fractions were concentrated to give the titled compound (97 mg).
Experimental MH$^+$ 622.0; expected 622.0

Preparation 39

N-{5-amino-3-cyano-1-[2,6-dichloro-4-(trifluoromethoxy)phenyl]-1H-pyrazol-4-yl}methanesulfonamide To a solution of Example 35 (120 mg, 0.24 mmol) in tetrahydrofuran (5 ml) was added aqueous sodium hydroxide solution (1M, 4.25 ml) and the reaction mixture was stirred at room temperature for 2 h. The reaction mixture was acidified by addition of hydrochloric acid (1M) and then extracted with dichloromethane. The combined extracts were dried (Na$_2$SO$_4$) and concentrated in vacuo to give the titled compound (100 mg).
Experimental MH$^+$ 429.9; expected 430.0
Similarly prepared were:

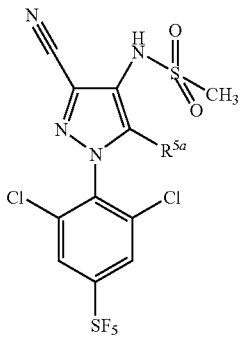

| Prep | R5a | From prep | MS (ES): M/Z [MH+] (expected mass) |
|---|---|---|---|
| 40 | (2-(dimethylamino)ethyl)(methyl)amino | 111 | 557.0; (557.0) |
| 41 | (2-piperidin-1-ylethyl)amino | Ex 71 | 583.0; 583.1 |

Preparation 42

N-(3-cyano-1-[2,6-dichloro-4-pentafluorothiophenyl]-5-{[(dimethylamino)methylene]amino}-1H-pyrazol-4-yl)-N-[2-(1H-1,2,4-triazol-1-yl)ethyl]methanesulfonamide To a mixture of Preparation 74 (154 mg, 0.24 mmol) and 1,2,4-triazole (42 mg, 0.61 mmol) in acetonitrile (10 ml) was added potassium carbonate (40 mg, 0.29 mmol). The reaction mixture was then heated at 60° C. overnight. The reaction mixture was concentrated in vacuo and the residue was partitioned between dichloromethane (10 ml) and water (10 ml). The organic phase was separated, dried (MgSO$_4$) and concentrated in vacuo to give the titled compound (155 mg).
Experimental MH$^+$ 622.0; expected 622.0

Preparation 43

4,5-diamino-1-[2,6-dichloro-4-pentafluorothiophenyl]-1H-pyrazole-3-carbonitrile

To a solution of Preparation 23 (300 mg, 0.67 mmol) in methanol (8 ml) and dioxane (1 ml) was added hydrochloric acid (2M, 8 ml). The reaction mixture was then heated at reflux overnight. The reaction mixture was concentrated in vacuo and the residue was partitioned between ethyl acetate and water. The organic layer was separated, dried (MgSO$_4$) and concentrated in vacuo to give the titled compound (273 mg).
Experimental MH$^+$ 394.0; expected 394.0

Preparation 44

N-(3-cyano-1-[2,6-dichloro-4-pentafluorothiophenyl]-5-{[phenylmethylene]amino}-1H-pyrazol-4-yl)-N-(methylsulfonyl)methanesulfonamide To a solution of Example 26 (100 mg, 0.18 mmol) in toluene (5 ml) was added benzaldehyde (0.04 ml, 0.36 mmol), p-toluenesulphonic acid (catalytic amount) and some 4 A molecular sieves. The reaction mixture was heated at 90° C. for 8 h and then stirred at room temperature for 15 h. The reaction mixture was concentrated in vacuo and the residue was partitioned between ethyl acetate (10 ml) and water (10 ml). The two layers were separated and the aqueous layer was extracted with ethyl acetate (2×10 ml). The combined organic phases were washed with brine, dried (MgSO$_4$) and concentrated in vacuo to give the titled compound (120 mg).
Experimental MH$^+$ 637.9; expected 638.0

Preparation 45

N-(3-cyano-1-[2,6-dichloro-4-pentafluorothiophenyl]-5-{[(dimethylamino)methylene]amino}-1H-pyrazol-4-yl)-1,1,1-trifluoromethanesulfonamide To a solution of Preparation 23 (200 mg, 0.45 mmol) in anhydrous dichloromethane (5 ml), at 0° C., was added triethylamine (124 μl, 0.89 mmol) and trifluoromethanesulphonic anhydride (150 μl, 0.89 mol). The reaction mixture was then stirred under nitrogen for 30 min. To the reaction mixture was added dichloromethane and hydrochloric acid (4M, 3 ml). The organic phase was separated, washed with hydrochloric acid (4M) and brine, dried (Na$_2$SO$_4$) and concentrated in vacuo. The residue was purified by column chromatography (silica, 25 g) with gradient elution, ethyl acetate:cyclohexane [2:1 to 1:0], followed by methanol. The appropriate fractions were combined and concentrated to give the titled compound (200 mg).
Experimental MH$^+$ 580.9; expected 581.0
Similarly prepared was:

Preparation 46

N-(3-cyano-1-[2,6-dichloro-4-(trifluoromethyl)phenyl]-5-{[dimethylamino)methylene]amino}-1H-pyrazol-4-yl)-N, N-bis-(1,1,1-trifluoromethane)sulphonamide, from Preparation 51 (800 mg, 2.05 mmol) and trifluoromethanesulphonic anhydride (860 μl, 2.05 mol) to give the title compound (1.3

Experimental MH+ 655.3; expected 655.0

Preparation 47

N-{3-cyano-1-[2,6-dichloro-4-pentafluorothiophenyl]-5-iodo-1H-pyrazol-4-yl}-N-(2,2,2-trifluoroethyl)methanesulfonamide To a mixture of Example 32 (447 mg, 0.81 mmol) and iodine (881 mg, 3.47 mmol) in acetonitrile (10 ml) was added isoamylnitrite (0.13 ml, 0.97 mmol). The reaction mixture was then heated at 50° C. for 1 h. To the reaction mixture was added saturated aqueous sodium thiosulphate solution (30 ml) and the mixture was extracted with ethyl acetate (2×20 ml). The combined extracts were washed with brine (50 ml), dried (MgSO$_4$) and concentrated in vacuo. The residue was dissolved in acetonitrile (2 ml) and purified by automated preparative liquid chromatography (Gilson system, 150 mm×50 mm Phenomonex LUNA C18(2) 10 μm column) using an acetonitrile:water gradient [55:45 to 95:5]. The appropriate fractions were concentrated in vacuo to give the titled compound (283 mg).

$^1$H-NMR (CDCl3): 3.24-3.28 (3H), 4.07-4.20 (1H), 4.35-4.49 (1H), 7.90-7.93 (2H)

Preparation 48

N-{3-cyano-1-[2,6-dichloro-4-pentafluorothiophenyl]-5-[(2-oxoethyl)amino]-1H-pyrazol-4-yl}-N-(2,2,2-trifluoroethyl)methanesulfonamide To a solution of Preparation 75 (560 mg, 0.94 mmol) in aqueous acetone (10%, 16.6 ml) was added osmium tetroxide solution (2.5%, 33 μmol). To the mixture was added sodium periodate (880 mg, 2.07 mmol) and the reaction mixture was stirred at room temperature overnight. The reaction mixture was filtered and the filtrate was concentrated in vacuo. The residue was partitioned between dichloromethane and water and the organic layer was separated, dried (MgSO$_4$) and concentrated in vacuo to give the titled compound (134 mg).

$^1$H-NMR (CDCl3): 3.17-3.20 (3H), 4.20-4.29 (2H), 4.32-4.46 (2H), 4.76-4.81 (1H), 7.91-7.93 (2H), 9.58-9.59 (1H)

Preparation 49

N-(3-cyano-1-[2,6-dichloro-4-(trifluoromethyl)phenyl]-5-{[(dimethylamino)methylene]amino}-1H-pyrazol-4-yl)-1,1,1-trifluoro-N-methylmethanesulfonamide To a solution of Preparation 46 (1.3 g, 1.98 mmol) in tetrahydrofuran (11 ml), at 0° C., was added potassium carbonate (685 mg, 4.96 mmol) in methanol (11 ml) and water (3 drops). The reaction mixture was then stirred at room temperature for 2 h. The reaction mixture was concentrated in vacuo and to the residue was added dichloromethane. The solution was washed with hydrochloric acid (1N) and brine, dried (MgSO$_4$) and concentrated in vacuo. The residue was purified by column chromatography (silica, 50 g) with gradient elution, cyclohexane:dichloromethane [1:0 to 0:1], followed by dichloromethane:methanol [95:5]. The appropriate fractions were combined and concentrated to give the titled compound (240 mg).

$^1$H-NMR (CDCl3): 2.79-2.85 (3H), 3.02-3.08 (3H), 3.45-3.51 (3H), 7.69-7.74 (2H), 8.02-8.07 (1H)

Preparation 50

N'-[3-cyano-1-[2,6-dichloro-4-(trifluoromethyl)phenyl]-4-(1,1-dioxidoisothiazolidin-2-yl)-1H-pyrazol-5-yl]-N,N-dimethylimidoformamide A mixture of Preparation 76 (127 mg, 0.24 mmol) and potassium carbonate (36 mg, 0.26 mmol) in N,N-dimethylformamide (2 ml) was stirred at room temperature for 2 h. To the reaction mixture was added ethyl acetate (10 ml) and water (10 ml) and the two layers were separated. The aqueous layer was extracted with ethyl acetate (×2) and the combined organic phases were dried (MgSO$_4$) and concentrated in vacuo to give the titled compound (110 mg).

Experimental MH+ 495.2; expected 495.0

Preparation 51

N'-{4-amino-3-cyano-1-[2,6-dichloro-4-(trifluoromethyl)phenyl]-1H-pyrazol-5-yl}-N,N-dimethylimidoformamide To a solution of Preparation 77 (423 mg, 0.79 mmol) in tetrahydrofuran (15 ml) was added tetrabutylammonium fluoride (1M in tetrahydrofuran, 3.2 ml, 3.2 mmol). The reaction mixture was then heated at 50° C. for 1 h. The reaction mixture was concentrated in vacuo and the residue partitioned between dichloromethane (20 ml) and water (20 ml). The organic phase was separated, dried (MgSO$_4$) and concentrated in vacuo. The residue was purified by column chromatography with gradient elution, ethyl acetate:hexane [1:2 to 4:1]. The appropriate fractions were combined and concentrated to give the titled compound (220 mg, 71%).

Experimental MH+ 391.2; expected 391.1

Alternative Synthesis

A solution of Preparation 61 (1.20 g, 2.85 mmol) in methanol (25 ml) was placed under a hydrogen atmosphere (15 psi), with platinum (5% on charcoal), at room temperature for 3 h. The reaction mixture was filtered through a pad of Arbocel®, washing through with dichloromethane/methanol and the filtrate was concentrated in vacuo. The residue was purified using an Isolute™ cartridge (silica, 25 g), eluting with dichloromethane/methanol [99:1]. The appropriate fractions were combined and concentrated to give the titled compound (1.0 g).

Experimental MH+ 391.1; expected 391.1

Preparation 52

[1-(trifluoromethyl)cyclopropyl]methyl 4-methylbenzenesulfonate

To a solution of 1-(trifluoromethyl)cyclopropyl]methanol (J. Fluorine Chem., 2001, 109, 2, 95, 8.18 g, 58.4 mmol) in dichloromethane (50 ml), at 0° C., was added triethylamine (50 ml), 4-dimethylaminopyridine (713 mg, 5.84 mmol) and p-toluenesulphonyl chloride (11.1 g, 58.4 mmol). The reaction mixture was allowed to warm to room temperature and stirred overnight. The reaction mixture was concentrated in vacuo and the residue was partitioned between diethyl ether (250 ml) and hydrochloric acid (0.5M, 100 ml). The two layers were separated and the aqueous phase was extracted with diethyl ether (100 ml). The combined organic phases were washed with saturated aqueous sodium hydrogencarbonate solution (50 ml) and brine (50 ml), dried (MgSO$_4$) and concentrated in vacuo. The residue was purified using a Biotage™ Flash 40 system with gradient elution, diethyl ether:cyclohexane [5:95 to 20:80]. The appropriate fractions were combined and concentrated to give the titled compound (11.8 g).

$^1$H-NMR (CDCl3): 0.81-0.89 (2H), 1.09-1.16 (2H), 2.44-2.48 (3H), 4.09-4.12 (2H), 7.33-7.39 (2H), 7.77-7.82 (2H)

Preparation 53

2-(trimethylsilyl)ethyl 3-cyano-1-[2,6-dichloro-4-pentafluorothiophenyl]-5-{[(dimethylamino)methylene]amino}-1H-pyrazol-4-ylcarbamate To a solution of Preparation 78 (6.7 g, 14.0 mmol), triethylamine (2.14 ml, 15.4 mmol) and 2-trimethylsilylethanol (2.21 ml, 15.4 mmol) in 1,4-dioxane (100 ml) was added diphenylphosphoryl azide (3.34 ml, 15.4 mmol). The reaction mixture was heated at reflux for 3 h and then stirred overnight at room temperature. To the reaction mixture was added ethyl acetate (200 ml) and the mixture was washed with hydrochloric acid (1M, 2×250 ml). The aqueous phase was re-extracted with ethyl acetate (200 ml) and the organic phases were combined, washed with brine (200 ml), dried (Na$_2$SO$_4$) and concentrated in vacuo. The residue was purified by column chromatography (silica, 300 g) with gradient elution, methanol:dichloromethane [0:100 to 5:95]. The appropriate fractions were combined and concentrated to give the titled compound (9.0 g).

Experimental MH$^+$ 593.0; expected 593.1

Similarly prepared was:

Preparation 54

2-(trimethylsilyl)ethyl 1-[2,6-dichloro-4-pentafluorothiophenyl]-5-{[(dimethylamino)methylene]amino}-3-(trifluoromethyl)-1H-pyrazol-4-ylcarbamate from the compound of Preparation 80 (1.22 g, 2.35 mmol), diphenylphosphoryl azide (0.56 ml, 2.59 mmol) and 2-silylethanol (0.37 ml, 2.59 mmol) to give the title compound (0.91 g).

Experimental MH$^+$ 636.0; expected 636.1

Preparation 55

N-{3-cyano-1-[2,6-dichloro-4-pentafluorothiophenyl]-4-nitro-1H-pyrazol-5-yl}-N,N-dimethylimidoformamide To a solution of nitronium tetrafluoroborate (470 mg, 3.5 mmol) in acetonitrile (15 ml) was added Preparation 81 (1.0 g, 2.9 mmol). The reaction mixture was then stirred at room temperature for 2 h. The reaction mixture was diluted with ethyl acetate, washed with water and saturated brine solution, dried (MgSO$_4$) and concentrated in vacuo to give the titled compound (960 mg).

Experimental MH$^+$ 478.8; expected 479.0

Similarly prepared were:

| prep | R1a | R1b | R2a | R3a | From prep | MS (ES): M/Z [MH+] (expected mass) |
|---|---|---|---|---|---|---|
| 56 | SF$_5$ | Cl | cyclopropyl | N=CH-N(CH$_3$)$_2$ | 82 | 494.0; (494.0) |
| 57 | " | ' | H | " | 83 | 454.0; (454.0) |
| 58 | " | H | CN | " | 84 | |
| 59 | " | Cl | " | OMe | 93 | * |
| 60 | ' | ' | " | pyridin-4-ylmethyl)amino | 94 | 514.9; (515.0) |
| 61 | CF$_3$ | ' | " | N=CH-N(CH$_3$)$_2$ | 85 | ** |
| 62 | OCF$_3$ | ' | " | " | 87 | 437.0; (437.0) |
| 63 | SCF$_3$ | ' | " | " | 88 | 453.0; (453.0) |
| 64 | OCHF$_2$ | ' | " | " | 89 | 419.0; (419.0) |

*$^1$H-NMR (CDCl3): 4.24-4.33 (3H), 7.89-7.96 (2H)
**$^1$H-NMR (DMSO): 2.73-2.77 (3H), 3.06-3.09 (3H), 8.20-8.27 (2H), 8.53-8.56 (1H)

Preparation 65

1-[2,6-dichloro-4-(trifluoromethyl)phenyl]-5-(methylamino)-4-nitro-1H-pyrazole-3-carbonitrile A mixture of 5-bromo-1-[2,6-dichloro-4-(trifluoromethyl)phenyl]-4-nitro-1H-pyrazole-3-carbonitrile (EP 295118 A1, 50 mg, 0.12 mmol) and methylamine (2M in tetrahydrofuran, 1.0 mmol, 2.0 mmol) was heated at 55° C. for 2.5 h. To the reaction mixture was added water (5 ml), followed by ethyl acetate (5 ml). The two layers were separated and the aqueous layer was extracted with ethyl acetate (3×5 ml). The combined organic phases were dried (MgSO$_4$) and concentrated in vacuo to give the titled compound (42 mg).

$^1$H-NMR (CDCl3): 2.65-2.69 (3H), 7.29-7.37 (1H), 7.76-7.80 (2H)

Similarly prepared from Preparation 92 were:

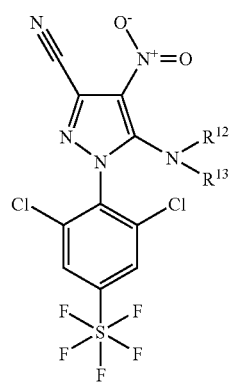

| Prep | R12 | R13 | MS (ES): M/Z [MH+] (expected mass) |
|---|---|---|---|
| 66 | H | 2-morpholin-4-ylethyl | 537.0; (537.0) |
| 67 | H | 2-(dimethylamino)ethyl | 495.0; (495.0) |
| 68 | H | 2-pyrrolidin-1-ylethyl | 521.1; (521.0) |
| 69 | H | 2-piperidin-1-ylethyl | 535.0; (535.0) |
| 70 | Me | 2-(dimethylamino)ethyl | 509.0; (509.0) |

Preparation 71

N'-[4-amino-1-[2,6-dichloro-4-pentafluorothiophenyl]-3-(trifluoromethyl)-1H-pyrazol-5-yl]-N,N-dimethylimidoformamide To a solution of Preparation 54 (0.91 g, 1.43 mmol) in tetrahydrofuran (27 ml) was added tetrabutylammonium fluoride (5.7 ml, 5.7 mmol), via syringe. The reaction mixture was then heated at 50° C. for 1 h. The reaction mixture was concentrated in vacuo and the residue was partitioned between dichloromethane and water. The organic phase was then separated, dried (MgSO$_4$) and concentrated in vacuo. The residue was purified by column chromatography with gradient elution, ethyl acetate:cyclohexane [1:4 to 2:3]. The appropriate fractions were combined and concentrated to give the titled compound (0.64 g).

Experimental MH$^+$ 491.9; expected 492.0

Preparation 72

N'-{4-amino-3-cyano-1-[2,6-dichloro-4-(trifluoromethoxy)phenyl]-1H-pyrazol-5-yl}-N,N-dimethylimidoformamide To a solution of Preparation 62 (750 mg, 1.91 mmol) in methanol was added platinum (10 wt. % on carbon) and the mixture was placed in a hydrogen atmosphere (50 psi) for 8 h. The reaction mixture was filtered through Arbocel® and the filtrate was concentrated in vacuo. The residue was partitioned between dichloromethane and water and the organic phase was separated, dried and concentrated in vacuo to give the titled compound (650 mg).

Experimental MH$^+$ 407.0; expected 407.0

Preparation 73

N'-{4-amino-3-cyano-1-[2,6-dichloro-4-(difluoromethoxy)phenyl]-1H-pyrazol-5-yl}-N,N-dimethylimidoformamide from the compound of Preparation 64 (850 mg, 2.03 mmol) to give the title compound (580 mg).

Experimental MH$^+$ 389.0; expected 389.0

Preparation 74

N-(2-bromoethyl)-N-(3-cyano-1-[2,6-dichloro-4-pentafluorothiophenyl]-5-{[(dimethylamino)methylene]amino}-1H-pyrazol-4-yl)methanesulfonamide To a mixture of Preparation 3 (166 mg, 0.32 mmol) and 1,2-dibromoethane (0.14 ml, 1.58 mmol) in acetonitrile (12 ml) was added potassium carbonate (52 mg, 0.38 mmol). The reaction mixture was then heated at 70° C. overnight. The reaction mixture was concentrated in vacuo and the residue was partitioned between dichloromethane (30 ml) and water (30 ml). The organic phase was separated, dried (MgSO$_4$) and concentrated in vacuo to give the titled compound (154 mg).

Experimental MH$^+$ 632.9; expected 632.9

Preparation 75

N-{5-(allylamino)-3-cyano-1-[2,6-dichloro-4-pentafluorothiophenyl]-1H-pyrazol-4-yl}-N-(2,2,2-trifluoroethyl)methanesulfonamide To a solution of Example 32 (3.0 g, 5.4 mmol) in tetrahydrofuran (27 ml), at 0° C., was added sodium hydride (0.24 g, 5.94 mmol). The mixture was allowed to warm to room temperature and allyl bromide (2.3 ml, 27.0 mmol) was added. The reaction mixture was then stirred at room temperature for 2 days. To the reaction mixture was added water and ethyl acetate. The organic layer was separated, dried (MgSO$_4$) and concentrated in vacuo. The residue was purified by column chromatography with gradient elution, ethyl acetate:cyclohexane [5:95 to 1:5]. The appropriate fractions were combined and concentrated to give the titled compound (1.34 g).

Experimental MH$^+$ 594.1; expected 594.0

Preparation 76

3-chloro-N-(3-cyano-1-[2,6-dichloro-4-(trifluoromethyl)phenyl]-5-{[(dimethylamino)methylene]amino}-1H-pyrazol-4-yl)propane-1-sulfonamide To a solution of Preparation 51 (100 mg, 0.26 mmol) in pyridine (2 ml), under nitrogen, was added 3-chloropropanesulphonyl chloride (34 µl, 0.28 mmol) and the reaction mixture was stirred overnight at room temperature. To the reaction mixture was added ethyl acetate (10 ml) and water (10 ml) and the two layers were separated. The aqueous layer was extracted with ethyl acetate (×2) and the combined organic phases were washed with hydrochloric acid (1M), water and brine, dried (MgSO$_4$) and concentrated in vacuo to give the titled compound (127 mg).

Experimental MH$^+$ 529.1; expected 529.0

Preparation 77

2-(trimethylsilyl)ethyl 3-cyano-1-[2,6-dichloro-4-(trifluoromethyl)phenyl]-5-{[(dimethylamino)methylene]amino}-1H-pyrazol-4-ylcarbamate To a solution of Preparation 79 (420 mg, 1.0 mmol) in 1,4-dioxane (6 ml) was added triethylamine (0.15 ml, 1.1 mmol) and 2-(trimethylsilyl)ethanol (0.16 ml, 1.1 mmol), followed by the dropwise addition of diphenylphosphoryl azide (0.24 ml, 1.1 mmol). The reaction mixture was then heated at reflux overnight. The reaction mixture was concentrated in vacuo and the residue partitioned between ethyl acetate (20 ml) and hydrochloric acid (1N, 20 ml). The organic phase was separated, dried (MgSO$_4$) and concentrated in vacuo. The residue was purified by column chromatography with gradient elution, ethyl acetate:hexane [1:2 to 2:1]. The appropriate fractions were combined and concentrated to give the titled compound (423 mg). Experimental MW 535.4; expected 535.1

Preparation 78

3-cyano-1-[2,6-dichloro-4-pentafluorothiophenyl]-5-{[(dimethylamino)methylene]amino}-1H-pyrazole-4-carboxylic acid To a solution of Preparation 95 (8.0 g, 16.25 mmol) in anhydrous pyridine (80 ml) was added lithium iodide (10.9 g, 81.25 mmol). The reaction mixture was then heated at reflux, under nitrogen, overnight. The reaction mixture was concentrated in vacuo and the residue was partitioned between ethyl acetate (200 ml) and hydrochloric acid (2N, 200 ml). The organic layer was separated, washed with hydrochloric acid (2N, 2×200 ml) and brine (200 ml), dried (Na$_2$SO$_4$) and concentrated in vacuo. The residue was purified by column chromatography (silica, 300 g) with gradient elution, methanol:dichloromethane [0.5:95.5 to 10:90]. The appropriate fractions were combined and concentrated to give the titled compound (6.7 g).

Experimental MH$^+$ 477.8; expected 478.0

Similarly prepared were:

Preparation 79

3-cyano-1-[2,6-dichloro-4-(trifluoromethyl)phenyl]-5-{[(dimethylamino)methylene]amino}-1H-pyrazole-4-carboxylic acid from the compound of Preparation 90 (2.0 g, 4.61 mmol) to give the titled compound (1.5 g).

Experimental MH$^+$ 420.2; expected 420.0

Preparation 80

1-[2,6-dichloro-4-pentafluorothiophenyl]-5-{[(dimethylamino)methylene]amino}-3-(trifluoromethyl)-1H-pyrazole-4-carboxylic acid from the compound of Preparation 91 (2.12 g, 4.1 mmol) to give the titled compound (1.22 g).

Experimental MH$^+$ 521.0; expected 521.0

Preparation 81

N'-{3-cyano-1-[2,6-dichloro-4-pentafluorothiophenyl]-1H-pyrazol-5-yl}-N,N-dimethylimidoformamide To a solution of Preparation 86 (2.2 g, 3.9 mmol) in dry tetrahydrofuran (30 ml), at −30° C., was added isopropylmagnesium chloride (2M in N,N-dimethylformamide, 2.2 ml, 4.4 mmol). The reaction mixture was then allowed to warm to room temperature over 1 h. To the reaction mixture was added saturated aqueous ammonium chloride solution (10 ml) and ethyl acetate (excess). The organic layer was separated, washed with saturated brine solution, dried (MgSO$_4$) and concentrated in vacuo to give the titled compound (1.6 g).

Experimental MH$^+$ 433.8; expected 434.0

Preparation 82

N'-{3-cyclopropyl-1-[2,6-dichloro-4-pentafluorothiophenyl]-1H-pyrazol-5-yl}-N,N-dimethylimidoformamide A solution of Preparation 96 (3.3 g, 8.40 mmol) in N,N-dimethylformamide dimethyl acetal (15 ml) was heated at reflux for 2 h. The reaction mixture was concentrated in vacuo and the residue was absorbed onto silica and purified by column chromatography, eluting with cyclohexane/ethyl acetate [4:1]. The appropriate fractions were combined and concentrated to give the titled compound (3.7 g). Experimental MH$^+$ 449.0; expected 449.0

Similarly prepared were:

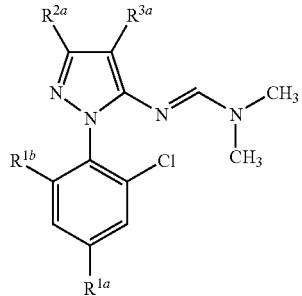

| Prep | R1a | R1b | R2a | R3a | From prep | MS (ES): M/Z [MH+] (expected mass) |
|---|---|---|---|---|---|---|
| 83 | SF$_5$ | Cl | H | H | 97 | 409.0; (409.01) |
| 84 | " | H | CN | " | 99 | 400.0; (400.0) |
| 85 | CF$_3$ | Cl | " | " | * | *** |
| 86 | SF$_5$ | " | " | I | ** | **** |
| 87 | OCF$_3$ | " | " | H | 104 | 392.0; is (392.0) |
| 88 | SCF$_3$ | " | " | " | 103 | 408.0; (408.0) |
| 89 | OCHF$_2$ | " | " | " | 106 | 374.0; (374.0) |

-continued

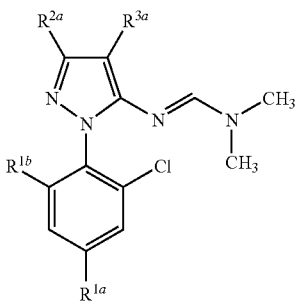

| Prep | R1a | R1b | R2a | R3a | From prep | MS (ES): M/Z [MH+] (expected mass) |
|------|-----|-----|-----|-----|-----------|-----------------------------------|
| 90 | CF₃ | " | " | —CO₂Me | 107 | 434.2; (434.1) |
| 91 | SF₅ | " | CF₃ | " | 108 | 535.0; (535.0) |

*5-amino-1-[2,6-dichloro-4-(trifluoromethyl)phenyl]-1H-pyrazole-3-carbonitrile (WO 9839302 A1)
**5-amino-1-[2,6-dichloro-4-pentafluorothiophenyl]-4-iodo-1H-pyrazole-3-carbonitrile (WO 9824761 A1, WO 9804530 A1)
***¹H-NMR (DMSO): 2.63-2.65 (3H), 2.96-2.98 (3H), 6.61-6.63 (1H), 8.13-8.15 (1H), 8.16-8.18 (2H)
****¹H-NMR (CDCl3): 2.77-2.81 (3H), 3.02-3.05 (3H), 7.78-7.81 (2H), 8.21-8.24 (1H)

Preparation 92

5-bromo-1-[2,6-dichloro-4-pentafluorothiophenyl]-4-nitro-1H-pyrazole-3-carbonitrile To a solution of Preparation 98 (5.0 g, 12.0 mmol) and bromoform (16 ml, 18.3 mmol) in acetonitrile (50 ml) was added dropwise tent-butyl nitrite (8 ml, 67.3 mmol). The reaction mixture was then heated at 55° C. for 16 h. The reaction mixture was concentrated in vacuo and the residue was re-crystallised from cyclohexane/ethyl acetate [20:1] to give the titled compound (3.1 g).
¹H-NMR (CDCl3): 7.92-7.97 (2H)

Preparation 93

1-[2,6-dichloro-4-pentafluorothiophenyl]-5-methoxy-1H-pyrazole-3-carbonitrile

To a solution of Preparation 100 (650 mg, 1.71 mmol) in acetonitrile (15 ml) was added potassium carbonate (708 mg, 5.13 mmol) and methyl iodide (0.32 ml, 5.14 mmol) and the reaction mixture was heated at 40° C. overnight. The reaction mixture was concentrated in vacuo and the residue was partitioned between water (30 ml) and ethyl acetate (30 ml). The two layers were separated and the organic layer was washed with brine (30 ml), dried (MgSO₄) and concentrated in vacuo. The residue was purified by column chromatography with gradient elution, hexane:ethyl acetate [5:1 to 3:1]. The appropriate fractions were combined and concentrated to give the titled compound (474 mg).
Experimental MH⁺ 393.9; expected 394.0

Preparation 94

1-[2,6-dichloro-4-pentafluorothiophenyl]-5-[(pyridin-4-ylmethyl)amino]-1H-pyrazole-3-carbonitrile To a mixture of 5-amino-1-[2,6-dichloro-4-pentafluorothiophenyl]-1H-pyrazole-3-carbonitrile (WO 9306089 A1, 1.00 g, 2.63 mmol) and p-toluenesulphonic acid (5 mg) in toluene (20 ml) was added 4-pyridinecarboxaldehyde (0.35 ml, 3.68 mmol). The reaction mixture was then heated at reflux for 1.5 h. The reaction mixture was partitioned between ethyl acetate and water and the organic layer was separated, washed with water, dried (MgSO₄) and concentrated in vacuo. To a solution of the residue in methanol (48 ml) was added sodium borohydride (48 mg, 1.26 mmol) and the mixture was stirred at room temperature for 2 h. The reaction mixture was concentrated in vacuo and the residue was partitioned between ethyl acetate and water. The organic layer was separated, dried (MgSO₄) and concentrated in vacuo to give the titled compound (1.26 g).
Experimental MH⁺ 470.0; expected 470.0

Preparation 95 methyl 3-cyano-1-[2,6-dichloro-4-pentafluorothiophenyl]-5-{[(dimethylamino)methylene]amino}-1H-pyrazole-4-carboxylate A mixture of Preparation 86 (50.0 g, 89.3 mmol), triethylamine (24.9 ml, 178.6 mmol) and [1,1'-bis(diphenylphosphino)ferrocene]dichloropalladium(II). dichloromethane (2.0 g) in methanol (500 ml) was heated at 65° C. under carbon monoxide (150 psi) for 8 h. To the reaction mixture was added water (2 l) and the mixture was stirred for 30 min. The precipitate was collected by filtration and air-dried to give the titled compound (43.3 g).
¹H-NMR (DMSO): 2.67-2.70 (3H), 3.00-3.03 (3H), 3.72-3.77 (3H), 8.36-8.38 (1H), 8.41-8.43 (2H)

Preparation 96

3-cyclopropyl-1-[2,6-dichloro-4-pentafluorothiophenyl]-1H-pyrazol-5-amine

To a solution of Preparation 101 (1.55 g, 14.2 mmol) in 2-propanol (30 ml) was added Preparation 102 (4.28 g, 14.2 mmol). The reaction mixture was heated at reflux for 16 h. The mixture was cooled to room temperature and concentrated sulphuric acid (0.1 ml) was added, followed by acetic acid (0.6 ml). The reaction mixture was then heated at reflux for a further 4 h. The reaction mixture was concentrated in vacuo and to the residue was added water and saturated aqueous sodium hydrogencarbonate solution (30 ml). The mixture was extracted with ethyl acetate and the combined extracts were dried (MgSO₄) and concentrated in vacuo. The residue was absorbed onto silica and purified by column chromatography with gradient elution, cyclohexane:ethyl acetate [4:1 to 2:1]. The appropriate fractions were combined and concentrated to give the titled compound (3.4 g).

Preparation 97

1-[2,6-dichloro-4-pentafluorothiophenyl]-1H-pyrazol-5-amine

To a solution of Preparation 102 (4.0 g, 13.2 mmol) and ethylenediaminetetraacetic acid disodium salt (catalytic amount) in methanol (40 ml), heated at reflux, was added 2-chloroacrylonitrile (3.2 ml, 39.6 mmol) dropwise. The reaction mixture was heated at reflux overnight, before addition of sulphuric acid (concentrated, 1.2 ml, 21.1 mmol). After heating at reflux for a further 6 h, anhydrous sodium carbonate (4.2 g, 39.6 mmol) was added and the reaction mixture was stirred overnight at room temperature. The reaction mixture was concentrated in vacuo and to the residue was added water (150 ml). The mixture was stirred for 60 h and the resulting precipitate was collected by filtration, washed with water and dried to give the titled compound (4.2 g). Experimental MH$^+$ 354.0; expected 354.0

Preparation 98

5-amino-1-[2,6-dichloro-4-pentafluorothiophenyl]-4-nitro-1H-pyrazole-3-carbonitrile To a solution of Preparation 55 (10.0 g, 20.9 mmol) in dioxane (160 ml) was added methanol (20 ml) and hydrochloric acid (10%, 20 ml). The reaction mixture was heated at 90° C. for 56 h and additional hydrochloric acid (concentrated, 2 ml) was added. The reaction mixture was then heated at 90° C. for a further 15 h. To the reaction mixture was added aqueous sodium hydrogencarbonate solution (50 ml) and ethyl acetate (100 ml). The two layers were separated and the aqueous layer was extracted with ethyl acetate (2×100 ml). The combined organic phases were washed with brine, dried (MgSO$_4$) and concentrated in vacuo. The residue was triturated with dichloromethane to give the titled compound (6.6 g).
Experimental MH$^+$ 424.0; expected 424.0

Preparation 99

5-amino-1-[2-chloro-4-pentafluorothio-phenyl]-1H-pyrazole-3-carbonitrile

To sulphuric acid (concentrated, 1.75 ml) was added carefully sodium nitrite (432 mg, 6.26 mmol), followed by glacial acetic acid (2.5 ml). The solution was stirred at 10° C. for 1 h, before Preparation 105 (1.44 g, 5.69 mmol) in glacial acetic acid (1 ml) was added dropwise. The mixture was heated at 50° C. for 1 h, allowed to cool to room temperature, and then added dropwise to ethyl 2,3-dicyanopropanoate (Hainzl, D.; Cole, L. M.; Casida, J. E. Chemical Research in Toxicology (1998), 11(12), 1529-1535, 864 mg, 5.69 mmol) in acetic acid (1 ml) and ice water (2 ml). The reaction mixture was then stirred at room temperature for 45 min. The reaction mixture was poured into water (200 ml) and the mixture was extracted with dichloromethane (100 ml). To the organic extract was added aqueous ammonium hydroxide solution (880, 25 ml) and water (25 ml) and the mixture was stirred at room temperature overnight. The reaction mixture was partitioned between dichloromethane (100 ml) and water (100 ml) and the organic phase was separated, dried (MgSO$_4$) and concentrated in vacuo to give the titled compound (700 mg).
Experimental MH$^+$ 345.1; expected 345.0

Preparation 100

1-[2,6-dichloro-4-pentafluorothiophenyl]-5-hydroxy-1H-pyrazole-3-carbonitrile

Sodium nitrite (1.32 g, 19.1 mmol) was added carefully to sulphuric acid (concentrated, 6.8 ml), whilst cooling the solution to 0° C. The solution was heated to 60° C. for 30 min, allowed to cool and then diluted with acetic acid (12 ml). To the solution was added 2,6-dichloro-4-pentafluorothiophenylamine (WO 9421606 A1, 5.0 mg, 17.4 mmol) in acetic acid (11 ml) and the reaction mixture was heated at 55° C. for 1 h. To a solution of dimethyl 2-cyanosuccinate (Hall, H. K., Jr.; Ykman, P., J. Am. Chem. Soc. (1975), 97(4), 800-807, 3.09 g, 18.1 mmol) in acetic acid (24 ml) and water (36 ml) was added dropwise the solution of the diazonium salt, followed by sodium acetate (24.2 g) in water (42 ml). The reaction mixture was then stirred at room temperature for 30 min. The reaction mixture was poured into ice/water (200 ml) and the mixture was extracted with dichloromethane (4×60 ml). The combined extracts were then washed with ammonium hydroxide (48 ml), dried and concentrated in vacuo. To a solution of sodium methoxide (25 wt. %, 11.5 ml, 50.1 mmol) in methanol (450 ml) was added dropwise a solution of the residue in methanol (100 ml). The reaction mixture was then stirred at room temperature for 2 h. The reaction mixture was concentrated in vacuo and to the residue was added water. This solution was adjusted to pH 1 by addition of hydrochloric acid (4N) and the mixture was extracted with dichloromethane (3×100 ml). The combined extracts were dried (MgSO$_4$) and concentrated in vacuo. The residue was purified by column chromatography, eluting with hexane/ethyl acetate [3:1]. The appropriate fractions were combined and concentrated to give the titled compound (4.5 g).
Experimental MH$^+$ 379.8; expected 380.0

Preparation 101

3-cyclopropyl-3-oxopropanenitrile

To a solution of cyanoacetic acid (4.25 g, 50.0 mmol) in tetrahydrofuran (80 ml) and dichloromethane (40 ml), at 0° C., was added isopropylmagnesium chloride (2M in tetrahydrofuran, 50 ml, 100 mmol). In a separate reaction vessel, 1,1-carbonyldiimidazole (4.05 g, 25.0 mmol) was added to cyclopropylcarboxylic acid (2.15 g, 25.0 mmol) in tetrahydrofuran (80 ml), at 0° C. The two mixtures were combined with additional tetrahydrofuran (60 ml) and the reaction mixture was stirred at room temperature for 60 h. To the reaction mixture was added hydrochloric acid (2N), at 0° C., and the mixture was stirred for 1 h. The mixture was concentrated in vacuo and to the residue was added water. After extracting with diethyl ether (2×100 ml), the combined extracts were washed with saturated aqueous sodium hydrogencarbonate solution (60 ml) and water (60 ml), dried (MgSO$_4$) and concentrated in vacuo to give the titled compound (1.5 g).
$^1$H-NMR (CDCl3): 1.02-1.08 (2H), 1.13-1.18 (2H), 2.03-2.09 (1H), 3.57-3.60 (2H)

Preparation 102

[2,6-dichloro-4-pentafluorothiophenyl]hydrazine

To a mixture of sulphuric acid (concentrated, 24 ml) and sodium nitrite (6.0 g, 87.0 mmol) at 10° C., was added 2,6-dichloro-4-pentafluorothiophenylamine (WO 9421606 A1, 23.5 g, 82.0 mmol) in glacial acetic acid (92 ml) over 20 min. The reaction mixture was stirred at 25° C. for 20 min and then heated at 60° C. for 1 h. The reaction mixture was cooled to 5° C. and tin (II) chloride (65.6 g, 0.35 mol) in hydrochloric acid (concentrated, 56 ml) was added. After stirring for 30 min, the precipitate was collected by filtration and added to ammonia (400 ml) and ice (100 ml). This mixture was extracted with diethyl ether (5×200 ml) and the combined extracts were dried (MgSO$_4$) and concentrated in vacuo to give the titled compound (19.3 g).
$^1$H-NMR (CDCl3): 3.61-3.82 (2H), 5.75-5.91 (1H), 7.60-7.65 (2H)

Preparation 103

5-amino-1-{2,6-dichloro-4-[(trifluoromethyl)thio]phenyl}-1H-pyrazole-3-carbonitrile Sodium nitrite (224 mg, 3.25 mmol) was added carefully to sulphuric acid (concentrated, 1 ml), ensuring that the temperature did not rise above 30° C. After stirring at 15° C. for 1 h, acetic acid (2 ml) was added, followed by Preparation 109 (850 mg, 3.24 mmol) in acetic acid (3 ml). The reaction mixture was then heated at 50° C. for 1 h and cooled to room temperature. To a solution of ethyl 2,3-dicyanopropanoate (Hainzl, D.; Cole, L. M.; Casida, J. E. Chemical Research in Toxicology (1998), 11(12), 1529-1535, 500 mg, 3.29 mmol) in acetic acid (5 ml) was added ice water (5 ml), followed by the solution of the diazonium salt, added dropwise at 0° C. After complete addition, ammonium hydroxide (6 ml) was added and the reaction mixture was stirred overnight at room temperature. The reaction mixture was filtered through Arbocel® and the filtrate was concentrated in vacuo. The residue was partitioned between dichloromethane and water and the organic phase was separated, dried ($Na_2SO_4$) and concentrated in vacuo to give the titled compound (1.0 g).

Experimental $MH^+$ 353.0; expected 353.0

Preparation 104

5-amino-1-[2,6-dichloro-4-(trifluoromethoxy)phenyl]-1H-pyrazole-3-carbonitrile To sulphuric acid (18M, 54 ml) was added sodium nitrite (13.9 g, 201.2 mmol) and the solution was stirred at 15° C. for 1 h. To the solution was added acetic acid (200 ml), followed by 2,6-dichloro-4-(trifluoromethoxy)aniline (45.0 g, 182.9 mmol) in acetic acid (90 ml), ensuring the temperature of the solution did not rise above 20° C. After addition was complete, the mixture was heated at 50° C. for 1 h, cooled to room temperature and added dropwise to a solution of ethyl 2,3-dicyanopropanoate (Hainzl, D.; Cole, L. M.; Casida, J. E. Chemical Research in Toxicology (1998), 11(12), 1529-1535, 27.8 g, 182.9 mmol) in acetic acid (115 ml) and ice cold water (145 ml). The reaction mixture was then stirred overnight at room temperature. To the reaction mixture was added dichloromethane (500 ml) and the mixture was stirred for 10 min. The two phases were separated and the organic phase was washed with water (200 ml) and ammonia (0.88, 400 ml) was added dropwise, maintaining the temperature of the mixture below 10° C. This mixture was stirred overnight at room temperature and the organic phase was separated and concentrated in vacuo. The residue was re-crystallised from toluene/pentane [2:1] to give the titled compound (22.4 g).

Experimental $MH^+$ 337.0; expected 337.0

Preparation 105

2-chloro-4-pentafluorothio-phenylamine

To a solution of 4-(pentafluorothio)phenylamine (WO 9421606 A1, 1.29 g, 5.89 mmol) in acetonitrile (15 ml) at 45° C. was added N-chlorosuccinimide (786 mg, 5.89 mmol). The reaction mixture was then stirred at 45° C. for 3 h. The reaction mixture was concentrated in vacuo and the residue was partitioned between dichloromethane (20 ml) and water (20 ml). The organic phase was separated, dried and concentrated in vacuo to give the titled compound (1.44 g).

Experimental $MH^+$ 254.1; expected 254.0

Preparation 106

5-amino-1-[2,6-dichloro-4-(difluoromethoxy)phenyl]-1H-pyrazole-3-carbonitrile To sulphuric acid (concentrated, 21 ml), at 15° C., was added sodium nitrite (4.8 g, 69.6 mmol). After stirring for 1 h, glacial acetic acid (17.3 ml) was added, followed by Preparation 110 (13.8 g, 60.3 mmol) in acetic acid (33.8 ml), added dropwise, keeping the temperature of the mixture below 25° C. The solution was heated at 50° C. for 1 h, cooled and added dropwise to a mixture of ethyl 2,3-dicyanopropanoate (Hainzl, D.; Cole, L. M.; Casida, J. E. Chemical Research in Toxicology (1998), 11(12), 1529-1535, 10.6 g, 69.6 mmol), acetic acid (42.8 ml) and ice/water (55 ml), at 0° C. The reaction mixture was then stirred at room temperature overnight. To the reaction mixture was added dichloromethane (300 ml) and the mixture was stirred. The two layers were separated and the organic layer was washed with water. To the organic layer was added ammonium hydroxide (concentrated, 125 ml) and ice and the mixture was stirred at 5° C. for 4 h. The organic layer was again separated and stirred overnight with activated charcoal. The mixture was filtered through Celite® and the filtrate was concentrated in vacuo. The residue was purified by column chromatography (Biotage, silica, 90 g), eluting with dichloromethane. The appropriate fractions were combined and concentrated to give Preparation 136 (3.1 g).

Experimental $MH^+$ 319.0; expected 319.0

Preparation 107 methyl 5-amino-3-cyano-1-[2,6-dichloro-4-(trifluoromethyl)phenyl]-1H-pyrazole-4-carboxylate A mixture of 5-amino-1-[2,6-dichloro-4-(trifluoromethyl)phenyl]-4-iodo-1H-pyrazole-3-carbonitrile (WO 9828278 A1, 18 g, 40.3 mmol), [1,1'-bis(diphenylphosphino)ferrocene]dichloropalladium(II) (600 mg) and triethylamine (10 ml), in methanol (150 ml), was placed in a pressure vessel and heated at 60° C. under carbon monoxide (100 psi) for 60 h. The reaction mixture was filtered through Celite® and the filtrate concentrated in vacuo. To the residue was added ethyl acetate and this solution was washed with hydrochloric acid (0.2M) and brine. The organic phase was then separated, dried and concentrated in vacuo. The residue was purified by flash column chromatography, eluting with ethyl acetate/hexane (1:5). The appropriate fractions were combined and concentrated and the residue re-crystallised from methanol to give the titled compound (100 mg).

Experimental $MH^+$ 379.0; expected 379.0

Preparation 108 methyl 5-amino-1-[2,6-dichloro-4-pentafluorothiophenyl]-3-(trifluoromethyl)-1H-pyrazole-4-carboxylate To a mixture of Preparation 102 (3.95 g, 13.1 mmol) and potassium carbonate (2.16 g, 15.6 mmol) in diethyl ether (15 ml), at 0° C., was added dropwise methyl (2Z)-3-chloro-2-cyano-4,4,4-trifluorobut-2-enoate (WO 8703781 A1, 2.79 g, 13.1 mmol) in diethyl ether (6 ml). The reaction mixture was then stirred at room temperature overnight. The reaction mixture was pre-absorbed onto silica and purified by column chromatography with gradient elution, hexane:ethyl acetate

107

[4:1 to 2:1]. The appropriate fractions were combined and concentrated to give the titled compound (2.3 g).

$^1$H-NMR (CDCl3): 3.86-3.88 (3H), 5.30-5.40 (2H), 7.86-7.91 (2H)

Preparation 109

2,6-dichloro-4-[(trifluoromethyl)thio]phenylamine

To a solution of 4-[(trifluoromethyl)thio]phenylamine (EP 546391 A2, 4.8 g, 25.0 mmol) in acetonitrile (50 ml), at 50° C., was added N-chlorosuccinimide (6.7 g, 50.0 mmol). The reaction mixture was then stirred at 50° C. for 1 h. To the reaction mixture was added water (150 ml) and the mixture was extracted with dichloromethane (100 ml). The combined extracts were dried (MgSO$_4$) and concentrated in vacuo to give the titled compound (1.0 g).

Preparation 110

2,6-dichloro-4-(difluoromethoxy)phenylamine

To a solution of 4-[(difluoromethoxy)methyl]aniline (15.0 g, 94.3 mmol) in acetonitrile (150 ml) was added N-chlorosuccinimide (25.2 g, 18.9 mmol) and the reaction mixture was stirred under nitrogen for 2 h. The reaction mixture was concentrated in vacuo and the residue was partitioned between diethyl ether (500 ml) and water (125 ml). The organic layer was separated, washed with aqueous sodium thiosulphate solution, water and brine, dried (MgSO$_4$) and treated with charcoal. The solution was then filtered and concentrated in vacuo. The residue was extracted with hexane (2×300 ml) and the combined extracts were concentrated in vacuo to give the titled compound (13.8 g).

Experimental MH$^+$ 228.0; expected 228.0

Preparation 111

N-(3-cyano-1-[2,6-dichloro-4-pentafluorothiophenyl]-5-{[3-(dimethylamino)propyl]amino}-1H-pyrazol-4-yl)-N-(methylsulfonyl)methanesulfonamide To a mixture of Preparation 33 (550 mg, 1.0 mmol) and triethylamine (0.33 ml, 2.3 mmol) in dichloromethane (15 ml), at 0° C., was added dropwise methanesulphonyl chloride (0.19 ml, 2.3 mmol). The reaction mixture was allowed to warm to room temperature and stirred for 16 h. To the reaction mixture was added water (10 ml) and the two layers were separated. The aqueous layer was extracted with dichloromethane (2×20 ml) and the combined organic phases were washed with brine, dried (MgSO$_4$) and concentrated in vacuo to give the titled compound (600 mg).

Experimental MH$^+$ 635.0; expected 635.0

The invention claimed is:

1. A method of treating a parasitic infestation or infection in a non-human animal or plant comprising administration of a therapeutically effective amount of a compound of Formula 1

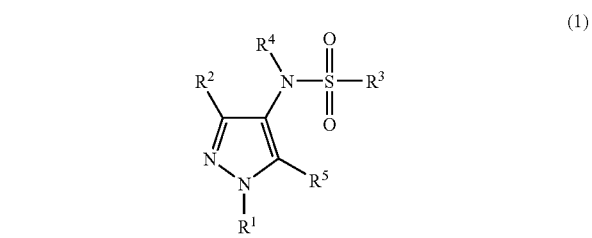

or a pharmaceutically, veterinarily, or agriculturally acceptable salt thereof, wherein $R^1$ is phenyl optionally substituted by one or more groups independently selected from the group consisting of halo, cyano, hydroxy, $C_{1-6}$ alkyl, $C_{1-6}$ haloalkyl, $C_{1-6}$ alkoxy, $C_{1-6}$ haloalkoxy, $C_{1-6}$ alkanoyl, $C_{1-6}$ haloalkanoyl, —S(O)$_n C_{1-6}$alkyl, —S(O)$_n C_{1-6}$haloalkyl and pentafluorothio;

$R^2$ is cyano;

$R^3$ is $C_{1-6}$ alkyl, $C_{1-6}$ haloalkyl, or —(C$_{0-3}$alkylene)-phenyl;

$R^4$ is hydrogen, $C_{1-6}$ alkyl, $C_{1-6}$haloalkyl, —(C$_{0-3}$alkylene)-R$^7$ or —(C$_{1-3}$alkylene)-R$^8$;

or $R^3$ and $R^4$ taken together with the nitrogen and sulphur atoms to which they are attached form a 4 to 7-membered ring;

$R^5$ is hydrogen;

$R^6$ is $C_{1-6}$ alkyl or haloalkyl;

$R^7$ is $C_{3-8}$cycloalkyl, —S(O)$_n$R$^9$, phenyl, het, —CO$_2$R$^6$ or C(O)N(R$^a$)R$^b$;

$R^8$ is hydroxy, $C_{1-6}$ alkoxy, $C_{1-6}$ haloalkoxy, cyano, —N(R$^a$)R$^b$ or —O—C(O)R$^6$;

$R^9$ is $C_{1-6}$ alkyl, $C_{1-6}$ haloalkyl, $C_{3-8}$cycloalkyl, —N(R$^a$) R$^b$, phenyl or het;

$R^a$ and $R^b$ independently represent hydrogen, $C_{1-6}$ alkyl, $C_{1-6}$ haloalkyl, $C_{2-6}$ alkenyl or $C_{2-6}$ haloalkenyl, or $R^a$ additionally is —(C$_{0-3}$alkylene)-$C_{3-8}$ cycloalkyl, —(C$_{0-3}$ alkylene)-phenyl or —(C$_{0-3}$alkylene)-het, or together $R^a$ and $R^b$ form a 4- to 7-membered ring, optionally substituted by one or more groups independently selected from the group consisting of halo, hydroxy, $C_{1-6}$ alkyl, $C_{1-6}$haloalkyl, $C_{1-6}$ alkoxy and $C_{1-6}$haloalkoxy;

n is the integer 0, 1 or 2;

where het represents a four- to seven-membered heterocyclic group, which is aromatic or non-aromatic and which contains one or more heteroatoms selected from the group consisting of nitrogen, oxygen, sulfur and mixtures thereof;

where both phenyl and het may be optionally substituted, where the valence allows, by one or more substituents independently selected from the group consisting of halo, hydroxy, cyano, nitro, $C_{1-6}$ alkyl, $C_{1-6}$haloalkyl, $C_{1-6}$ alkenyl, $C_{1-6}$haloalkenyl, $C_{1-6}$alkoxy, $C_{1-6}$haloalkoxy, $C_{3-8}$ cycloalkyl, $C_{1-6}$ alkanoyl, $C_{1-6}$ haloalkanoyl, $C_{1-6}$ alkylcarbonyloxy, $C_{1-6}$ alkoxycarbonyl and NR$^a$R$^b$;

where $C_{3-8}$cycloalkyl may be optionally substituted by one or more groups independently selected from the group consisting of halo, $C_{1-6}$alkyl, $C_{1-6}$haloalkyl, $C_{1-6}$alkenyl, $C_{1-6}$haloalkenyl, hydroxy, $C_{1-6}$alkoxy and $C_{1-6}$haloalkoxy; and where any alkylene or alkenylene group may be optionally substituted by one or more halo.

2. The method of claim 1 wherein $R^1$ of the Formula (1) compound is a phenyl group which bears chloro substituents at the 2- and 6-positions, and a substitutent at the 4-position selected from the group consisting of trifluoromethyl, difluoromethoxy, trifluoromethoxy, trifluoromethylthio and pentafluorothio.

3. The method of claim 2 wherein $R^3$ is $C_{1-6}$ alkyl or $C_{1-6}$ haloalkyl.

4. The method of claim 3 wherein $R^3$ is methyl.

5. The method of claim 4 wherein $R^4$ is hydrogen, methyl, ethyl, trifluoromethyl, 2,2-difluoroethyl, 2,2,2-trifluoroethyl, methylsulfonyl, trifluoromethylsulfonyl, 2,2,2-trifluoroethylsulfonyl, aminosulfonyl, N,N-dimethylaminosulfonyl, methylsulfonymethyl, cyclopropyl, cyclobutyl, cyclopropylmethyl, 1-(trifluoromethyl)cyclopropylmethyl, cyanomethyl, methoxycarbonyl, triazolylethyl, pyrimidin-4-ylmethyl, 1,2,4-oxadiazol-3-ylmethyl, pyrazol-3-ylmethyl, 1-methyl-1H-imidazol-2-yl, 5-methyl-isoaxazol-3-ylmethyl, 2-pyridin-4-ylethyl, aminocarbonylmethyl, benzyl or 4-fluorobenzyl.

6. The method of claim 1 wherein the Formula (1) compound is selected from the group consisting of N-{3-cyano-1-[2,6-dichloro-4-(trifluoromethyl)phenyl]-1H-pyrazol-4-yl}-1,1,1-trifluoro-N-methylmethanesulfonamide;

N-{3-cyano-1-[2,6-dichloro-4-(trifluoromethyl)phenyl]-1H-pyrazol-4-yl}-N-(methylsulfonyl)methanesulfonamide;

N-{3-cyano-1-[2,6-dichloro-4-pentafluorothiophenyl]-1H-pyrazol-4-yl}-N-(methylsulfonyl)methanesulfonamide;

N-{3-cyano-1-[2,6-dichloro-4-(trifluoromethyl)phenyl]-1H-pyrazol-4-yl}methanesulfonamide; and N-{3-cyano-1-[2,6-dichloro-4-(trifluoromethyl)phenyl]-1H-pyrazol-4-yl}-N-(2,2,2-trifluoroethyl)methanesulfonamide;

or a pharmaceutically, veterinarily, or agriculturally acceptable salt thereof.

7. The method of claim 1, wherein the non-human animal is livestock or companion animals.

8. The method of claim 7 wherein livestock is sheep, pigs, or cattle.

9. The method of claim 7 wherein the companion animal is a cat, dog, or horse.

10. The method of claim 1, wherein the parasitic infestation or infection in a non-human animal or plant is caused from arthropods, arachnids, nematodes, or helminthes.

11. The method of claim 1, wherein the compound of Formula (1) is administered orally, topically, or parenterally to the non-human animal.

12. The method of claim 1, wherein the parasitic infestation or infection is in a plant.

13. The method of claim 1, further comprising one or more biologically active compounds selected from the group consisting of insecticides, acaricides, anthelmintics, fungicides, nematocides, antiprotozoals, bactericides, growth regulators, entopathogenic bacteria, viruses, and fungi.

* * * * *